US009174996B2

(12) United States Patent
Yu et al.

(10) Patent No.: US 9,174,996 B2
(45) **Date of Patent: *Nov. 3, 2015**

(54) PROTEIN KINASE INHIBITORS

(71) Applicant: Astar Biotech LLC, Richmond, VA (US)

(72) Inventors: Chunrong Yu, Glen Allen, VA (US); Haihong Huang, Beijing (CN); Dongfeng Zhang, Beijing (CN); Peng Li, Beijing (CN)

(73) Assignee: Astar Biotech LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,156

(22) Filed: Aug. 26, 2014

(65) Prior Publication Data

US 2014/0364436 A1 Dec. 11, 2014

Related U.S. Application Data

(63) Continuation-in-part of application No. 13/561,960, filed on Jul. 30, 2012, now Pat. No. 8,859,553.

(51) Int. Cl.

| | |
|---|---|
| ***A61K 31/50*** | (2006.01) |
| ***A61K 31/501*** | (2006.01) |
| ***C07D 487/04*** | (2006.01) |
| ***C07D 403/12*** | (2006.01) |
| ***C07D 403/10*** | (2006.01) |
| ***C07D 237/20*** | (2006.01) |
| ***C07D 239/42*** | (2006.01) |
| ***C12N 9/12*** | (2006.01) |
| ***A61K 31/33*** | (2006.01) |

(52) U.S. Cl.

CPC .............. *C07D 487/04* (2013.01); *A61K 31/33* (2013.01); *C07D 237/20* (2013.01); *C07D 239/42* (2013.01); *C07D 403/10* (2013.01); *C07D 403/12* (2013.01); *C12N 9/1205* (2013.01)

(58) Field of Classification Search

CPC .. C07D 237/20; C07D 239/42; C07D 403/10; C07D 403/12; C07D 487/04; C12N 9/1205

USPC .......... 514/248, 252.02, 252.05, 252.19, 275; 544/236, 238, 295, 331

See application file for complete search history.

(56) References Cited

FOREIGN PATENT DOCUMENTS

WO WO 2012089106 A1 * 7/2012

OTHER PUBLICATIONS

STN 2012:960157 CAPLUS, Jul. 5, 2012.*

* cited by examiner

*Primary Examiner* — Wu-Cheng Winston Shen
*Assistant Examiner* — Jean Cornet

(57) ABSTRACT

The present invention relates to compounds of Formula VIII with absolute configuration R or S:

VIII

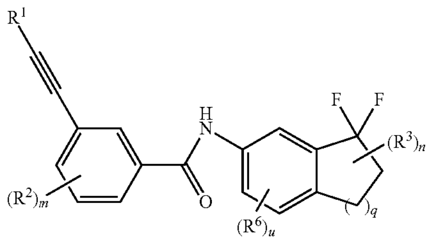

as well as pharmaceutically acceptable salts, hydrates, or solvates thereof, wherein the variables are described herein. The present invention further relates to pharmaceutical compositions which comprise the compounds of Formula VIII, and to methods for inhibiting protein kinase and methods of treating diseases, such as cancers, inflammation.

8 Claims, 5 Drawing Sheets

PROTEIN KINASE INHIBITORS

FIELD OF THE INVENTION

The present invention describes novel alkynyl derivatives with inhibitory activity on protein kinases and a pharmaceutical composition for preventing or treating diseases involving abnormal cell growth.

BACKGROUND OF THE INVENTION

Protein kinases are a group of enzymes for phosphorylation of hydroxyl groups in serine, threonine, and tyrosine moieties of protein. They are essential in growth factor signal transduction inducing cell growth, differentiation, and proliferation. Human protein kinases can be divided into tyrosine protein kinases and serine/threonine protein kinases. Tyrosine protein kinases can be further divided into receptor and cytoplasma/non-receptor kinases (Manning et al., Science, 2002, 298, 1912). Receptor tyrosine kinases possess cell surface domains to interact with growth factors, and cytoplasma domains to conduct phosphorylation of tyrosine moieties. As such, a growth factor can bind to the growth factors receptor site, thereby triggering polymerization of the receptor tyrosine kinase, and autophosphorylation of the tyrosine moieties in cytoplasma. Subsequently, sequential phosphorylation of subfamily proteins proceeds as signal transduction progresses, leading to overexpression of transcription factors and eventually cancer. A mutation or an overexpression of certain protein kinases may impact the signal transduction in a normal cell resulting in the imbalance of homeostasis in body. For example, continuous signal transduction may lead to cancer, inflammation, metabolic syndromes, and CNS diseases.

The bcr/abl fusion gene, formed by rearrangement of the breakpoint cluster region (bcr) on chromosome 22 with the c-abl proto-oncogene on chromosome 9, is present in CML (chronic myeloid leukemia) patients. The chromosome containing bcr/abl gene is referred to as Philadelphia chromosome (Nowell, J. Natl. Cancer Inst., 1960; 25:85). In the bcr/abl fusion gene, the bcr gene part contains oligomerization domains, and the abl gene part contains tyrosine domains. 3 principle forms (p190, p210 and p230 kDa) of bcr/abl gene, determined by the breakpoints of the bcr gene, have been reported. Gleevec (imatinib mesylate, STI-571) is the first targeted anti-cancer agent which was developed by Norvartis and released in 2002. Gleevec can selectively inhibit bcr/abl by inhibiting tyrosine kinases of abl. Gleevec is commonly used as standard treatment for CML. But acquired resistance to Gleevec became a serious problem. There are various mechanisms to cause the acquired Gleevec-resistance including amplification of bcr/abl gene, loss of bcr/abl gene, point mutations of bcr/abl gene. Among them, the most important factor inducing the acquired Gleevec-resistance is T315I-bcr/abl point mutation within the abl kinase domain. Multiple creative endeavors to overcome the acquired Gleevec-resistance were engaged. The recently released drugs such as Nilotinib and Dasatinib effectively inhibit many point-mutations of abl kinase domains generated by the acquired Gleevec-resistance. However, Nilotinib and Dasatinib are unable to inhibit T315I-bcr/abl mutant species. Therefore, there are a number of attempts to develop a medicine inhibiting T315I-bcr/abl mutation. Vascular endothelial growth factors (VEGFs) mediate a plethora of biological process in endothelial cells such as cell survival, proliferation, differentiation, angiogenesis, and migration. VEGFs are primarily produced by vascular endothelial, hematopoietic and stromal cells in response to hypoxia and upon stimulation of growth factors such as TGFs, PDGFs or interleukins. VEGFs bind to their high-affinity specific receptors VEGFRs (VEGFR-1, -2, and -3). Each VEGF isoform binds to a particular subset of these receptors leading to the formation of receptor homo- and heterodimers that activates discrete signaling pathways and executes its biological functions such as angiogenesis [Cébe-Suarez S, Zehnder-Fjällman A, Ballmer-Hofer K. *Cell Mol Life Sci.* 2006 March; 63(5): 601-15]. Angiogenesis provides tumors with nutrients, oxygen, and path for cancer cell spread. Therefore, it is essential for cancer cell proliferation and spread. Angiogenesis in normal body is balanced by co-regulation between angiogenic stimulators and angiogenic suppressors. However, in off-balanced cancer cells, VEGFR is activated by growth factors such as VEGF which have a great effect on vascular endothelial cells [Ann Hoeben, Bart Landuyt, Martin S. Highley, Hans Wildiers, Allan T. Van Oosterom and Ernst A. De Bruijn. Pharmacological Reviews. 2004 vol. 56(4): 549-580]. Various inhibitors (small synthetic molecules) of VEGF receptor tyrosine kinases are being developed, most of which are able to be used in solid tumors and to inhibit angiogenesis activated only in cancer cells and have a tremendous medicinal action with fairly low side effects.

SUMMARY OF THE INVENTION

The present invention relates to compounds which have protein kinase inhibitory activity, which are valuable pharmaceutically active compounds for the therapy to treat abnormal cell growth diseases, for example tumors in cancer patients.

In one aspect, the present invention provides compounds of Formula I, or a pharmaceutically acceptable salt, isomer, hydrate, and solvate thereof:

I

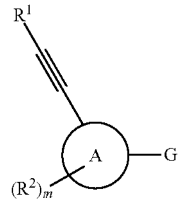

Wherein, ring A is a 4- to 8-membered heterocyclyl ring containing 1-2 heteroatoms selected from O, N and S, a 5- to 10-membered heteroaryl ring containing 1-3 heteroatoms selected from O, N and S, or a 6- to 12-membered aryl ring, wherein the heterocyclyl ring, heteroaryl ring and aryl ring are optionally and independently substituted with $(R^2)_m$;

$R^2$ is independently H, halogen, CN, $CH_2CN$, $NO_2$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^aC(O)R^d$, $NR^aC(O)OR^d$, $NR^eR^f$, or $(CR^g_2)_t$—$S(O)_2R^c$;

$R^1$ is aryl, heteroaryl, heterocyclyl, alkyl, or cycloalkyl, wherein said aryl, heteroaryl, heterocyclyl, alkyl and cycloalkyl are optionally and independently substituted with: halogen, CN, $CH_2CN$, $NO_2$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^aC(O)R^d$, $NR^aC(O)OR^d$, $NR^eR^f$, $(CR^g_2)_t$—$S(O)_2R^c$, aryl, heterocyclyl, or heteroaryl;

each $R^a$ is independently H, $C_1$-$C_6$ alkyl, $C_3$-$C_{10}$ cycloalkyl, heteroaryl or aryl, wherein said alkyl, cycloalkyl, heteroaryl and aryl are optionally and independently substituted with aryl, heteroaryl or heterocyclyl;

each $R^b$ is independently $C_1$-$C_6$ alkyl, $C_3$-$C_{10}$ cycloalkyl or aryl, wherein said alkyl, cycloalkyl and aryl are optionally and independently substituted with 1 to 3 groups selected from $C_3$-$C_{10}$ cycloalkyl and halo substituents;

each $R^c$ is independently H, $C_1$-$C_6$ alkyl, $C_3$-$C_{10}$ cycloalkyl, heteroaryl or aryl, wherein said alkyl, cycloalkyl, heteroaryl and aryl are optionally and independently substituted with aryl, heteroaryl or heterocyclyl;

each $R^d$ is independently H, $C_1$-$C_6$ alkyl or aryl, wherein said alkyl and aryl are optionally substituted with 1 to 3 halo substituents;

each of $R^e$ and $R^f$ is independently $C_1$-$C_6$ alkyl, or a 4- to 8-membered heterocyclyl containing 1 to 2 heteroatoms each independently selected from O, S, or N, wherein said heterocyclyl and alkyl are optionally substituted with 1 to 4 groups selected from halo and alkyl groups;

each $R^g$ is independently H, F, $C_1$-$C_6$ alkyl, aryl or $CF_3$, wherein said alkyl and aryl are optionally and independently substituted with 1 to 3 groups selected from aryl, $CF_3$ and halo substituents;

each R is independently H, $C_1$-$C_6$ alkyl or $C_3$-$C_{10}$ cycloalkyl, wherein said alkyl and cycloalkyl are optionally and independently substituted with 1 to 4 halo substituents;

m is 0, 1, 2, or 3;

v is 0, 1, 2, or 3;

p is 0, 1, or 2;

t is 0, 1, 2, or 3; and

G is selected from:

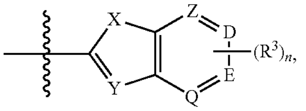

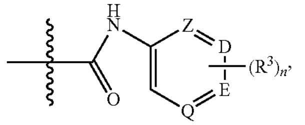

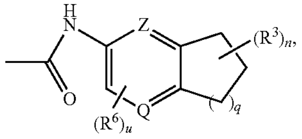

and

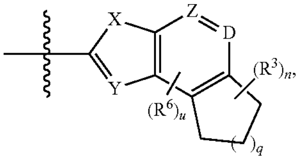

wherein, $R^3$ is independently H, halogen, $C_1$-$C_6$ alkyl, $C_3$-$C_6$ cycloalkyl, $(CH_2)_k$-(5- or 6-membered) heteroaryl, or $(CH_2)_k$-(5- or 6-membered) heterocyclyl, wherein said heteroaryl, heterocyclyl, alkyl, and cycloalkyl are independently and optionally substituted with: halogen, CN, $CH_2CN$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^eR^f$, $(CR^g_2)_t$—$S(O)_2R^c$, $NR^aC(O)R^d$, $NR^aC(O)OR^d$, aryl, heterocyclyl, or heteroaryl;

$R^6$ is independently halogen, CN, $CH_2CN$, $NO_2$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^aC(O)R^d$, $NR^aC(O)OR^d$, $NR^eR^f$, or $(CR^g_2)_t$—$S(O)_2R^c$;

X is NH or O;

Y is CH or N;

Z, D, E and Q are independently CH or N;

k is 0, 1, 2, or 3;

n is 0, 1, 2, or 3;

q is 1, or 2; and u is 0, 1, 2, or 3.

In a further aspect, the present invention provides pharmaceutical compositions comprising at least one compound of Formula I, or a salt, hydrate, isomer, or solvate thereof, and one or more pharmaceutically acceptable carriers and/or additives.

In a further aspect, the present invention provides a method for inhibiting protein kinase comprising administering a therapeutically effective amount of a compound of Formula I, or a salt, hydrate, isomer, or solvate thereof to a patient in need thereof.

In still a further aspect, the present invention provides a method of treating cancers in a human patient in need thereof, comprising administering a therapeutically effective amount of a compound of Formula I, or a salt, hydrate, isomer, or solvate thereof.

In still a further aspect, the present invention provides a method of treating inflammation in a human patient in need thereof, comprising administering a therapeutically effective amount of a compound of Formula I, or a salt, hydrate, isomer, or solvate thereof.

In still a further aspect, the present invention provides the use of a compound of Formula I, or a salt, hydrate, isomer, or solvate thereof in the manufacture of a medicament for treating cancers or inflammation.

In yet another aspect, the present invention provides a compound of Formula VIII having an absolute configuration R or S, or a pharmaceutically acceptable salt, hydrate, and solvate thereof:

VIII

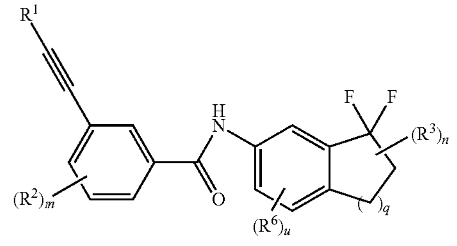

wherein, $R^1$ is selected from:

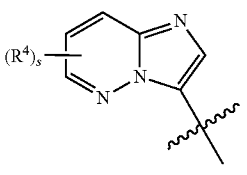

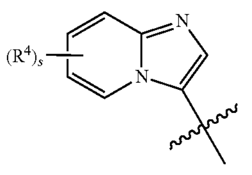

-continued

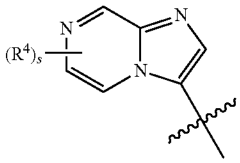
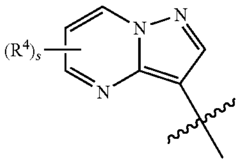
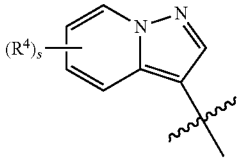
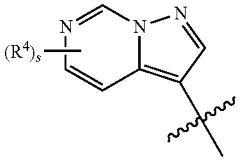
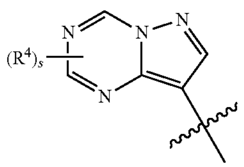
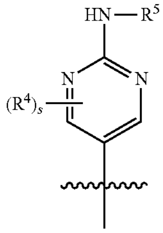
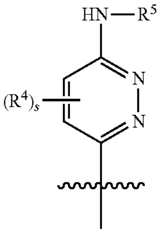
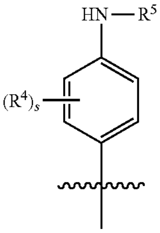
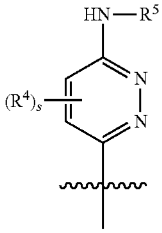
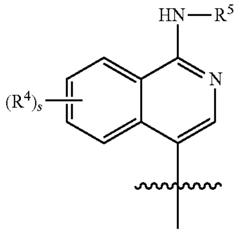
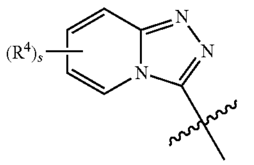
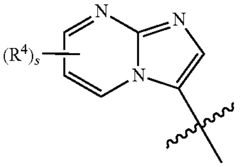

and

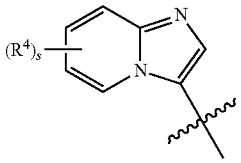

$R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

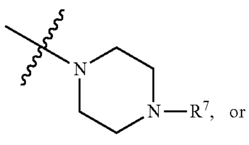

or

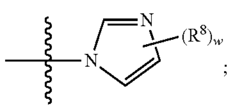

;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2; n is 0, 1, or 2; w is 0, 1, or 2; s is 0, 1, or 2; u is 0, 1, or 2; and q is 1 or 2.

In a further aspect, the compound having an absolute configuration R or S is represented by Formula VIIIa, VIIIb or VIIIc:

VIIIa

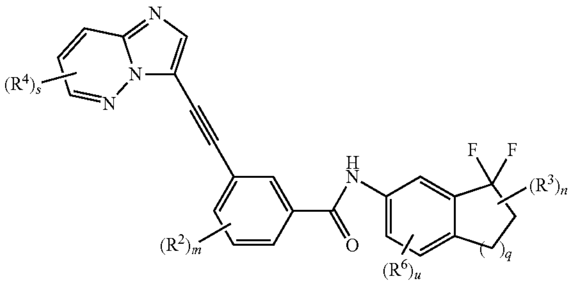

VIIIb

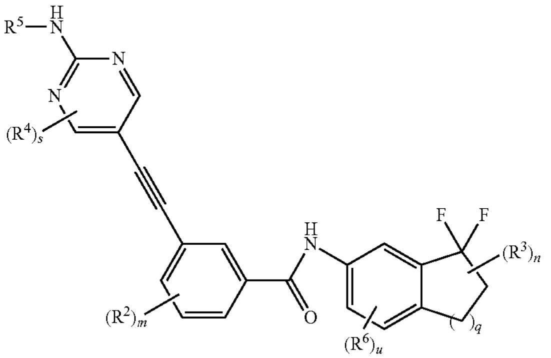

VIIIc

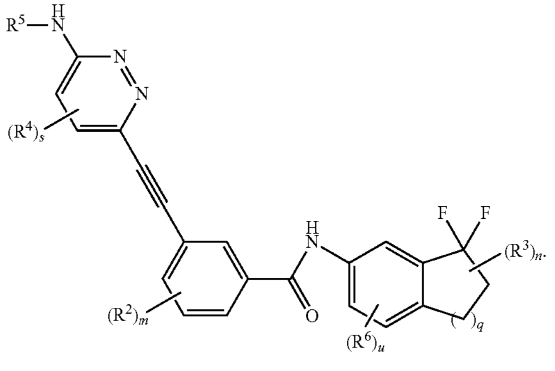

In still a further aspect, according to formula VIIIa, formula VIIIb or formular VIIIc, in which $R^2$ is H, $CH_3$, F or Cl; $R^3$ is

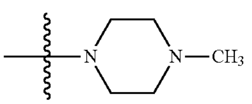

or

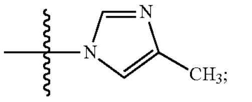

$R^5$ is cyclopropyl, cyclobutyl, or isopropyl; $R^6$ is H or $CF_3$; and s is 0, u is 0, m is 0 or 1, n is 1 and q is 1.

Particularly, the compound of formula VIII having an absolute configuration R or S is:

(R)—N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide;

(S- N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide;

(R)-3-(2-(2-(Cyclopropylamino)pyrimidin-5-yl)ethynyl)-N-(1,1-difluoro-2,3-dihydro-3-(4-methylpiperazin-1-yl)-1H-indan-6-yl)-4-methylbenzamide;

(S)-3-(2-(2-(Cyclopropylamino)pyrimidin-5-yl)ethynyl)-N-(1,1-difluoro-2,3-dihydro-3-(4-methylpiperazin-1-yl)-1H-indan-6-yl)-4-methylbenzamide;

(R)—N-(1,1-difluoro-2,3-dihydro-3-(4-methylpiperazin-1-yl)-1H-indan-6-yl)-3-(2-(imidazo[1,2-b]pyridazin-3-yl)ethynyl)-4-chlorobenzamide; or (S)-N-(1,1-difluoro-2,3-dihydro-3-(4-methylpiperazin-1-yl)-1H-indan-6-yl)-3-(2-(imidazo[1,2-b]pyridazin-3-yl)ethynyl)-4-chlorobenzamide.

(R)—N-(1,1-difluoro-2,3-dihydro-3-(4-methylpiperazin-1-yl)-1H-indan-6-yl)-3-(2-(imidazo[1,2-b]pyridazin-3-yl)ethynyl)-4-fluorobenzamide;

(S)-N-(1,1-difluoro-2,3-dihydro-3-(4-methylpiperazin-1-yl)-1H-indan-6-yl)-3-(2-(imidazo[1,2-b]pyridazin-3-yl)ethynyl)-4-fluorobenzamide.

In a further aspect, the present invention provides pharmaceutical compositions comprising at least one compound of Formula VIII with absolute configuration R or S, or a salt, hydrate, or solvate thereof, and one or more pharmaceutically acceptable carriers and/or additives.

In a further aspect, the present invention provides a method for inhibiting protein kinase comprising administering a therapeutically effective amount of a compound of Formula VIII with absolute configuration R or S, or a salt, hydrate, or solvate thereof to a patient in need thereof.

The protein kinase may be selected from a group consisting of Bcr-Abl, c-Kit, c-Src, FGFR1, FLT3, LYN and PDGFR; particularly Bcr-Able (T315I).

In still a further aspect, the present invention provides a method of treating cancers in a human patient in need thereof, comprising administering a therapeutically effective amount of a compound of Formula VIII with absolute configuration R or S, or a salt, hydrate, or solvate thereof.

The cancer may be selected from a group consisting of Chronic Myelogenous Leukemia (CML), Acute Lymphocytic Leukemia (ALL), Non-Small Cell Lung Cancer (NSCLC), Gastrointestinal stromal tumor (GIST) and Acute Myelogenous Leukemia (AML); particularly CML.

In still a further aspect, the present invention provides a method for treating inflammation in a human patient in need thereof, comprising administering a therapeutically effective amount of a compound of Formula VIII with absolute configuration R or S, or a salt, hydrate, isomer, or solvate thereof.

The inflammation may be selected from a group consisting of Asthma and Rheumatoid Arthritis.

In still a further aspect, the present invention provides the use of a compound of Formula VIII with absolute configuration R or S, or a salt, hydrate or solvate thereof in the manufacture of a medicament for treating cancers or inflammation.

The cancer may be selected from a group consisting of Chronic Myelogenous Leukemia (CML), Acute Lymphocytic Leukemia (ALL), Non-Small Cell Lung Cancer (NSCLC), Gastrointestinal stromal tumor (GIST) and Acute Myelogenous Leukemia (AML). The inflammation may be selected from a group consisting of Asthma and Rheumatoid Arthritis.

DETAILED DESCRIPTION OF THE INVENTION

Figure 1:
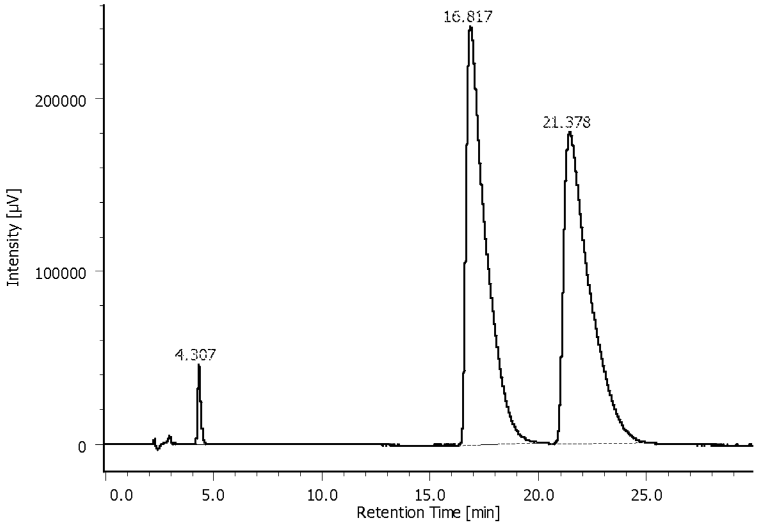
FIG. 1: shows the spectrogram for separation of the optimal isomers of Compound 36 by SFC method with a chiral column.

One aspect of the present invention is to provide novel compounds according to Formula I shown and described above. Specifically, the compounds of the invention are protein kinase inhibitors. As a result, this invention provides novel compounds according to Formula I, as well as pharmaceutically acceptable salts, hydrates, isomers or solvates thereof. Values and particular values for the variables in Formula I are provided in the following paragraphs.

In an embodiment, $R^1$ is independently aryl, or heteroaryl ring selected from:

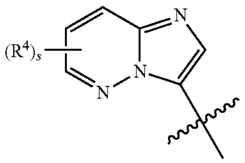

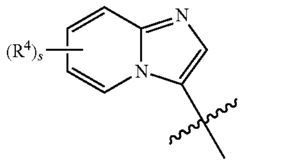

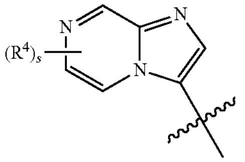

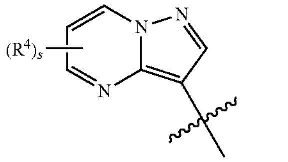

-continued

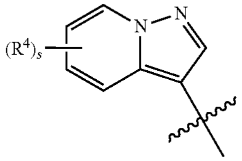

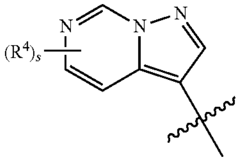

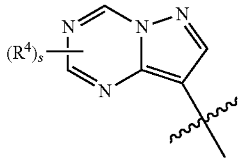

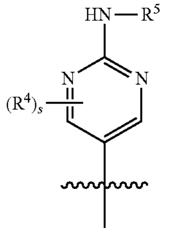

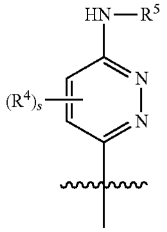

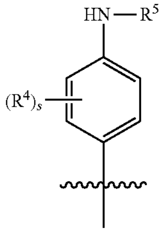

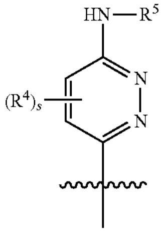

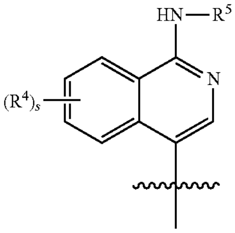

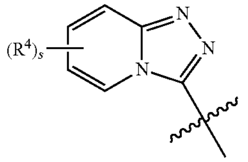

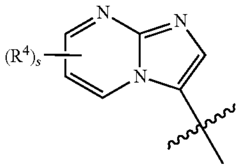

or

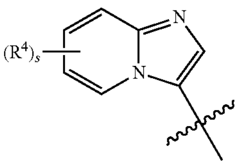

Wherein, $R^4$ is independently H, halogen, CN, $CH_2CN$, $NO_2$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^aC(O)R^d$, $NR^aC(O)OR^d$, $NR^eR^f$, or $(CR^g{}_2)_t$—$S(O)_2R^c$;

$R^5$ is H, $C_1$-$C_6$ alkyl, $C_3$-$C_6$ cycloalkyl, phenyl, or benzyl; and s is 0, 1, or 2.

In an embodiment of the compounds of Formula I, G is

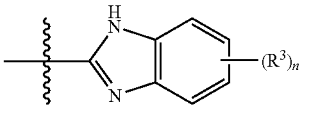

with the following structure of Formula II, and all other variables are as previously defined in Formula I.

II

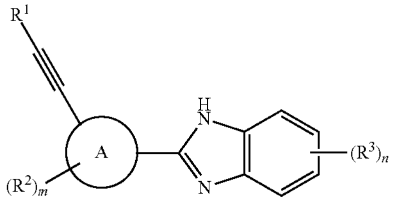

In another embodiment of the compounds of Formula II, ring A is benzene with the following structure of Formula III:

III

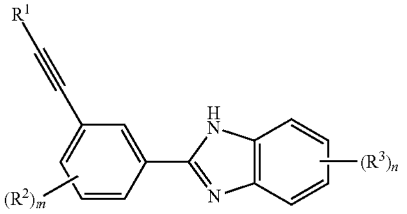

wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

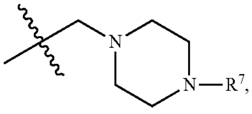

, or

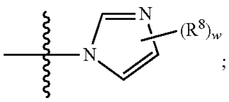

;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2; and s is 0, 1, or 2, and all other variables are as previously defined in Formula II.

In another embodiment of the compounds of Formula III, the compounds are represented by Formula IIIa, Formula IIIb, or Formula IIIc:

IIIa

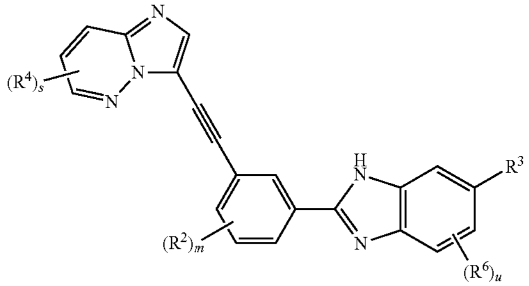

IIIb

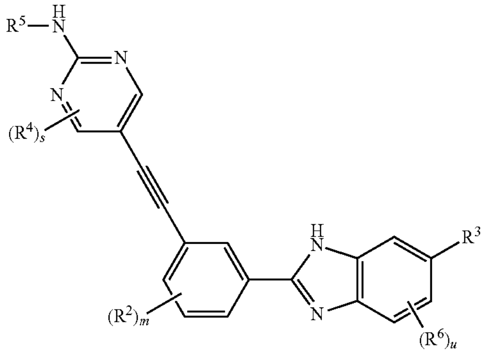

IIIc

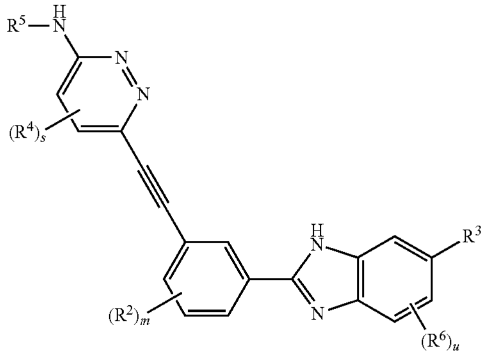

Wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

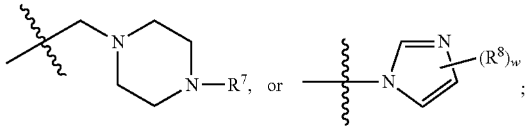

;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

w is 0, 1, or 2;

s is 0, 1, or 2; and u is 0, 1, or 2, and all other variables are as previously defined in Formula I.

In another embodiment of the compounds of Formulas IIIa-IIIc, $R^2$ is H, $CH_3$, or Cl; $R^3$ is

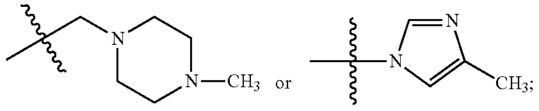

$R^5$ is cyclopropyl, cyclobutyl, or isopropyl; and $R^6$ is H or $CF_3$; and u is 0, s is 0, and m is 0 or 1.

In another embodiment of the compounds of Formula I, G is

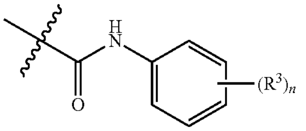

with the following structure of Formula IV, and all other variables are as previously defined in Formula I.

IV

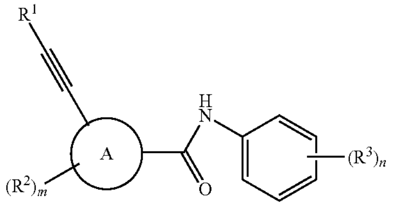

In another embodiment of the compounds of Formula IV, ring A is benzene with the following structure of Formula V:

V

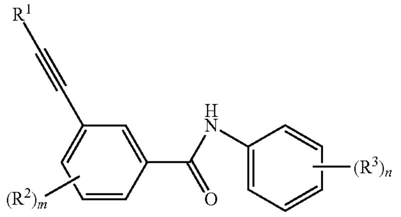

wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

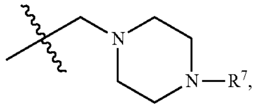, or 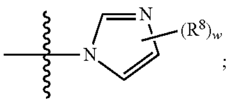;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2; and s is 0, 1, or 2, and all other variables are as previously defined in Formula IV.

In another embodiment of the compounds of Formula V, the compounds are represented by Formula Va or Formula Vb:

Va

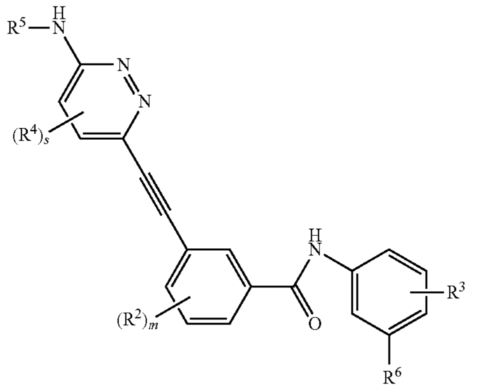

Vb

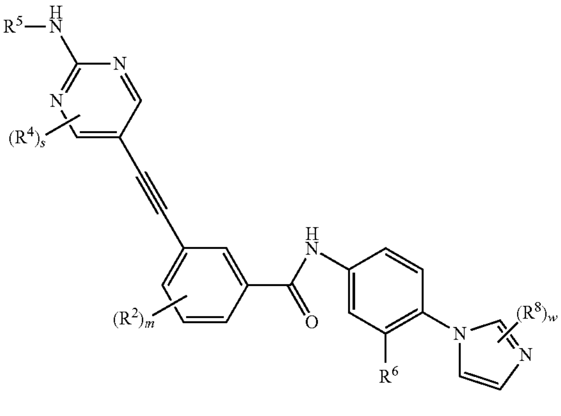

Wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

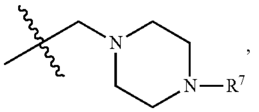, or 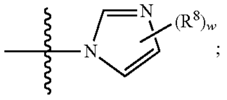;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

w is 0, 1, or 2;

s is 0, 1, or 2, and all other variables are as previously defined in Formula I.

In another embodiment of the compounds of Formulas Va-Vb, $R^2$ is H, $CH_3$, or Cl; $R^3$ is

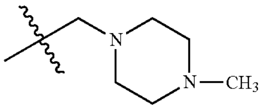 or 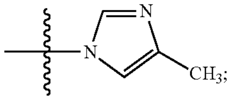;

$R^5$ is cyclopropyl, cyclobutyl, or isopropyl; $R^6$ is H or $CF_3$; and s is 0, w is 1, and m is 0 or 1.

In another embodiment of the compounds of Formula IV, ring A is heterocyclyl with the following structure of Formula VI:

VI

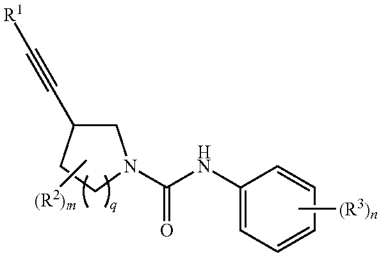

wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

R is

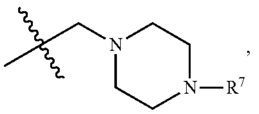, or 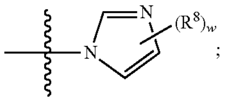;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2;

s is 0, 1, or 2; and q is 1 or 2;

and all other variables are as previously defined in Formula IV.

In another embodiment of the compounds of Formula VI, the compounds are represented by Formula VIa:

VIa

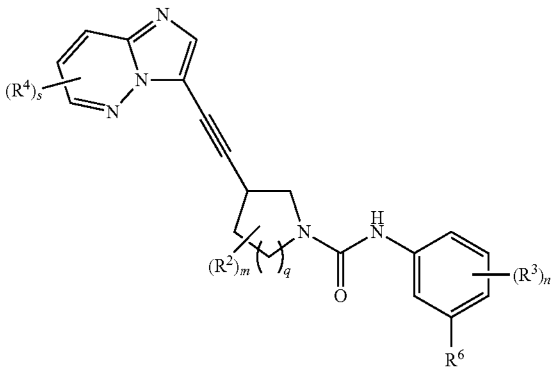

Wherein, q is 1, or 2; n is 0, 1 or 2; and all other variables are as previously defined in Formula IIIa-IIIc.

In another embodiment of the compounds of Formulas VIa, $R^2$ is H; $R^3$ is

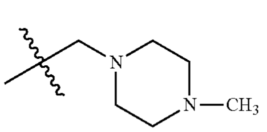

or

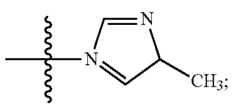

$R^6$ is H or $CF_3$; and s is 0, w is 1, m is 0, and n is 1.

In another embodiment of the compounds of Formula I, G is

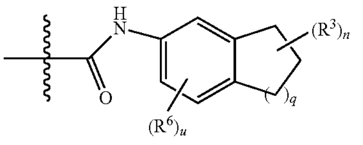

with the following structure of Formula VII:

VII

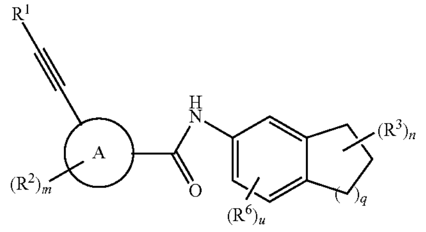

Wherein, $R^6$ is independently halogen, CN, $CH_2CN$, $NO_2$, $CF_3$, $OCF_3$, $NH_2$, $C_1$-$C_6$ alkyl, $C_3$-$C_6$ cycloalkyl, OR, SR, $NR^aS(O)_2R^b$, $(CR_2)_v$—$S(O)_pR^c$, $C(O)OR^c$, $NR^aC(O)R^d$, $NR^aC(O)OR^d$, $NR^eR^f$, or $(CR^g{}_2)_t$—$S(O)_2R^c$;

u is 0, 1, 2, or 3;

q is 1 or 2;

and all other variables are as previously defined in Formula I.

In another embodiment of the compounds of Formula VII, ring A is benzene with the following structure of Formula VIII:

VIII

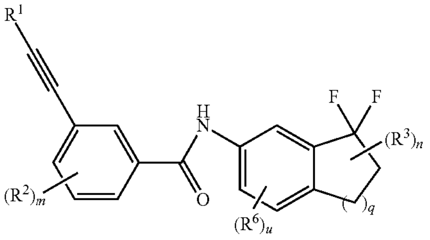

wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

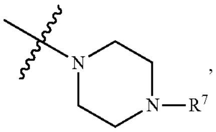

, or

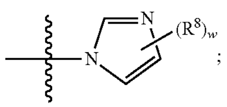

;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2;

s is 0, 1, or 2;

u is 0, 1, or 2; and q is 1 or 2, and all other variables are as previously defined in Formula VII.

Preferably, the compounds of formula VIII have an absolute configuration R or S, in which the chiral carbon is on the indanyl that connects $R^3$. More preferably, the compounds of formula VIII have an absolute configuration S.

In another embodiment of the compounds of Formula VIII, the compounds are represented by Formula VIIIa, Formula VIIIb, or Formula VIIIc:

VIIIa

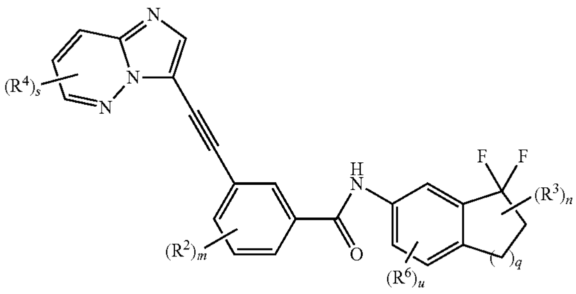

VIIIb

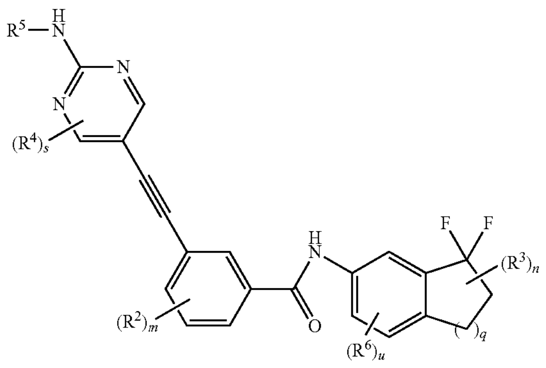

VIIIc

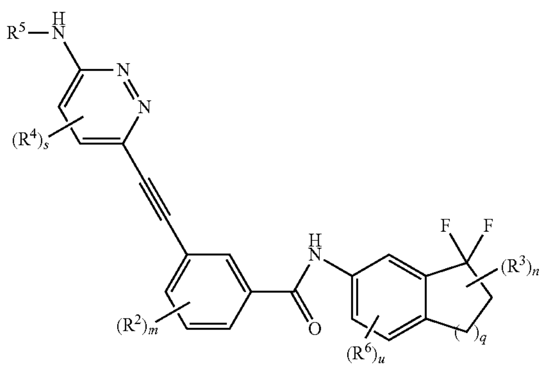

Wherein, all variables are as previously defined in Formulas VIII.

In another embodiment of the compounds of Formulas VIIIa-VIIIc, $R^2$ is H, $CH_3$, or Cl; $R^3$ is

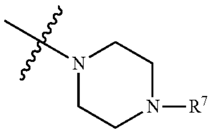

or

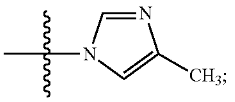

$R^5$ is cyclopropyl, cyclobutyl, or isopropyl; $R^6$ is H or $CF_3$ and s is 0, q is 1, u is 0, m is 0 or 1 and n is 1.

In another embodiment of the compounds of Formula I, G is

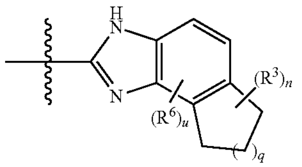

with the following structure of Formula IX, wherein u=0, 1, or 2; and all other variables are as previously defined in Formula VII.

The compounds of formula VIIIa, formula VIIIb or formula VIIIc preferably have an absolute configuration R or S, in which the chiral carbon is on the indanyl that connects $R^3$; more preferably, the compound of formula VIII has an absolute configuration S.

According to a preferred embodiment, in formula VIIIa, formula VIIIb or formula VIIIc having an absolute configuration R or S, $R^2$ is H, $CH_3$, F or Cl; $R^3$ is

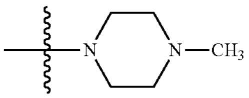

or

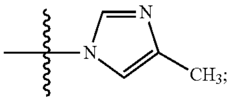

$R^5$ is cyclopropyl, cyclobutyl, or isopropyl; $R^6$ is H or $CF_3$; and s is 0, u is 0, m is 0 or 1, n is 1 and q is 1.

IX

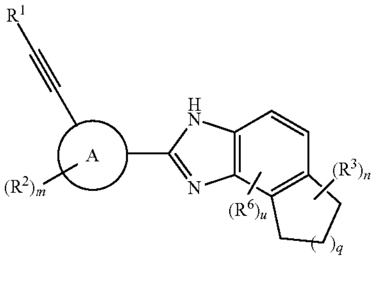

In another embodiment of the compounds of Formula IX, ring A is benzene with the following structure of Formula X:

X

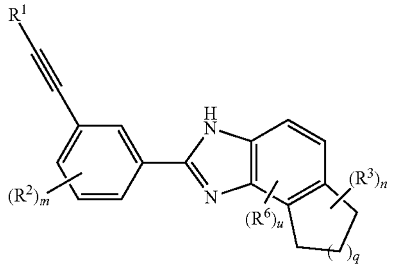

wherein, $R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

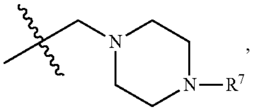

, or

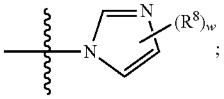

;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2;

s is 0, 1, or 2;

u is 0, 1, or 2; and q is 1 or 2;

and all other variables are as previously defined in Formula VII.

In another embodiment of the compounds of Formula X, the compounds are represented by Formula Xa, Formula Xb, or Formula Xc:

Xa

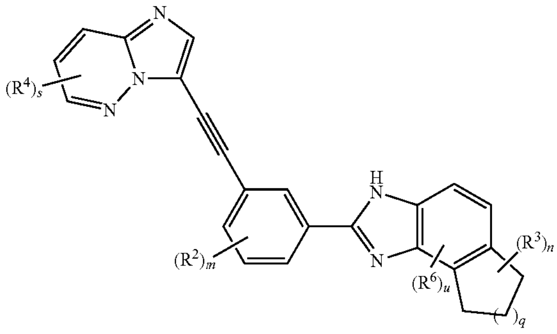

Xb

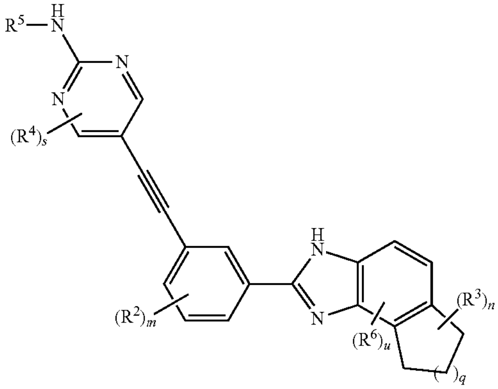

Xc

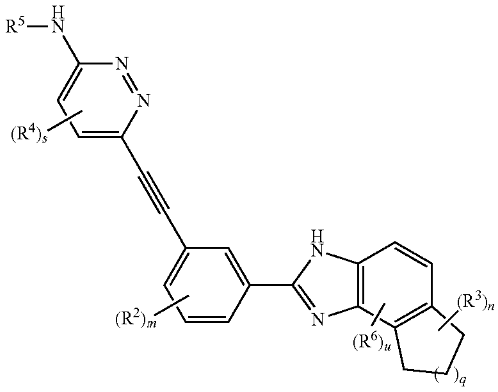

Wherein, u is 0, 1, or 2;

q is 1, or 2;

n is 0, 1, or 2;

and all other variables are as previously defined in Formulas IIIa-IIIc.

Some specific examples of the compounds of the invention include:

| Compound | Structure | HR/MS [M + H]$^+$ |
|---|---|---|
| 1 | 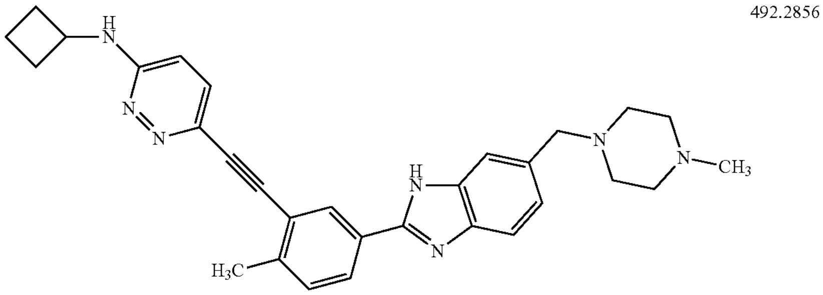 | 492.2856 |
| 2 | 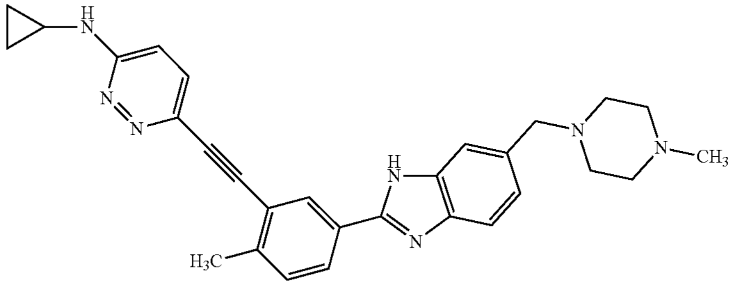 | 478.2708 |
| 3 | 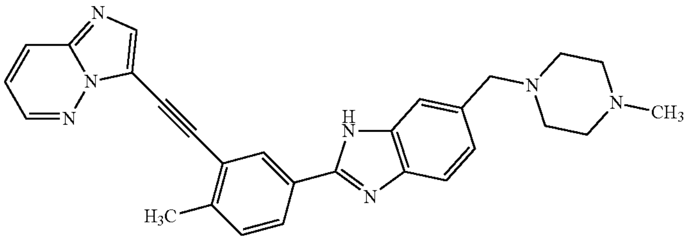 [SMILES: Cc1ccc(-c2nc3ccc(CN4CCN(C)CC4)cc3[nH]2)cc1C#Cc1cnc2cccnn12] | 462.2413 |
| 4 | 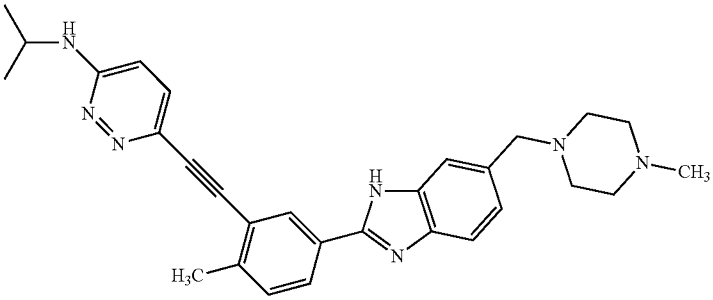 [SMILES: Cc1ccc(-c2nc3ccc(CN4CCN(C)CC4)cc3[nH]2)cc1C#Cc1ccc(NC(C)C)nn1] | 480.2847 |
| 5 | 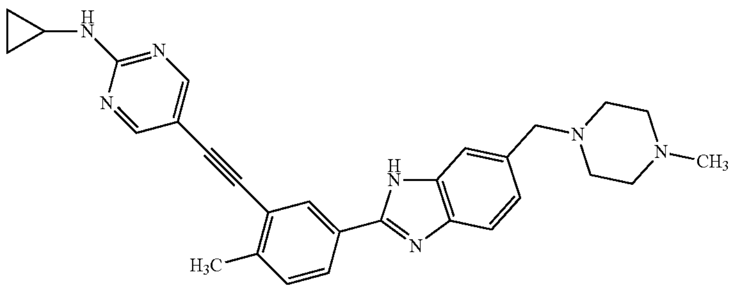 [SMILES: Cc1ccc(-c2nc3ccc(CN4CCN(C)CC4)cc3[nH]2)cc1C#Cc1cnc(NC2CC2)nc1] | 478.2718 |

-continued
| Compound | Structure | HR/MS [M + H]+ |
|---|---|---|
| 6 | 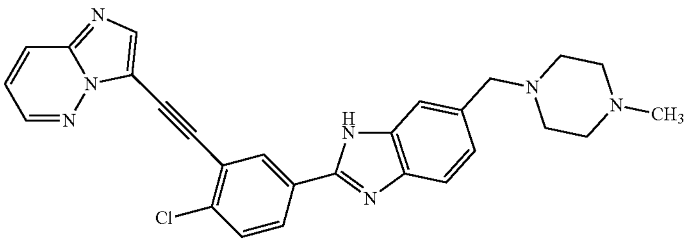 | 482.1841 |
| 7 | 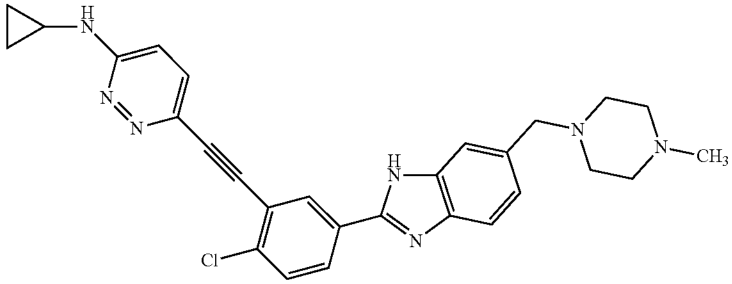 [SMILES: CN1CCN(Cc2ccc3nc(-c4ccc(Cl)c(C#Cc5ccc(NC6CC6)nn5)c4)[nH]c3c2)CC1] | 498.2150 |
| 8 | 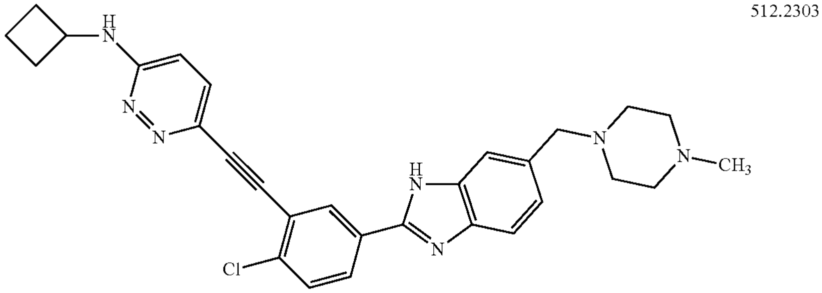 | 512.2303 |
| 9 | 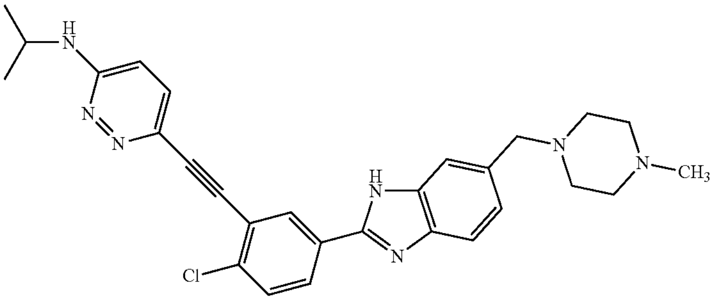 [SMILES: CC(C)Nc1ccc(C#Cc2cc(-c3nc4ccc(CN5CCN(C)CC5)cc4[nH]3)ccc2Cl)nn1] | 500.2313 |
| 10 | 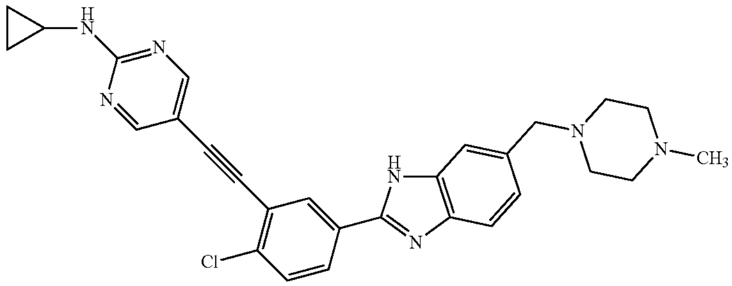 | 498.2163 |

-continued
| Compound | Structure | HR/MS [M + H]+ |
|---|---|---|
| 11 | 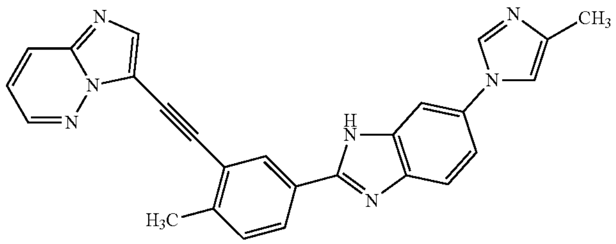 [SMILES: Cc1cn(-c2ccc3nc(-c4ccc(C)c(C#Cc5cnc6cccnn56)c4)[nH]c3c2)cn1] | 430.1778 |
| 12 | 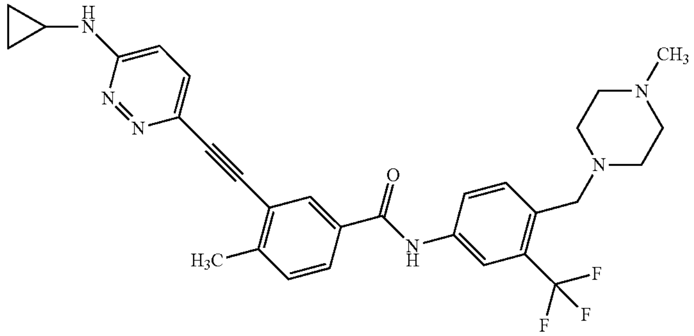 [SMILES: Cc1ccc(C(=O)Nc2ccc(CN3CCN(C)CC3)c(C(F)(F)F)c2)cc1C#Cc1ccc(NC2CC2)nn1] | 549.2568 |
| 13 | 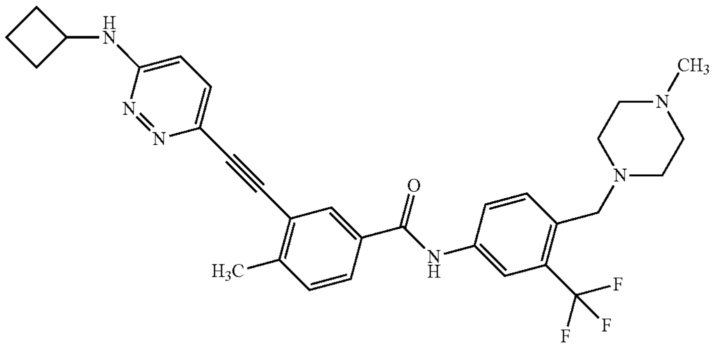 [SMILES: Cc1ccc(C(=O)Nc2ccc(CN3CCN(C)CC3)c(C(F)(F)F)c2)cc1C#Cc1ccc(NC2CCC2)nn1] | 563.2768 |
| 14 | 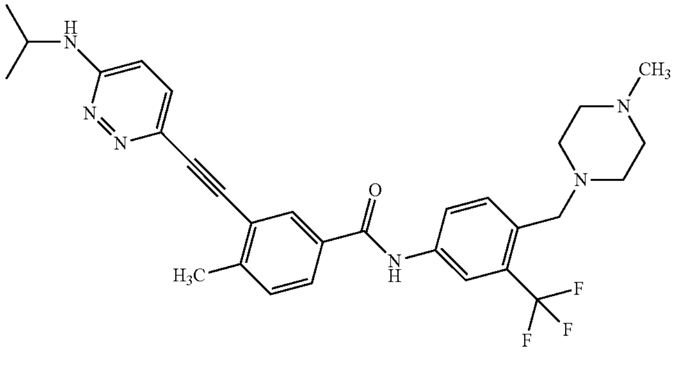 | 551.2734 |

-continued
| Compound | Structure | HR/MS [M + H]+ |
|---|---|---|
| 15 | 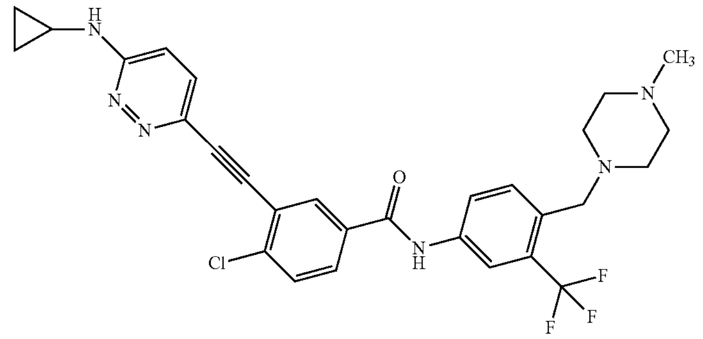 [SMILES: CN1CCN(Cc2ccc(NC(=O)c3ccc(Cl)c(C#Cc4ccc(NC5CC5)nn4)c3)cc2C(F)(F)F)CC1] | 569.2000 |
| 16 | 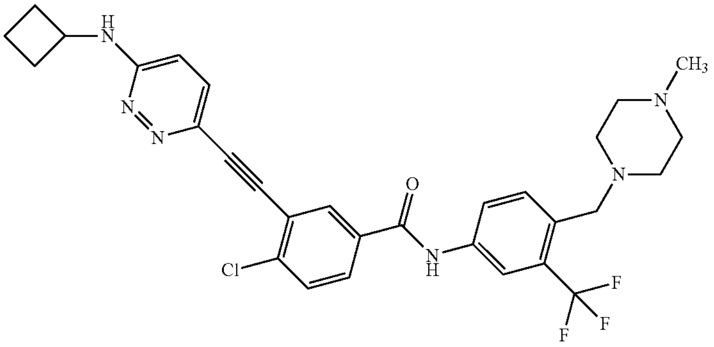 | 583.2174 |
| 17 | 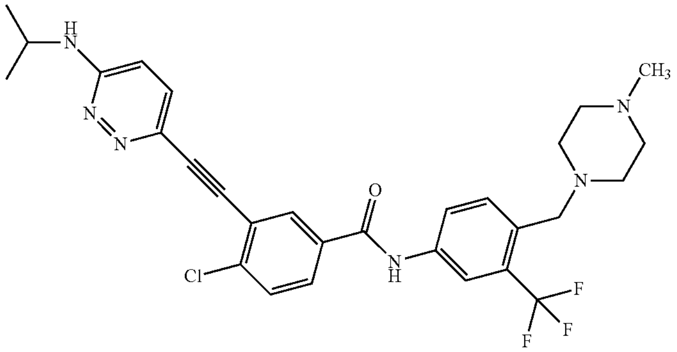 [SMILES: CC(C)Nc1ccc(C#Cc2cc(C(=O)Nc3ccc(CN4CCN(C)CC4)c(C(F)(F)F)c3)ccc2Cl)nn1] | 571.2209 |
| 18 | 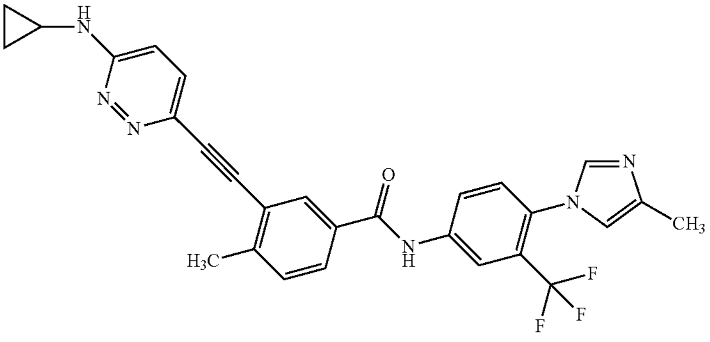 [SMILES: Cc1cn(-c2ccc(NC(=O)c3ccc(C)c(C#Cc4ccc(NC5CC5)nn4)c3)cc2C(F)(F)F)cn1] | 259.1023* [M + H]+2 |

-continued
| Compound | Structure | HR/MS [M + H]+ |
|---|---|---|
| 19 | 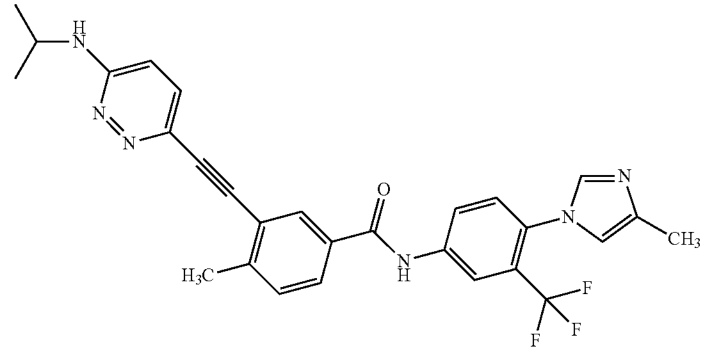 [SMILES: Cc1cn(-c2ccc(NC(=O)c3ccc(C)c(C#Cc4ccc(NC(C)C)nn4)c3)cc2C(F)(F)F)cn1] | 519.2116 |
| 20 | 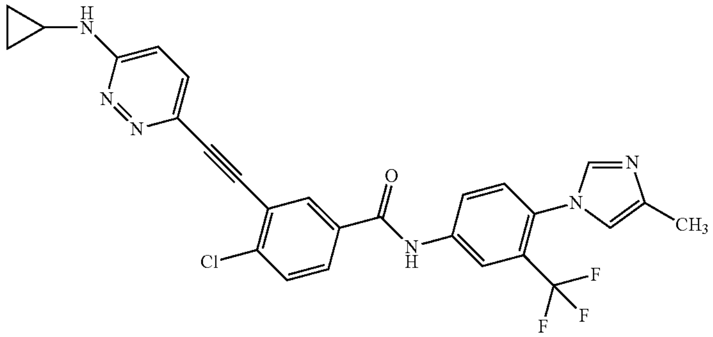 [SMILES: Cc1cn(-c2ccc(NC(=O)c3ccc(Cl)c(C#Cc4ccc(NC5CC5)nn4)c3)cc2C(F)(F)F)cn1] | 269.0735* [M + H]+2 |
| 21 | 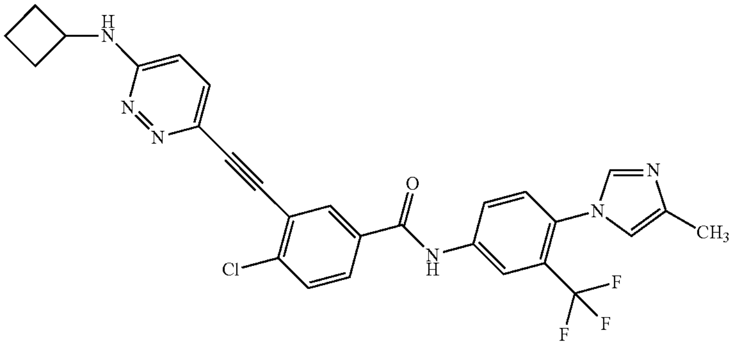 [SMILES: Cc1cn(-c2ccc(NC(=O)c3ccc(Cl)c(C#Cc4ccc(NC5CCC5)nn4)c3)cc2C(F)(F)F)cn1] | 276.0817* [M + H]+2 |
| 22 | 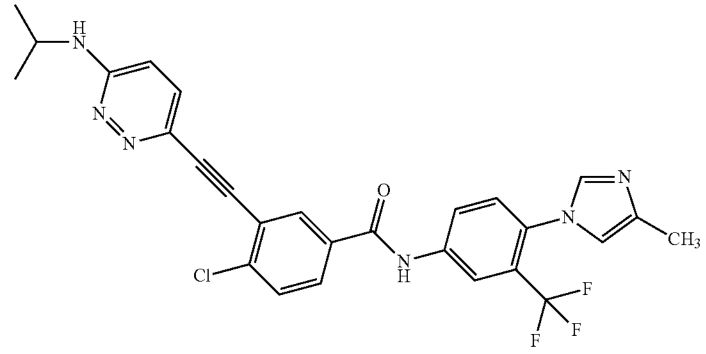 [SMILES: Cc1cn(-c2ccc(NC(=O)c3ccc(Cl)c(C#Cc4ccc(NC(C)C)nn4)c3)cc2C(F)(F)F)cn1] | 539.1592 |

-continued
| Compound | Structure | HR/MS $[M + H]^+$ |
|---|---|---|
| 23 | 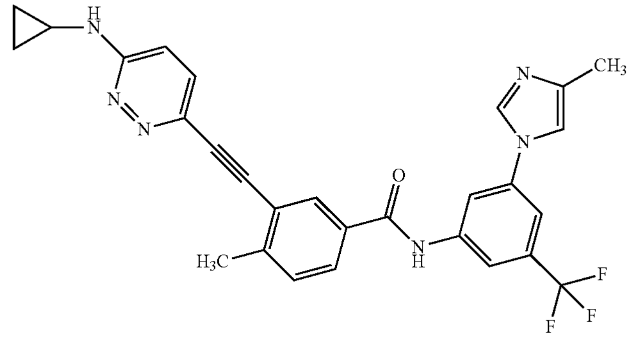 [SMILES: Cc1cn(-c2cc(NC(=O)c3ccc(C)c(C#Cc4ccc(NC5CC5)nn4)c3)cc(C(F)(F)F)c2)cn1] | 517.1950 |
| 24 | 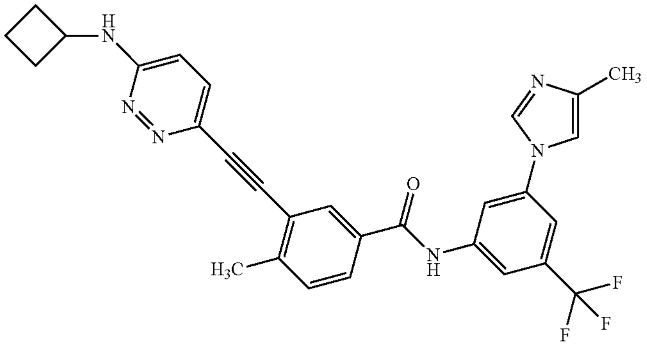 [SMILES: Cc1cn(-c2cc(NC(=O)c3ccc(C)c(C#Cc4ccc(NC5CCC5)nn4)c3)cc(C(F)(F)F)c2)cn1] | 531.2113 |
| 25 | 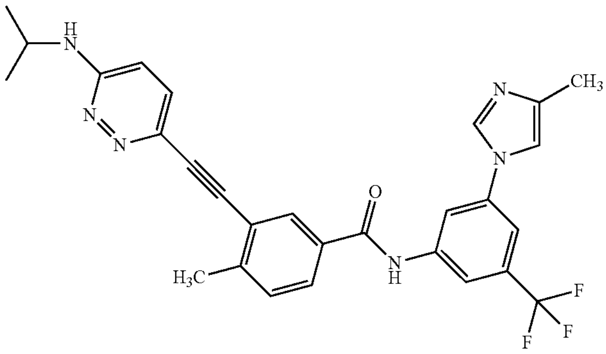 [SMILES: Cc1cn(-c2cc(NC(=O)c3ccc(C)c(C#Cc4ccc(NC(C)C)nn4)c3)cc(C(F)(F)F)c2)cn1] | 519.2121 |
| 26 | 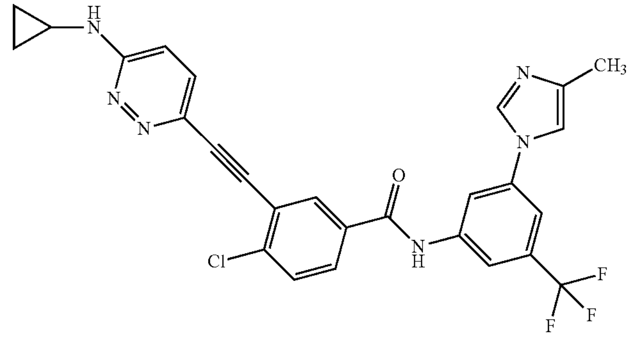 | 537.1413 |

-continued
| Compound | Structure | HR/MS [M + H]+ |
|---|---|---|
| 27 | 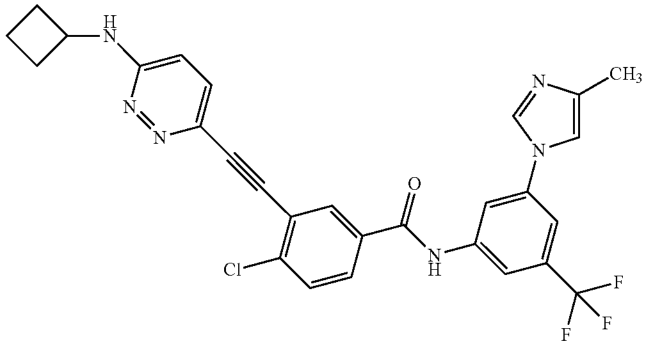 [SMILES: Cc1cn(-c2cc(NC(=O)c3ccc(Cl)c(C#Cc4ccc(NC5CCC5)nn4)c3)cc(C(F)(F)F)c2)cn1] | 276.0819* [M + H]+2 |
| 28 | 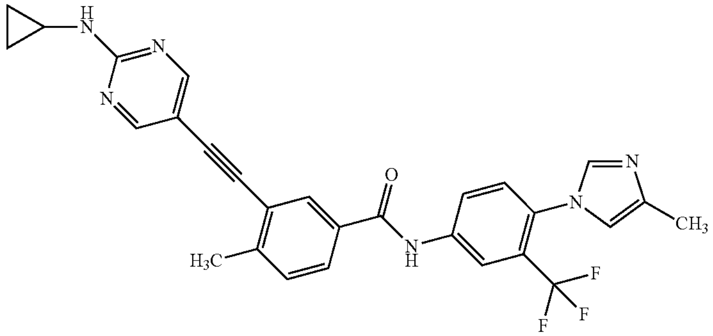 [SMILES: Cc1cn(-c2ccc(NC(=O)c3ccc(C)c(C#Cc4cnc(NC5CC5)nc4)c3)cc2C(F)(F)F)cn1] | 517.1960 |
| 29 | 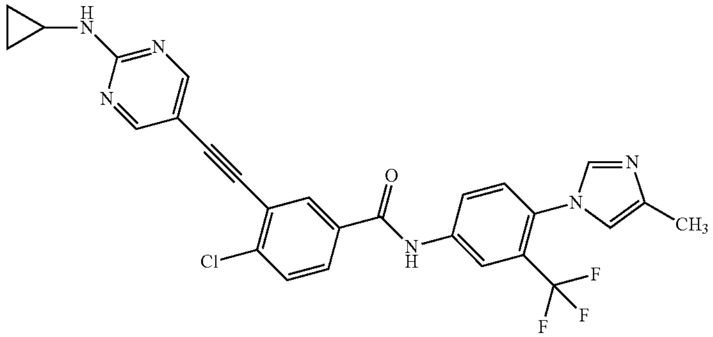 [SMILES: Cc1cn(-c2ccc(NC(=O)c3ccc(Cl)c(C#Cc4cnc(NC5CC5)nc4)c3)cc2C(F)(F)F)cn1] | 537.1417 |
| 30 | 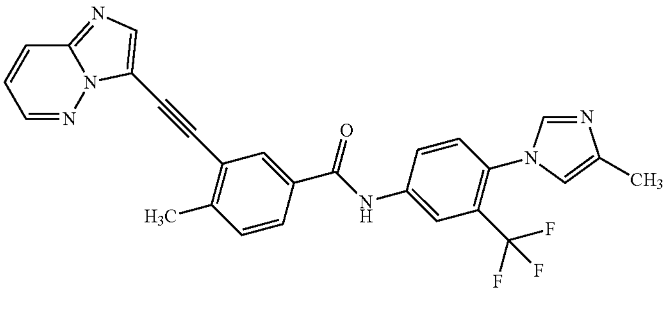 [SMILES: Cc1cn(-c2ccc(NC(=O)c3ccc(C)c(C#Cc4cnc5cccnn45)c3)cc2C(F)(F)F)cn1] | 501.1626 |

-continued
| Compound | Structure | HR/MS $[M + H]^+$ |
|---|---|---|
| 31 | 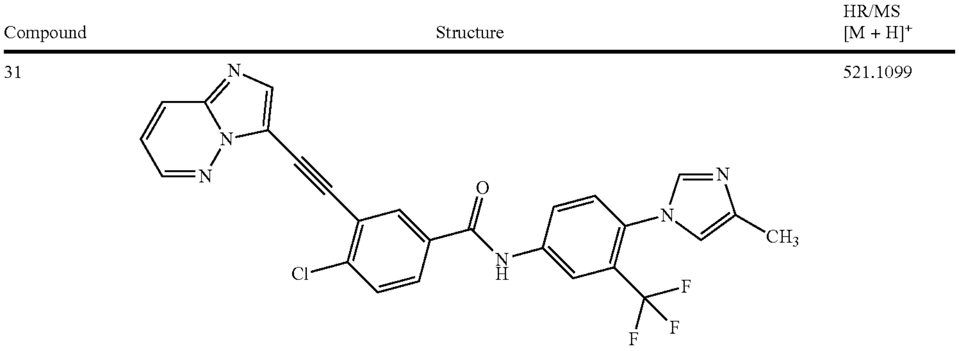 | 521.1099 |
| 32 | 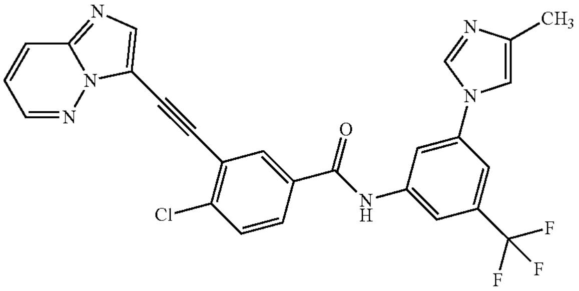 [SMILES: Cc1cn(-c2cc(NC(=O)c3ccc(Cl)c(C#Cc4cnc5cccnn45)c3)cc(C(F)(F)F)c2)cn1] | 261.0584* $[M + H]^{+2}$ |
| 33 | 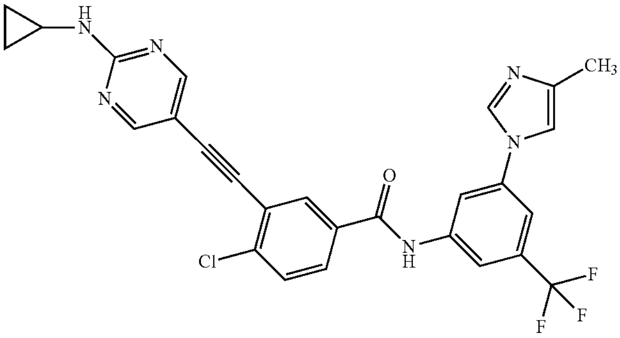 [SMILES: Cc1cn(-c2cc(NC(=O)c3ccc(Cl)c(C#Cc4cnc(NC5CC5)nc4)c3)cc(C(F)(F)F)c2)cn1] | 537.1399 |
| 34 | 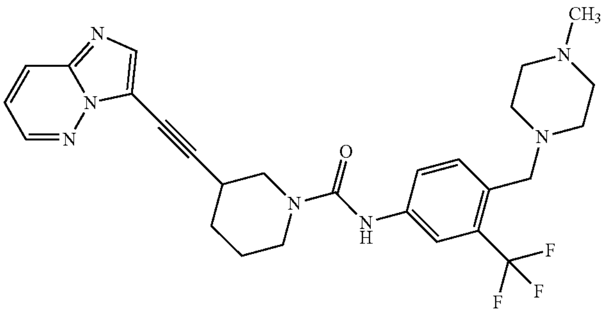 [SMILES: CN1CCN(Cc2ccc(NC(=O)N3CCCC(C#Cc4cnc5cccnn45)C3)cc2C(F)(F)F)CC1] | 526.2536 |
| 35 | 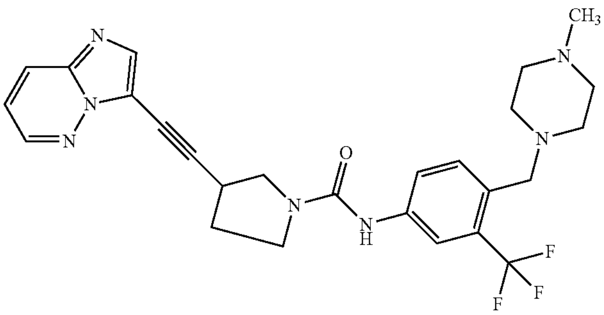 [SMILES: CN1CCN(Cc2ccc(NC(=O)N3CCC(C#Cc4cnc5cccnn45)C3)cc2C(F)(F)F)CC1] | 512.2375 |

-continued
| Compound | Structure | HR/MS [M + H]$^+$ |
|---|---|---|
| 36 | 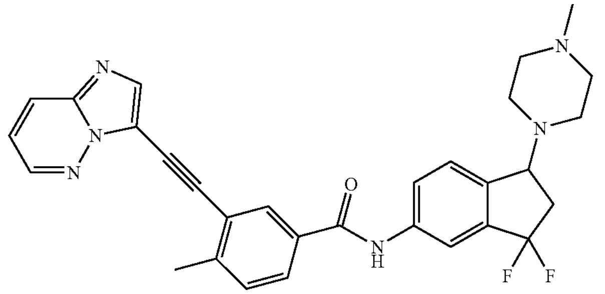 [SMILES: Cc1ccc(C(=O)Nc2ccc3c(c2)C(F)(F)CC3N2CCN(C)CC2)cc1C#Cc1cnc2cccnn12] | 264.1212* [M + 2H]$^{+2}$ |
| 36-(S) | 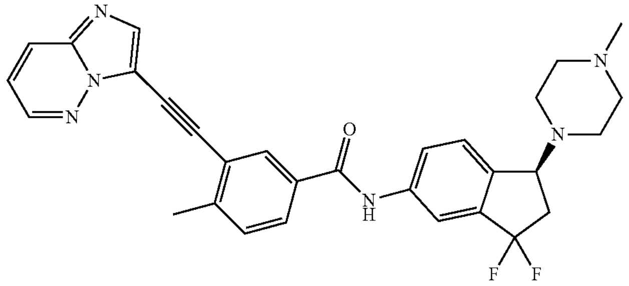 [SMILES: Cc1ccc(C(=O)Nc2ccc3c(c2)C(F)(F)C[C@@H]3N2CCN(C)CC2)cc1C#Cc1cnc2cccnn12] | 264.1218* [M + 2H]$^{+2}$ |
| 36-(R) | 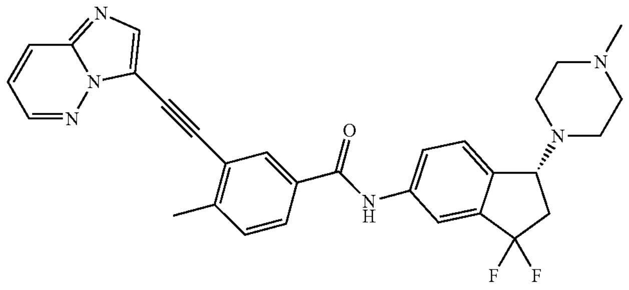 [SMILES: Cc1ccc(C(=O)Nc2ccc3c(c2)C(F)(F)C[C@H]3N2CCN(C)CC2)cc1C#Cc1cnc2cccnn12] | 264.1217* [M + 2H]$^{+2}$ |
| 37 | 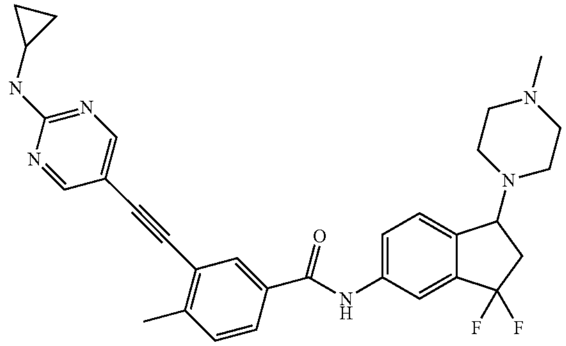 [SMILES: Cc1ccc(C(=O)Nc2ccc3c(c2)C(F)(F)CC3N2CCN(C)CC2)cc1C#Cc1cnc(NC2CC2)nc1] | 272.1370* [M + 2H]$^{+2}$ |

-continued
| Compound | Structure | HR/MS $[M + H]^+$ |
|---|---|---|
| 37-(S) | 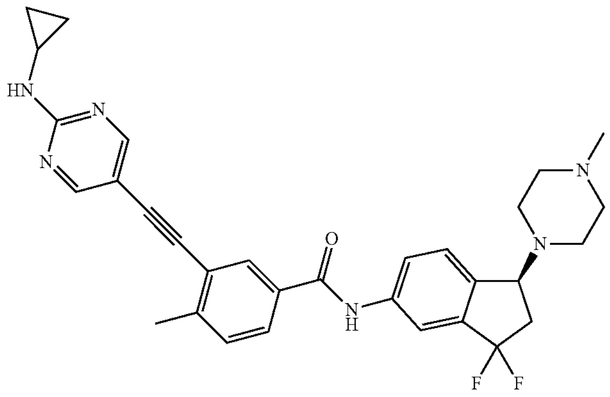 [SMILES: Cc1ccc(C(=O)Nc2ccc3c(c2)C(F)(F)C[C@@H]3N2CCN(C)CC2)cc1C#Cc1cnc(NC2CC2)nc1] | 272.1374* $[M + 2H]^{+2}$* |
| 37-(R) | 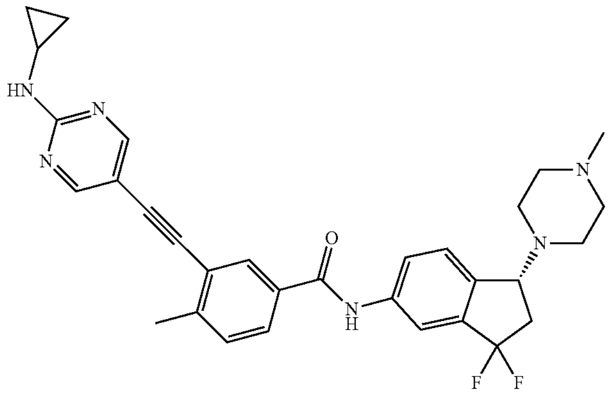 [SMILES: Cc1ccc(C(=O)Nc2ccc3c(c2)C(F)(F)C[C@H]3N2CCN(C)CC2)cc1C#Cc1cnc(NC2CC2)nc1] | 272.1373* $[M + 2H]^{+2}$* |
| 38 | 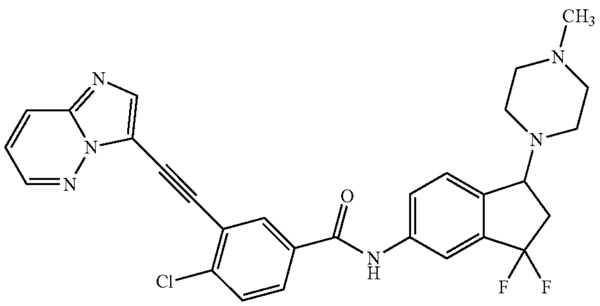 | 274.0962 $[M + 2H]^{+2}$ |
| 38-(S) | 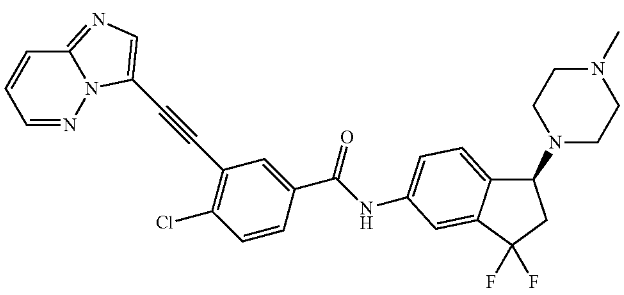 | 274.0949 $[M + 2H]^{+2}$* |

-continued

| Compound | Structure | HR/MS $[M + H]^+$ |
|---|---|---|
| 38-(R) | 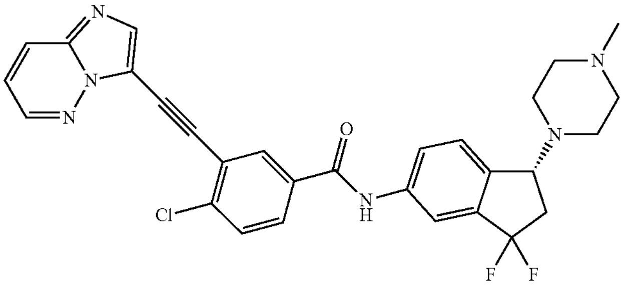 | 274.0944 $[M + 2H]^{+2}$* |
| 39 | 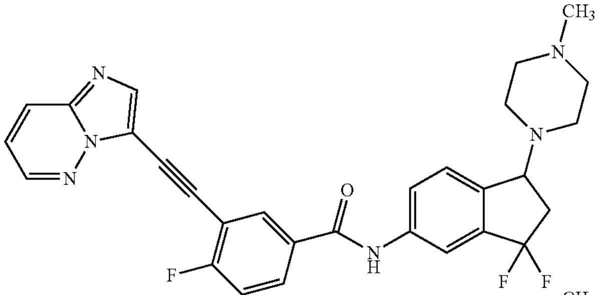 | 531.2120 $[M + H]^{+1}$ |
| 39-(S) | 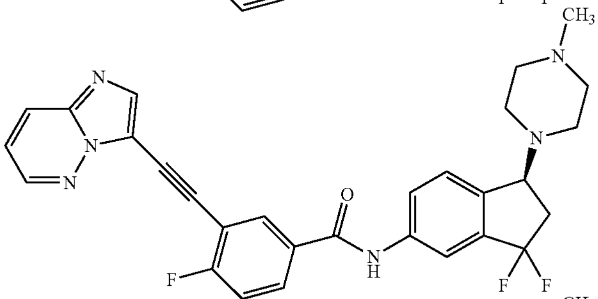 | 531.2122 $[M + H]^{+1}$ |
| 39-(R) | 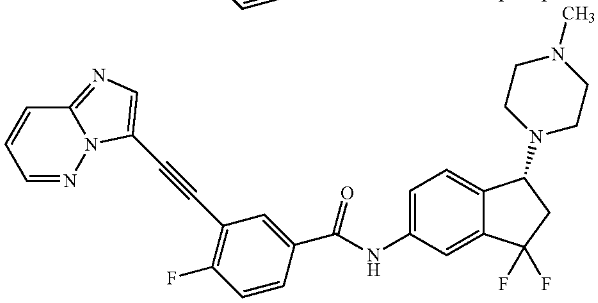 | 531.2125 $[M + H]^{+1}$ |

As used herein unless otherwise indicated, "alkyl" includes branched- and straight-chain saturated aliphatic hydrocarbon groups having the specified carbon atom numbers. Commonly used abbreviations for alkyl groups are used throughout the application, e.g. methyl may be represented by conventional abbreviations including "Me" or $CH_3$ or a symbol that is an extended bond without defined terminal group, e.g.

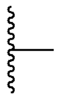

ethyl is represented by "Et" or $CH_2CH_3$, propyl is represented by "Pr" or $CH_2CH_2CH_3$, butyl can be represented by "Bu" or $CH_2CH_2CH_2CH_3$, etc. "$C_{1-6}$ alkyl" (or "$C_1$-$C_6$ alkyl") means branched or linear chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. If no number is provided, 1-10 carbon atoms are intended for linear or branched alkyl groups. $C_{1-6}$ alkyl may be unsubstituted or substituted with 1-3 fluorine or 1-3 chlorine atoms.

"Cycloalkyl" means $C_{3-10}$ carbocycles not containing heteroatoms. For example, cycloalkyl includes cyclopropyl, cyclobutyl, cyclopentyl, cyclohexyl, cycloheptyl, decahydronaphthyl, and the like.

"Aryl" means mono- and bicyclic aromatic rings containing 6-12 carbon atoms. Examples of aryl include, but are not limited to, phenyl, naphthyl, indenyl and so on. Aryl also includes monocyclic rings fused to an aryl group. Examples include tetrahydronaphthyl, indanyl and the like.

"Heterocyclyl", unless otherwise indicated, means a 4-, 5-, 6-, 7- or 8-membered monocyclic saturated ring containing 1-2 heteroatoms selected from N, O and S, in which the point of attachment may be carbon or nitrogen. Examples of "heterocyclyl" include, but are not limited to, piperidinyl, piperazinyl, morpholinyl, azetidinyl, pyrrolidinyl, oxazolidinyl, imidazolidinyl, 2,3-dihydrofuro(2,3-b)pyridyl, benzoxazinyl, and so on. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl may also include such moieties in charged form, e.g., piperidinium.

"Heteroaryl" means a mono- or bicyclic aromatic ring or ring system having 5 to 10 atoms and containing 1-3 heteroatoms selected from N, O, and S. Examples include, but are not limited to, oxadiazolyl, thiadiazolyl, pyrrolyl, furanyl, triazinyl, thienyl, pyrimidyl, pyrimidinyl, pyridazinyl, pyrazinyl, isoxazolyl, triazolyl, isothiazolyl, pyrazolyl, imidazolyl, pyridyl, pyridinyl, oxazolyl, thiazolyl, tetrazolyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, imidazopyridinyl, imidazopyridazinyl, pyrazolopyrazolyl, indazolyl, thienopyrazolyl, pyrazolopyridinyl, and imidazothiazolyl. Heteroaryl also includes such groups in charged form, such as pyridinium. In an embodiment, heteroaryl is imidazolyl, oxadiazolyl, pyrazolyl, oxazolyl, and pyridinyl.

"Heterocyclic alkyl", unless otherwise indicated, includes both branched- and straight-chain saturated aliphatic hydrocarbon groups which is bonded to a carbon or nitrogen atom of a heterocyclyl, as described above.

"Halogen (or halo)" includes fluorine (fluoro), chlorine (chloro), bromine (bromo) and iodine (iodo). In one embodiment, halogen is chlorine or fluorine.

Substitution by a named substituent is permitted on any atom in a ring (e.g., aryl, a heteroaryl ring, or a saturated heterocyclic ring) provided such ring substitution is chemically allowed and results in a stable compound. A "stable" compound can be prepared and isolated, and whose structure and properties remain or can be caused to remain essentially unchanged for a period of time that allows use of the compound for the described purposes.

Under standard nomenclature used throughout this disclosure, the terminal portion of the designated side chain is described first, followed by the adjacent functionality toward the point of attachment. For example, a $C_{1-5}$ alkyl COOR is equivalent to

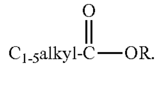

When a variable (e.g., R, $R^x$, etc.) occurs more than once in any constituent or formula, its definition on each occurrence is independent of its definition at every other occurrence. In addition, combinations of substituents and/or variables are allowed only if such combinations lead to stable compounds.

In choosing compounds of the present disclosure, one of ordinary skill in the art will recognize that the various substituents, i.e. $R^1$, $R^2$, R, etc., are to be chosen in conformity with common principles of chemical structure connectivity and stability.

The term "substituted" is used to include multiple degrees of substitution by a named substituent. Where multiple substituents are claimed, the substituted compound can be independently substituted by one or more of the disclosed substituents. By independently substituted, it is meant that the (two or more) substituents can be the identical or different.

Where a substituent or variable has multiple definitions, the substituent or variable is defined as being selected from the group consisting of the indicated definitions.

Isomers: (Optical isomers, diastereoisomers, tautomers, atropisomers, geometric isomers):

Compounds of structural Formula I may contain one or more chiral centers and can occur as racemic mixtures, a single enantiomer, diastereoisomeric mixtures and a single diastereoisomer. The invention contains all such isomeric forms of the compounds covered by Formula I when applicable.

Compounds of structural Formula I may be separated into their individual enantiomers or diastereoisomers by fractional crystallization from a suitable solvent, or via chiral chromatography using an optically active immobile phase. Absolute configuration may be determined by X-ray crystallography of crystalline products or intermediates, or the chirality from vendors who provided chiral material.

Stereoisomers or isomers of a compound of Formula I may be obtained by stereoselective synthesis using optically pure starting materials or reagents of known absolute configuration.

Racemic mixtures of the compounds may be separated by methods well known in the art, such as chrial chromatography, fractional crystallization, the coupling of a racemic mixture of compounds to an enantiomerically pure compound to form a diastereoisomeric mixture, followed by separation of the individual diastereoisomers by chromatography. The coupling reaction may be the formation of salts using an enantiomerically pure acid or base. The diasteromeric derivatives may then be converted to the pure enantiomers by removal of the chiral additives.

Some of the compounds presented in this disclosure may exist as tautomers with different points of attachment of hydrogen accompanied by one or more double bond shifts. For example, a ketone and its enol form are keto-enol tautomers. The individual tautomers as well as mixtures thereof are both covered with compounds of the present invention.

For compounds described herein which contain olefinic double bonds, unless otherwise specified, they include both E and Z olefin isomers.

All atropisomers of compounds covered by Formula I, if applicable, are included in the present application. Atropisomers are stereoisomers resulting from hindered rotation of single bonds where the steric strain barrier to rotation is significant enough to allow for the isolation of the conformers. Separation of atropisomers is possibly by chiral resolution methods such as chiral chromatography or selective crystallization.

In the compounds of Formula I, the atoms may exhibit their natural isotopic abundances. Alternatively, one or more of the atoms may be artificially enriched in a particular isotope having the same atomic number, but an atomic mass different from the atomic mass predominately found in nature. The application includes all suitable isotopic variations of the compounds of Formula I. For example, different isotopic forms of hydrogen (H) include protium ($^1H$) and deuterium ($^2H$, also denoted as D). Enriching for deuterium may afford certain therapeutic advantages, such as increasing metabolic stability, in vivo half-life or reducing dosage requirements, or may provide a compound useful as a standard for characterization of biological samples. Isotopically-enriched compounds within structural Formula I, can be prepared by conventional techniques.

The present invention includes all stereoisomeric forms (as described above), in all ratios, of the compounds of the Formula I.

Salts:

Compounds of structural Formula I also cover the pharmaceutically acceptable salts, and salts that are not pharmaceutically acceptable when they are used as precursors to the free compounds or their pharmaceutically acceptable salts or in salt conversions.

The compounds of the present invention may be administered in the form of a pharmaceutically acceptable salt. The term "pharmaceutically acceptable salt" means salts prepared from pharmaceutically acceptable bases or acids including inorganic or organic bases or acids. Pharmaceutically acceptable salts of basic compounds refer to non-toxic salts of the compounds of this invention which are generally prepared by mixing the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Suitable pharmaceutically acceptable salts of acids covered by Formula I include, but are not limited to, salts generated from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and so on.

If a carboxylic acid (—COOH) or an alcohol is present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be utilized. Included are esters and acyl groups known in the art for modifying the solubility or hydrolysis characteristics for use as controlled-release or prodrug formulations.

If the compounds of Formula I contain both acidic and basic groups in the invention, inner salts or betaines (zwitterions) can be obtained via customary methods known to the person skilled in the art. For example, one can combine an organic or inorganic acid or base in a solvent or dispersant, or by anion exchange or cation exchange from other salts. The present invention also covers all salts of the compounds of Formula I which may not suitable as pharmaceuticals but can be used for the preparation of physiologically acceptable salts.

Solvates and hydrates of the compounds of Formula I are also included in the present invention.

The present invention also discloses processes to synthesize the compounds of Formula I which are described in the following.

One aspect of the invention that is of interest relates to a compound in accordance with Formula I or a pharmaceutically acceptable salt, hydrate, isomer, or solvate thereof for use in a method of treatment of the human by therapy.

Another aspect of the invention relates to a compound in accordance with Formula I or a pharmaceutically acceptable salt, hydrate, isomer, or solvate thereof for use as an anti-cancer agent in a human, wherein said cancer includes, but is not limited to, chronic myeloid leukemia (CML) and acute lymphoblastic leukemia (ALL).

Another aspect of the invention that is of interest is a method of treating inflammations in a human patient in need of such treatment comprising administering a therapeutically effective amount of a compound of Formula I or a pharmaceutically acceptable salt, hydrate, isomer, or solvate thereof.

The present invention also relates to pharmaceutical preparations or pharmaceutical compositions which comprise as active component an effective dose of at least one compound of the Formula I, and/or a physiologically acceptable salt, hydrate, isomer, or solvate thereof, and one or more pharmaceutically acceptable carrier substances and/or additives.

The pharmaceutical compositions based on the invention can be administered orally (e.g. in the form of pills, tablets, granules, hard and soft gelatin capsules, lacquered tablets, sugar-coated tablets, aqueous, syrups, alcoholic or oily solutions, emulsions, suspensions, etc), rectally (e.g. in the form of suppositories), parenterally, subcutaneously, intramuscularly or intravenously (in the form of solutions for injection or infusion), percutaneously or topically (e.g. for example in the form of ointments, tinctures, sprays or transdermal therapeutic systems), or inhalatively (e.g. in the form of nasal sprays or aerosol mixtures, microcapsules, implants or rods). The preferred administration form depends on the progress and severity of disease to be treated.

The compounds of the Formula I and their physiologically acceptable salts, hydrates, isomers, or solvates can be administered to animals, in particular to humans, as pharmaceuticals by themselves, in mixtures with one another or in the form of pharmaceutical preparations. A therapeutically effective amount means that amount of a drug or pharmaceutical agent that will elicit the biological or medical response of a tissue, a system, an animal or a human.

The amount of active compound of the Formula I and/or its physiologically acceptable salts, hydrates, isomers, or solvates in the pharmaceutical preparations normally is from 1 to 2000 mg, preferably from 1 to 500 mg, per dose, but may be higher depending on the type of the pharmaceutical composition. The pharmaceutical preparations typically comprise 0.5 to 90 percent by weight of the compounds of the Formula I and/or their physiologically acceptable salts. One or more compounds of the Formula I and/or their physiologically acceptable salts, together with one or more solid or liquid pharmaceutical carrier substances and/or additives (or auxiliary substances) and, if desired, in combination with other pharmaceutically active compounds having therapeutic action, are formulated in a suitable form which can then be used as a pharmaceutical in human or animal health.

To produce pills, tablets, sugar-coated tablets and hard gelatin capsules, it is possible to use lactose, starch, for example maize starch, or starch derivatives, talc, stearic acid or its salts, etc. Carriers for soft gelatin capsules and suppositories include fats, waxes, semisolid, liquid polyols, natural or hardened oils, etc. Suitable carriers for the preparation of solutions, for example of solutions for injection, or of emulsions or syrups include, for example, water, physiologically sodium chloride solution, alcohols such as ethanol, glycerol, polyols, sucrose, mannitol, vegetable oils, invert sugar, glucose, etc. The compounds of the Formula I and their physiologically acceptable salts may be used to generate lyophilisates, which may be used for preparing preparations for injection or infusion. Suitable carriers for microcapsules, implants or rods are, for example, copolymers of lactic acid and glycolic acid.

Besides active compounds and carriers, the pharmaceutical preparations can also contain customary additives, for example, aromatizers, buffer substances, fillers, diluents, disintegrants, dispersants, binders, colorants, flavorings, emulsifiers, lubricants, preservatives, stabilizers, thickeners, sweeteners, wetting agents, solvents, solubilizers, agents for achieving a depot effect, salts for altering the osmotic pressure, coating agents or antioxidants.

The dosage of the active compound of the Formula I to be administered and/or of a physiologically acceptable salt thereof depends on the individual case, such as the nature and the severity of the disorder to be treated, sex, age, weight and individual responsiveness of the human or animal to be treated, the efficacy and duration of action of the compounds used, whether the therapy is acute or chronic or prophylactic, or whether other active compounds are administered in addition to compounds of the Formula I. In general, a daily dose of approximately 0.01 to 100 mg/kg, preferably 0.3 to 10 mg/kg (in each case mg per kg of bodyweight) is appropriate for administration to an adult to obtain the desired results. The daily dose can be administered in a single dose or multiple doses.

The aforementioned compounds are also of use in combination with other pharmacologically active compounds. Additional active compounds that may be used in combination with the compounds of the instant invention, either co-administered or in a fixed combination, include, but are not limited to anticancer alkylating or intercalating agents, antimetabolites, purine antagonists or pyrimidine antagonists, spindle poisons, podophyllotoxins, antibiotics, nitrosoureas, inorganic ions, enzymes, hormones, mTOR inhibitors, protease inhibitors, NF-kB inhibitor, other inhibitors of kinases (e.g. Src, Brc/Abl, kdr, Flt3, Aurora, GSK-3, EGFR, VEGFR, FGFR, JNK, PKC, CDKs, Syk, JAK, PDGFR, cMET, MEK, AKT, PI3K, c-kit, fit-3, IGFR, ErbB2, etc), antibodies, soluble receptor or other receptor antagonists against a receptor or hormone implicated in a cancer, etc.

Examples of other active ingredients that may be administered in combination with a compound of Formula I, and either administered separately or in the same pharmaceutical composition, include, but are not limited to:

Mechlorethamine, Chlorambucil, Cyclophosphamide, Melphalan, Ifosfamide, Methotrexate, 6-Mercaptopurine, 5-Fluorouracil, Cytarabile, Gemcitabine, Vinblastine, Vincristine, Vinorelbine, Paclitaxel, Etoposide, Irinotecan, Topotecan, Doxorubicin, Bleomycin, Mitomycin, Carmustine, Lomustine, Cisplatin, Carboplatin, Oxaliplatin, Oxiplatin, Asparaginase, Tamoxifen, Leuprolide, Flutamide, Megestrol, Sirolimus, Temsirolimus, Everolimus, AP23573, Velcade, Iressa, Tarceva, Herceptin, Avastin, Erbitux, Zyloprim, Alemtuzmab, Altretamine, Amifostine, Nastrozole, MLN-591, MLN591RL, MLN2704, Arsenic trioxide, Bexarotene, Busulfan, Capecitabine, Gliadel Wafer, Celecoxib, Chlorambucil, Cisplatin-epinephrine gel, Cladribine, Cytarabine liposomal, Daunorubicin liposomal, Daunorubicin, Daunomycin, Dexrazoxane, Docetaxel, Doxorubicin, Elliott's B solution, Epirubicin, Estramustine, Etoposide Phosphate, Etoposide, Exemestane, Fludarabine, 5-FU, Fulvestrant, Gemcitabine, Gemtuzumab-ozogamicin, Goserelin acetate, Hydroxyurea, Idarubicin, Idamycin, Imatinib mesylate, irinotecan, MLN576, Letrozole, Leucovorin, Leucovorin levamisole, melphalan, L-PAM, Mesna, Mitomycin C, Mitoxantrone, Methoxsalen, MLN518, $MLN_{608}$, Itoxantrone, Rituximab, Talc, Temozolamide, Teniposide, VM-26, Topotecan, Pegademase, Pentostatin, Porfimer sodium, 2C4, Tretinoin, ATRA, Valrubicin, Vinorelbine, Pamidronate, Zoledronate.

Furthermore, the invention that is of interest is a method for inhibiting protein kinase comprising administering a therapeutically effective amount of a compound of Formula I, or a salt, hydrate, isomer, or solvate thereof, or a pharmaceutical composition of above described. The protein kinase above mentioned includes, but is not limited to, Bcr-Abl.

The compounds of Formula I can be synthesized in accordance with the general schemes provided below, taking into account the specific examples that are provided. Preferred methods include, but are not limited to those described below. Throughout the synthetic schemes and examples, abbreviations are used with the following meanings unless otherwise indicated:

Ac is acetate, or acetyl;
aq. is aqueous;
AIBN is 2,2'-azobis(2-methylpropionitrile);
Ar is Aryl;
Bn is benzyl;
Boc is tertbutylcarbamoyl;
br is broad;
Bu is butyl;
$^{t}$Bu is tert-butyl;
celite is Celite® diatomaceous earth;
$^{c}$Pr is cyclopropyl;
DCM is dichloromethane;
DIPEA is N,N-diisopropylethylamine;
DMAP is 4-dimethylaminopyridine
DMF is N,N-dimethylformamide;
DMSO is dimethyl sulfoxide;
EDCI is N-(3-dimethylaminopropyl)-N'-ethylcarbodiimide hydrochloride;
EDTA is ethylendiamine tetraacetic acid;
ES-MS is electrospray ion-mass spectroscopy;
Et is ethyl;
$Et_3N$ is triethylaimne;
$Et_2O$ is diethyl ether;
EtOH is ethanol,
EtOAc is ethyl acetate;
halo is a halogen (preferably fluorine or chlorine);
HetAr or HAR is Heteroaryl;
$^{1}$HNMR is proton nuclear magnetic resonance;
HOBt is 1-hydroxybenzotriazole;
HPLC is high performance liquid chromatography;
Hz is hertz;
i is Iso;
kg is kilogram;
LC/MS is Liquid chromatography/Mass Spectroscopy;
M is molar;

Me is methyl;
μg is microgram;
MeCN is acetonitrile;
MeOH is methanol;
MHz is megahertz;
mm is millimeter;
μL is microliter;
mM is milimolar;
μM is micromolar;
mmol is milimoles;
MS is mass spectrum, and a mass spectrum obtained by ES-MS may be denoted herein by "ES";
mw is microwave;
m/z is mass to charge ratio;
n is normal;
NBS is N-bromosuccinimide;
nm is nanometer;
nPr is n-propyl;
p is para;
PE is petroleum;
Ph is phenyl;
Pr is propyl;
rt is room temperature;
sec is secondary;
$^t$Bu is tert-butyl;
$^t$BuOH is tert-butanol;
tert is tertiary;
TBAF is tetrabutylammonium fluoride;
TFA is trifluoroacetic acid;
THF is tetrahydrofuran;
TLC is thin layer chromatography;
TMSA is trimethylsilylacetylene;
TMSOTf is trimethylsilyl trifluoromethanesulfonate;
U is units;
UV is ultraviolet;

SCHEMES

Reaction schemes 1-12 illustrate the methods employed in the synthesis of the compounds of Formula I. All abbreviations are as defined above unless indicated otherwise. In the Schemes, all substituents are as defined above in Formula I unless indicated otherwise.

Synthetic methods for preparing the compounds of the present invention are illustrated in the following Schemes and Examples. Starting materials are commercially available or may be made according to procedures known in the art or as illustrated herein.

SCHEME 1 Preparation of Benzoimidazole Products (1c)

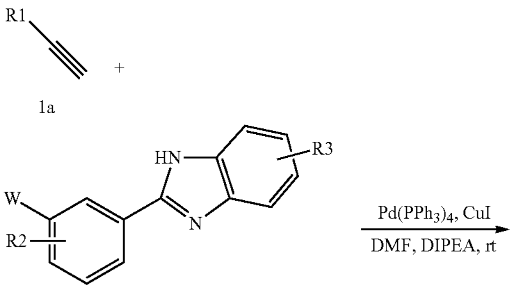

1a

1b

-continued

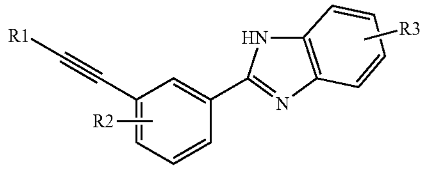

1c

As shown in SCHEME 1, a palladium catalyzed Sonogashira coupling reaction is used to afford the final product 1c. In Scheme 1, the Sonogashira coupling reaction is performed with an acetylenic moiety 1a and a benzimidazole moiety 1b which has been activated by the presence of a reactive group, W, which is an I, a Br or another reactive group permitting the desired coupling reaction.

Several illustrative overall synthetic approaches to the preparation of the acetylenic moieties, based on known transformations, are described below in SCHEME 2 to 4:

SCHEME 2 Preparation of 3-Ethynlimidazol [1,2-b]pyridazine (1a-1)

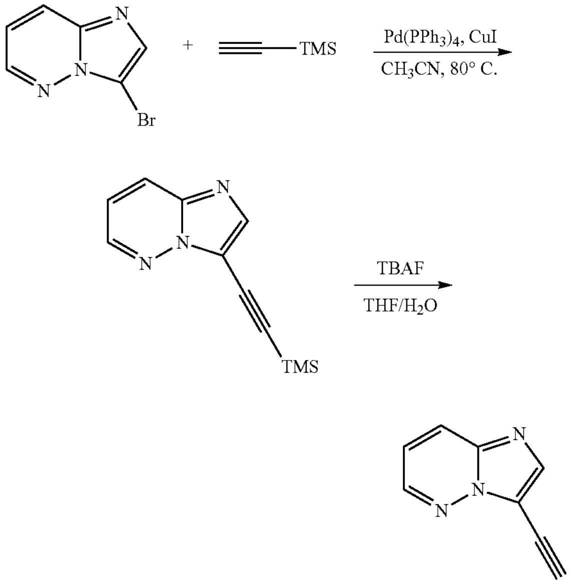

1a-1

SCHEME 3 Preparation of 5-Ethynyl-N-cyclopropylpyrimidin-2-amine

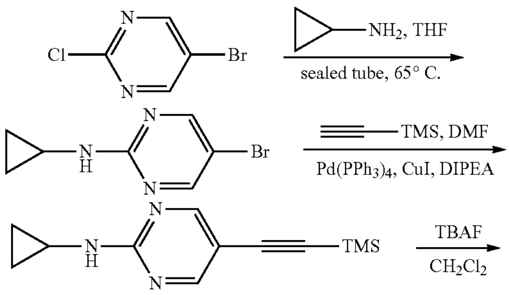

-continued

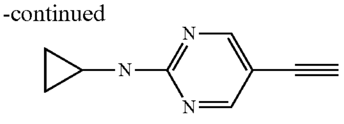

1a-2

SCHEME 4 Preparation of 6-Ethynyl-N-substitued-pyridazin-2-amine (1a-3 to 1a-5)

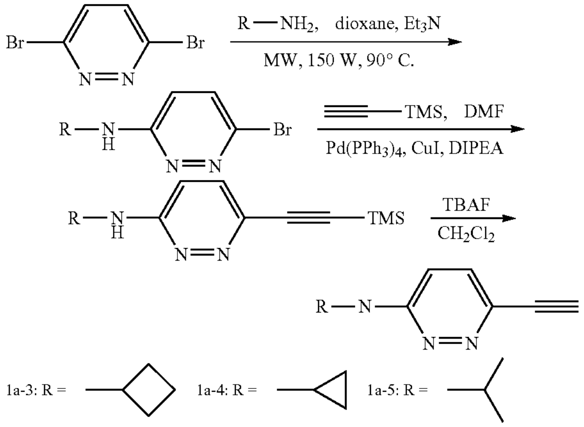

SCHEME 5 to 6 below depict the synthesis of some representative benzoimidazole compounds of the formula 1b which are useful as intermediates in the coupling reaction described in SCHEME 1.

SCHEME 5 describes an illustrative synthesis of the formula 1b-1 and 1b-2 in which R3 is (4-methylpiperazin-1-yl) methyl, and R2 is methyl and chloro respectively.

SCHEME 5

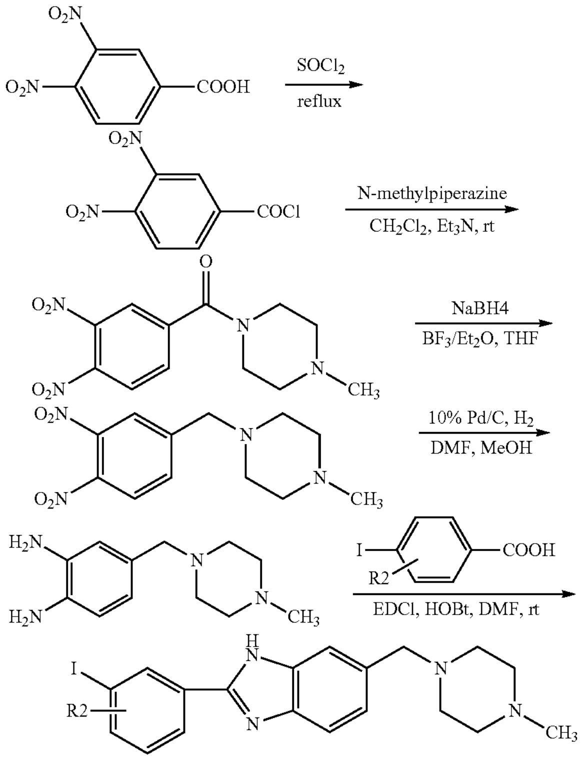

1b-1:R2 = $CH_3$
1b-2:R2 = Cl

SCHEME 6 describes an illustrative synthesis of the formula 1b-3 in which R3 is 4-methyl-1H-imidazol-1-yl, and R2 is methyl.

SCHEME 6

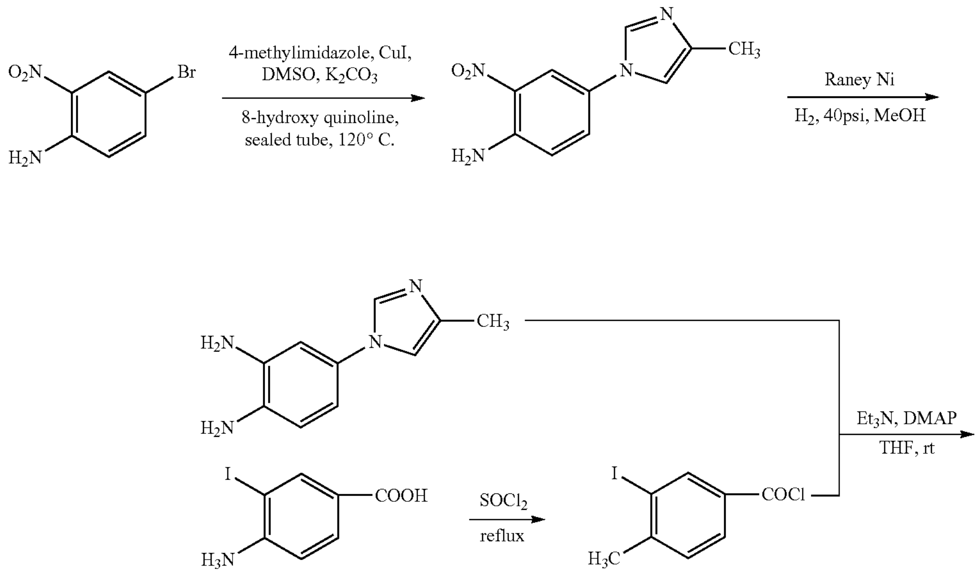

-continued

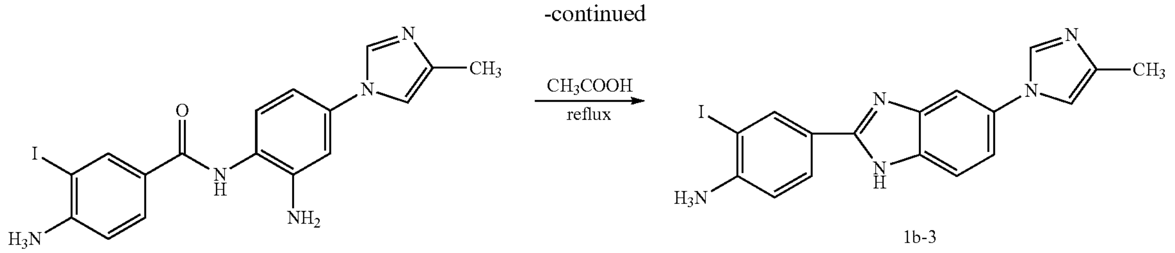

1b-3

SCHEME 7 Preparation of Benzoimidazole Products (2c)

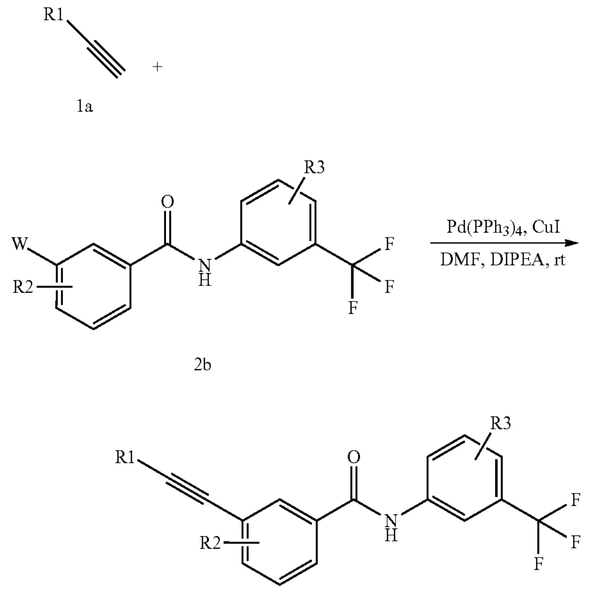

1a

2b

2c

Like SCHEME 1, in SCHEME 7, an acetylenic moiety 1a condensed with a benzamide moiety 2b through the Sonogashira coupling reaction to afford benzamide analogs 2c.

SCHEME 8 to 10 below depict the synthesis of some representative benzamide compounds of the formula 2b which are useful as intermediates in the coupling reaction described in SCHEME 1.

SCHEME 8 and 9 depict the synthesis of 2b in which R3 is 4-methyl-1H-imidazol-1-yl, R2 is methyl or chloro group respectively. Some representative intermediates include following structures:

2b-1

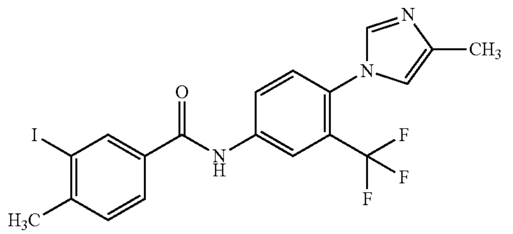

-continued 2b-2

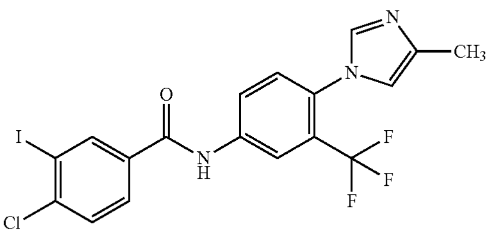

2b-3

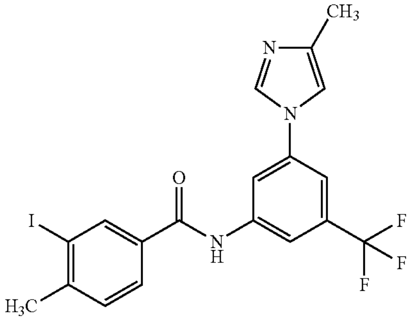

2b-4

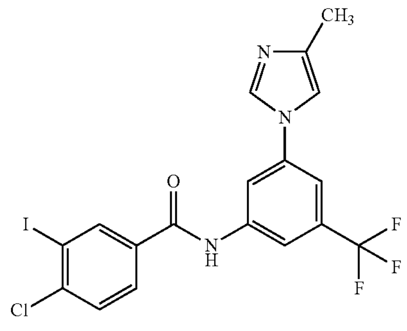

SCHEME 8
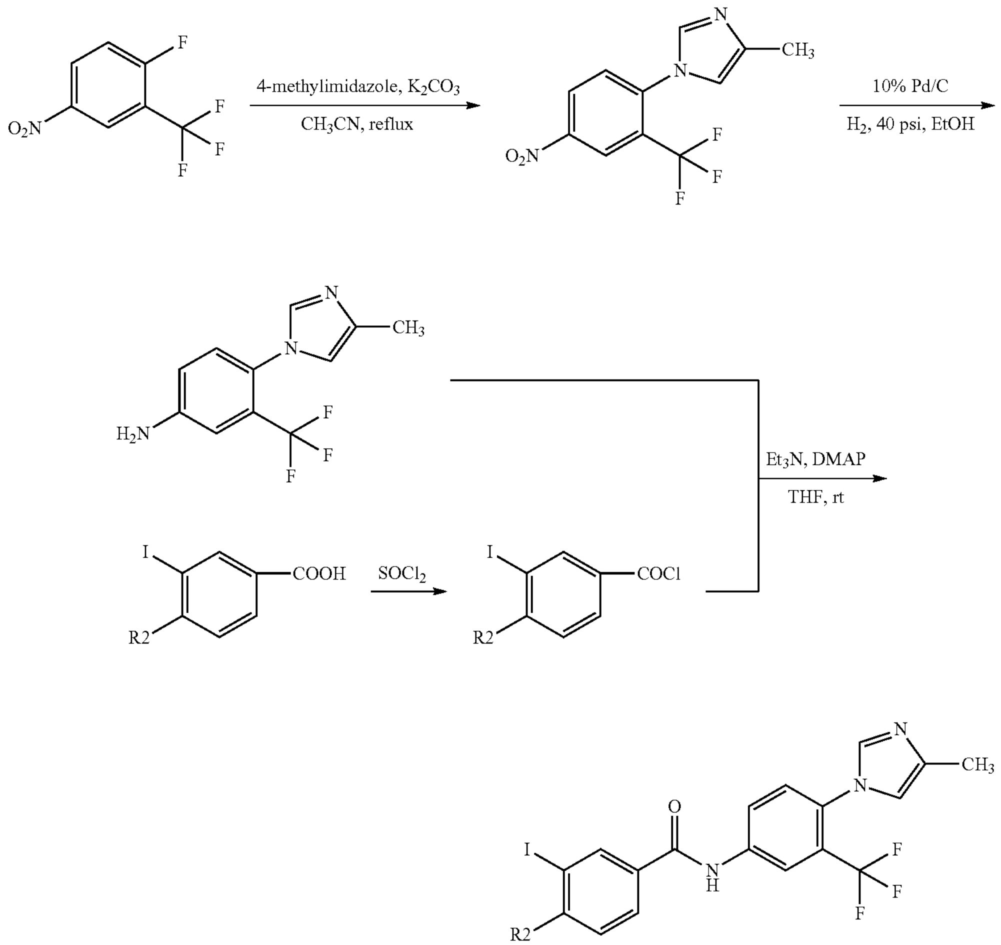
2b-1: R2 = $CH_3$ 2b-2: R2 = Cl
SCHEME 9
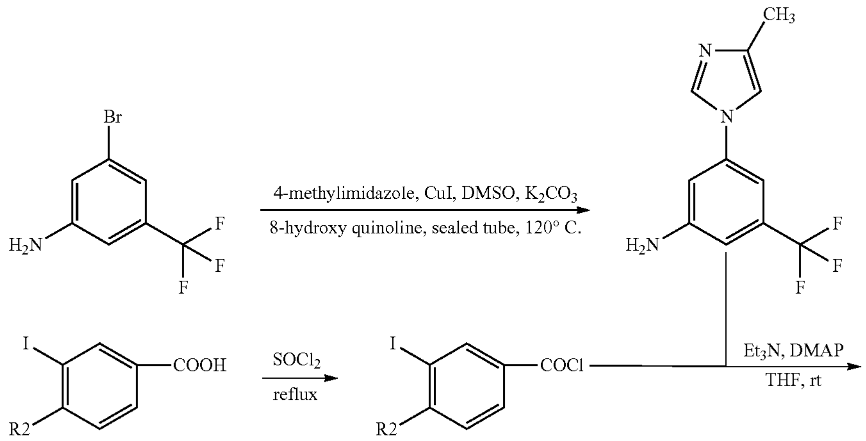

-continued
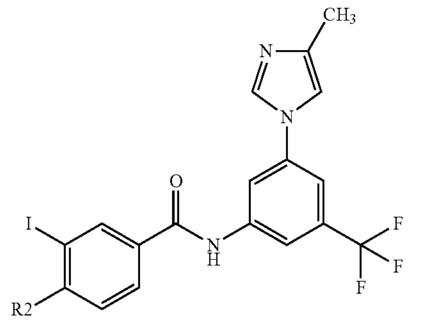
2b-3:R2 = $CH_3$
2b-4:R2 = Cl
SCHEME 10 decribes the synthesis of 2b in which R3 is (4-methylpiperazin-1-yl)methyl, R2 is methyl or chloro group respectively.
SCHEME 10
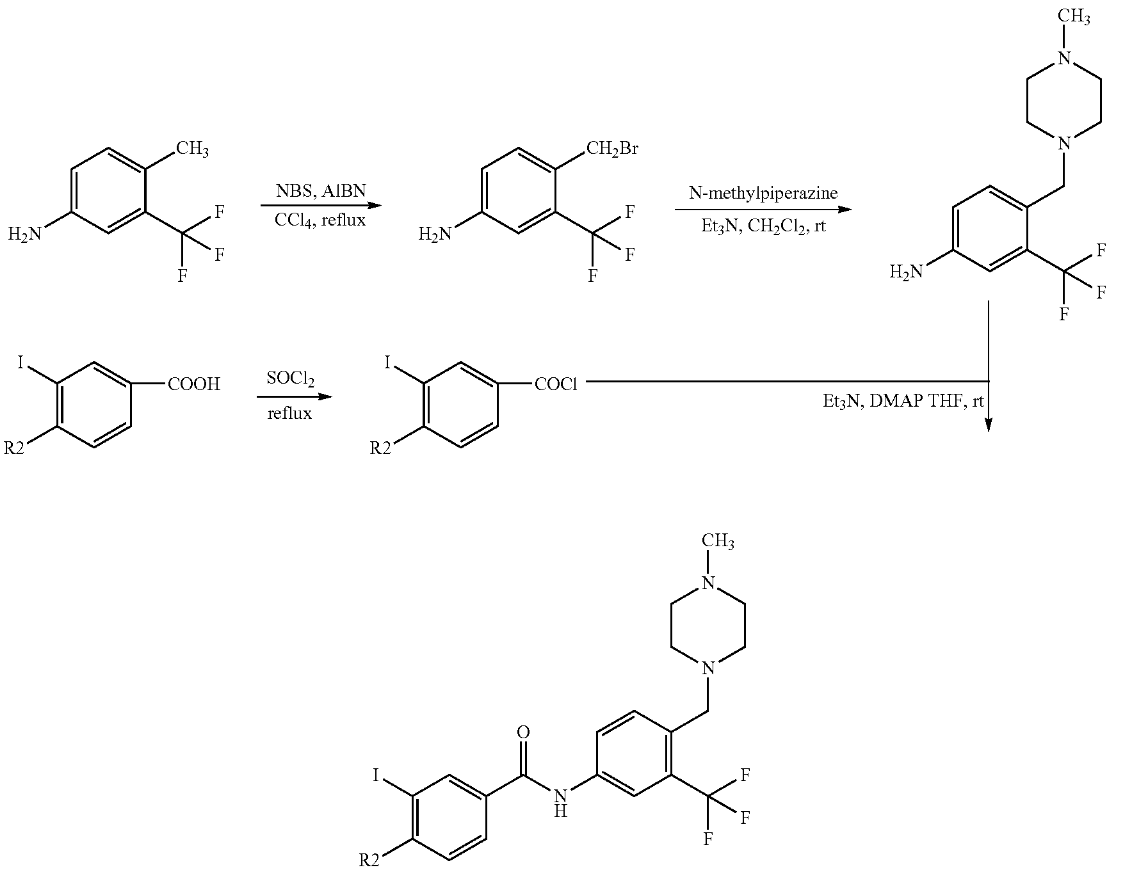
2b-5:R2 = $CH_3$
2b-6:R2 = Cl SCHEME 11 Preparation of Urea Products (3c)

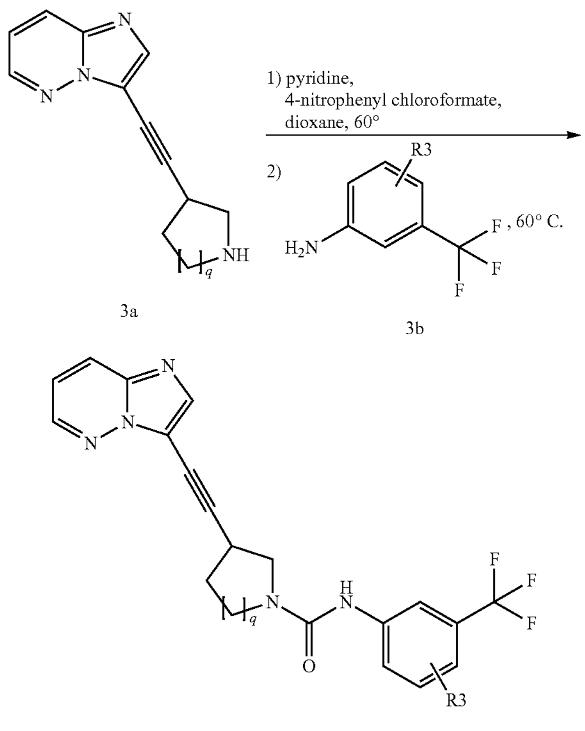

3a 3b

3c q = 1 or 2

As shown in SCHEME 11, an amine containing acetyl moiety 3a condensed with a substituted aromatic amine moiety 3b to afford urea analogs 3c.

SCHEME 12 below depicts the synthesis of some representative compounds of the formula 3a which are useful as intermediates in the condensation reaction described in SCHEME 11. The synthesis of aromatic amine compounds of the formula 3b has been described in SCHEME 8 to 10 for the synthesis of 2b-1 to 2b-6.

SCHEME 12

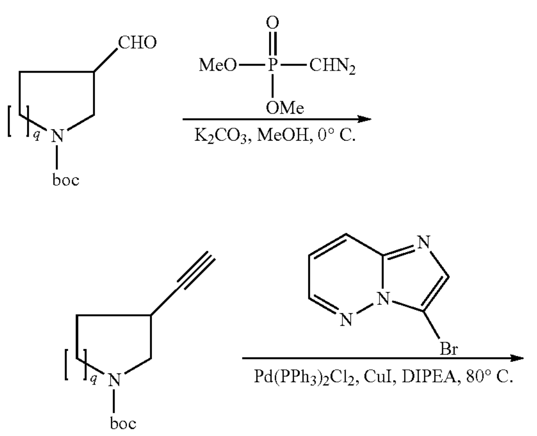

-continued

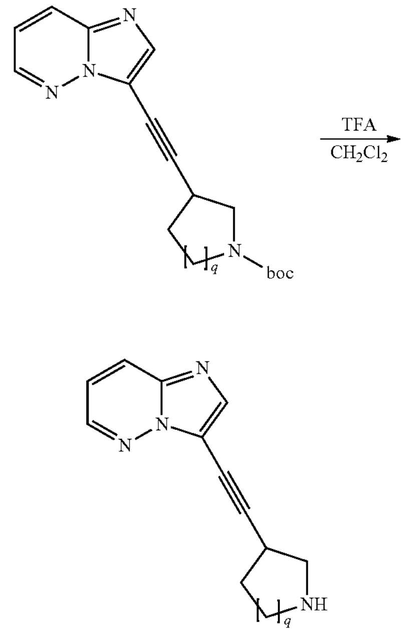

3a-1: q = 1
3a-2: q = 2

SCHEME 13 Preparation of Bicyclic Benzamide Products (4c)

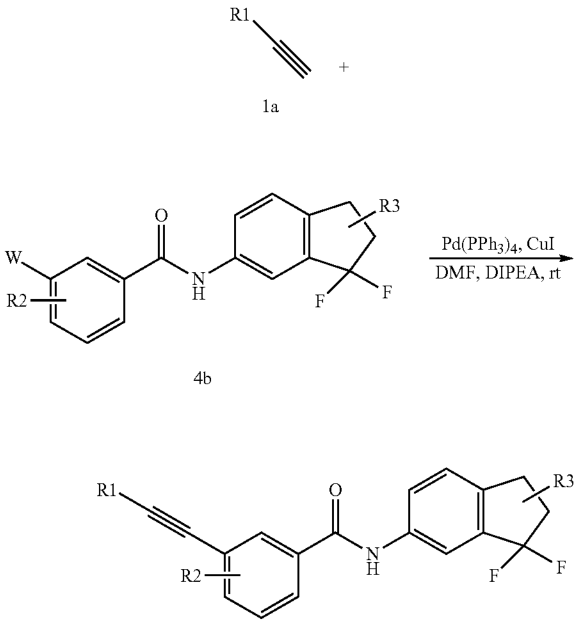

1a

4b

4c

Like SCHEME 1, in SCHEME 13, an acetylenic moiety 1a condensed with a benzamide moiety 4b through the Sonogashira coupling reaction to afford benzamide analogs 4c.

SCHEME 14 decribes the synthesis of 4b in which R3 is (4-methylpiperazin-1-yl)methyl, and R2 is methyl.

SCHEME 14
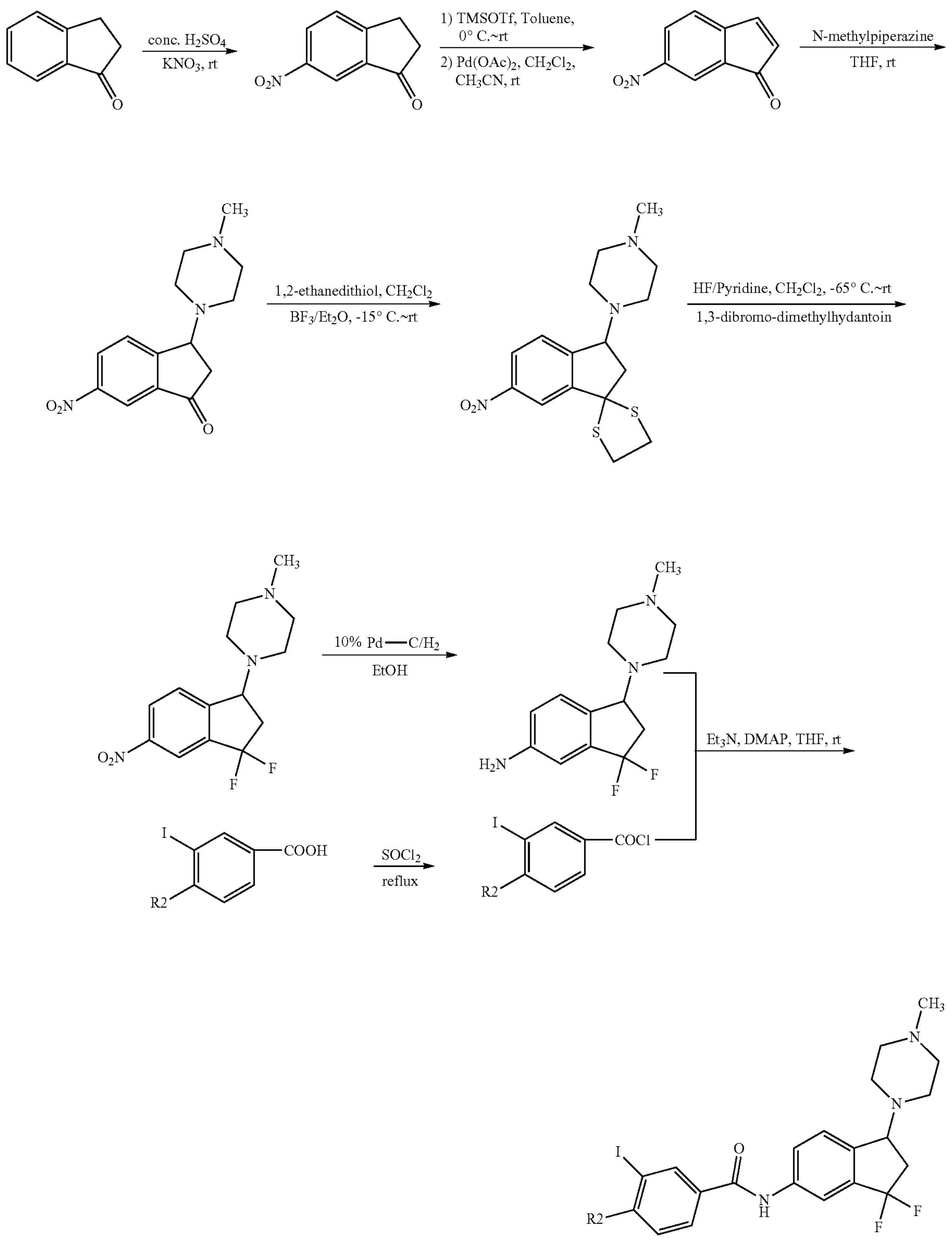
4b

EXAMPLES

The following representative examples are intended to help illustrate the invention, and are not intended to, nor should they be constructed to limit its scope.

Example 1

N-Cyclobutyl-6-(2-(2-methyl-5-(6-((4-methylpiperazin-1-yl)methyl)-1H-benzo[d]imidazol-2-yl)phenyl)ethynyl)pyridazin-3-amine

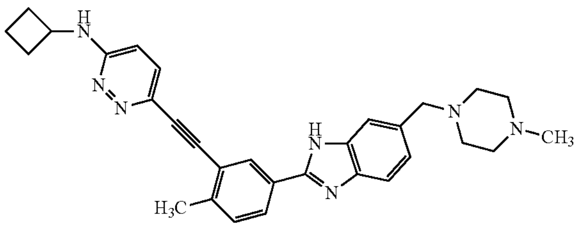 [SMILES: Cc1ccc(-c2nc3ccc(CN4CCN(C)CC4)cc3[nH]2)cc1C#Cc1ccc(NC2CCC2)nn1]

Step 1. 6-Bromo-N-cyclobutylpyridazin-3-amine

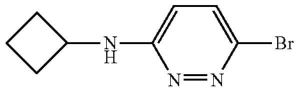

Into a solution of 3,6-dibromopyridazine (1.19 g, 5 mmol) in dioxane (5 mL) was added cyclobutylamine (0.39 g, 5.5 mmol), and $Et_3N$ (0.60 g, 6 mmol). The reaction was microwave at 90° C., 150W for 0.45 h. The reaction was monitored by TLC and the crude product was purified by silica gel chromatography (eluent: 30% Ethyl acetate in n-hexane), to give the desired product (0.63 g, 55.3%). $^1H$ NMR (300 MHz, $CDCl_3$) δ: 7.25-7.28 (1 H, d, J=9.0 Hz), 6.49-6.52 (1 H, d, J=9.0 Hz), 5.27 (1 H, s), 4.16-4.24 (1 H, m), 2.40-4.49 (2 H, m), 1.87-1.95 (2 H, m), 1.75-1.84 (2 H, m).

Step 2. N-Cyclobutyl-6-(2-(trimethylsilyl)ethynyl)pyridazin-3-amine

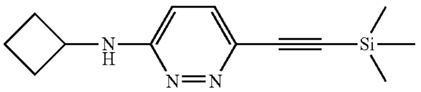 [SMILES: C[Si](C)(C)C#Cc1ccc(NC2CCC2)nn1]

6-Bromo-N-cyclobutylpyridazin-3-amine (0.60 g, 2.63 mmol), trimethylsilylacetylene (TMSA) (1.29 g, 13.1 mmol), $Pd(PPh_3)_4$ (0.15 g), and CuI (0.04 mg) were placed in a vial with a rubber septum. After the mixture underwent 3 cycles of vacuum/filling with $Ar_2$, DMF (3.0 mL) and N,N-diisopropylethylamine (DIPEA) (0.41 g, 3.2 mmol) were added. The mixture was then stirred at 80° C. for 16 hrs. The reaction mixture was concentrated and the resulting residue was purified by silica gel chromatography (eluent: 30% ethyl acetate in n-hexane, ethyl acetate was added 0.5% $Et_3N$) to give an off-white solid (0.48 g, 74.5%). $^1H$ NMR (300 MHz, $CDCl_3$) δ: 7.26-7.29 (1 H, d, J=9.0 Hz), 6.50-6.53 (1 H, d, J=9.0 Hz), 5.55 (1 H, s), 4.17-4.24 (1 H, m), 2.40-2.46 (2 H, m), 1.89-1.98 (2 H, m), 1.77-1.85 (2 H, m), 0.28 (9 H, s).

Step 3. N-Cyclobutyl-6-ethynylpyridazin-3-amine

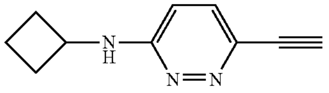

Into a solution of N-cyclobutyl-6-(2-(trimethylsilypethynyl)pyridazin-3-amine (0.49 g, 2 mmol) in $CH_2Cl_2$, TBAF was added. The reaction was monitored by TLC. The reaction mixture was concentrated and the residue obtained was purified by silica gel chromatography (eluent: 30% ethyl acetate in n-hexane, ethyl acetate was added 0.5% $Et_3N$) to give an off-white solid (0.26 g, 75.1%). $^1H$ NMR (300 MHz, $CDCl_3$) δ: 7.26-7.29 (1 H, d, J=9.0 Hz), 6.51-6.54 (1 H, d, J=9.0 Hz), 5.57 (1 H, s), 4.17-4.24 (1 H, m), 3.21 (1 H, s), 2.40-2.46 (2 H, m), 1.89-1.98 (2 H, m), 1.77-1.85 (2 H, m).

Step 4. (3,4-Dinitrophenyl)-(4-methylpiperazin-1-yl)-methanone

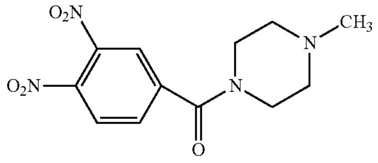 [SMILES: CN1CCN(C(=O)c2ccc([N+](=O)[O-])c([N+](=O)[O-])c2)CC1]

A mixture of 3,4-dinitrobenzoic acid (10.6 g, 50 mmol) and $SOCl_2$ (50 mL) was heated at reflux for 6 hrs. Then the mixture was evaporated to dryness in vacuo. The residue was dissolved in $CH_2Cl_2$ (50 mL) and cooled to 5° C. To this solution, N-methylpiperazine (5.5 g, 55 mmol) and $Et_3N$ (5.5 g, 55 mmol) were added dropwise as a solution in $CH_2Cl_2$ (50 mL). After stirring overnight at rt, the combined organic phase was washed with water (100 mL), dried over $Na_2SO_4$, filtered and concentrated, the resulting residue was purified by silica gel chromatography (eluent: 5% MeOH in $CH_2Cl_2$) to give a yellow solid (14.0 g, 95.2%). $^1H$ NMR (300 MHz, DMSO-$d_6$) δ: 8.29 (1 H, s), 8.25-8.27 (1 H, d, J=9.0 Hz), 7.95-7.98 (1 H, d, J=9.0 Hz), 3.62 (2 H, m), 3.28 (2 H, m), 2.38 (2 H, m), 2.26 (2 H, m), 2.19 (3 H, s).

Step 5. 1-(3,4-Dinitrobenzyl)-4-methylpiperazine

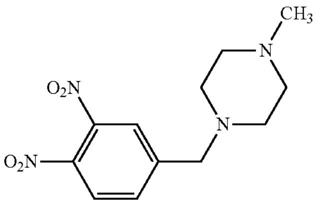

To a cooled solution (−5° C.) of (3,4-dinitrophenyl)-(4-methylpiperazin-1-yl)methanone (5.88 g, 20 mmol) in THF, was added powdered $NaBH_4$ (1.89 g, 50 mmol), followed by the dropwise addition of $BF_3.OEt_2$ (6.4 mL, 50 mmol), while keeping the temperature below 5° C. The mixture was allowed to come to room temperature over 2 hrs, and then stirred for a further 3 hrs at room temperature. MeOH was then added cautiously to the mixture, the stirring was continued for 10 minutes and then the mixture was concentrated. The residue was partitioned between EtOAc (150 mL) and saturated aqueous $NaHCO_3$ (150 mL). The organic layer was washed with water (100 mL), brine (100 mL) and then dried by $Na_2SO_4$, filtered and concentrated. The residue was purified by silica gel chromatography (eluent: 2% MeOH in $CH_2Cl_2$) to give a yellow solid (4.5 g, 80.3%). $^1$H NMR (300 MHz, $CDCl_3$) δ: 7.90-7.92 (1 H, d, J=6.0 Hz), 7.90 (1 H, s), 7.69-7.71 (1 H, d, J=6.0 Hz), 3.73 (2 H, s), 3.07-3.10 (2 H, m), 2.94-2.99 (2 H, m), 2.76-2.81 (2 H, m), 2.67 (3 H, s), 2.53-2.56 (2 H, m).

Step 6. 1-(3,4-Diaminobenzyl)-4-methylpiperazine

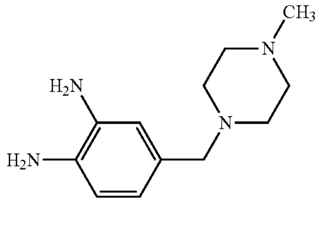 [SMILES: CN1CCN(Cc2ccc([N+](=O)[O-])c([N+](=O)[O-])c2)CC1]

1-(3,4-Dinitrobenzyl)-4-methylpiperazine (2.8 g, 10 mmol), was dissolved in DMF:MeOH (1:1, 20 mL) and agitated with 10% Pd/C (280 mg) under an atmosphere of $H_2$ for 12 hrs. The reaction was monitored by TLC. The mixture was then filtered and evaporated to give a dark solid which was used immediately without any further purification.

Step 7. 2-(3-Iodo-4-methylphenyl)-6-((4-methylpiperazin-1-yl)methyl)-1H-benzo[d]imidazole

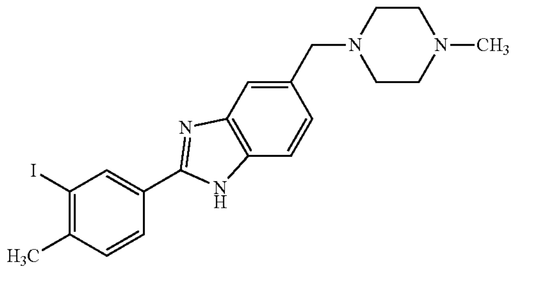 [SMILES: Cc1ccc(-c2nc3cc(CN4CCN(C)CC4)ccc3[nH]2)cc1I]

A mixture of 1-(3,4-diaminobenzyl)-4-methylpiperazine (10 mmol), 3-iodo-4-methylbenzoic acid (2.6 g, 10 mmol), EDCI (11 mmol), and HOBt (11 mmol) in dry DMF (25 mL) was stirred at ambient temperature for 24 hrs. The mixture was then evaporated in vacuo and the crude residue was dissolved in $CH_2Cl_2$ (100 mL) was washed with water (100 mL), brine (100 mL) and then dried by $Na_2SO_4$, filtered and concentrated. The residue obtained was dissolved in AcOH (30 mL) and heated at reflux for 3 hrs. The reaction mixture was eavporated in vacuo and the residue was purified by silica gel chromatography (eluent: 10% MeOH in $CH_2Cl_2$, MeOH was added 0.5% $Et_3N$) to give a yellow solid (1.35 g, 30.3%). $^1$H NMR (300 MHz, $CDCl_3$) δ: 8.50 (1 H, s), 7.94-7.97 (1 H, d, J=9.0 Hz), 7.53-7.56 (1 H, d, J=9.0 Hz), 7.52-7.55 (1 H, d, J=9.0 Hz), 7.30 (1 H, s), 7.20-7.23 (1 H, d, J=9.0 Hz), 3.60 (2 H, s), 2.54 (8 H, brs), 2.45 (3 H, s), 2.32 (3 H, s).

Step 8

N-Cyclobutyl-6-(2-(2-methyl-5-(6-((4-methylpiperazin-1-yl)methyl)-1H-benzo[d]imidazol-2-yl)phenyl)ethynyl)pyridazin-3-amine N-Cyclobutyl-6-ethynylpyridazin-3-amine (62 mg, 0.36 mmol), 2-(3-iodo-4-methylphenyl)-6-((4-methylpiperazin-1-yl)methyl)-1H-benzo[d]imidazole (134 mg, 0.3 mmol), $Pd(PPh_3)_4$ (18 mg, 0.015 mmol) and CuI (4.3 mg, 0.023 mmol) were placed in a two neck flask with a rubber plug. The mixture underwent 3 cycles of vacuum and filling with $Ar_2$, a solution of DIPEA (58 mg, 0.45 mmol) and DMF (2 mL) was injected to the flask. The mixture was stirred at rt for 20 hrs, and then was poured into 25 mL water, extracted with $CH_2Cl_2$ (20 mL×3), organic layer was washed with brine, dried with $Na_2SO_4$, filtered, and the filtrate was evaporated in vacuo. The residue was purified by chromatography on silica gel ($CH_2Cl_2$/$CH_3OH$ 97:3 to 97:6) to give 0.12 g crude product, continue to purify via preparation TLC ($CH_2Cl_2$/$CH_3OH$ 120:8) to give 87 mg product as a pale yellow solid. Mp:148-150° C.; $^1$H NMR (300 MHz, $CDCl_3$) δ: 8.07-8.10 (1 H, d, J=9.0 Hz), 7.90 (1 H, s), 7.63-7.66 (1 H, d, J=9.0 Hz), 7.63 (1 H, s), 7.26-7.24 (1 H, d, J=6.0 Hz), 7.20 (1 H, m), 7.15 (1 H, m), 6.60-6.63 (1 H, d, J=9.0 Hz), 5.63 (1 H, s), 4.26-4.33 (1 H, m), 3.62 (2 H, s), 2.58 (8 H, brs), 2.35 (3 H, s), 2.31 (3 H, s), 1.94-2.03 (2 H, m), 1.82-1.85 (2 H, m). HRMS (ESI-TOF$^+$): m/z $[M+H]^+$ calcd for $C_{30}H_{34}N_7$: 492.2870. found: 492.2856.

Example 2

N-Cyclopropyl-6-(2-(2-methyl-5-(6-((4-methylpiperazin-1-yl)methyl)-1H-benzo[d]imidazol-2-yl)phenyl)ethynyl)pyridazin-3-amine

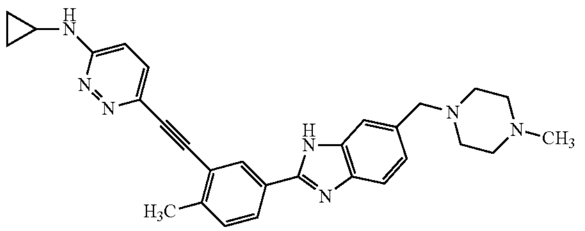 [SMILES: Cc1ccc(-c2nc3ccc(CN4CCN(C)CC4)cc3[nH]2)cc1C#Cc1ccc(NC2CC2)nn1]

The title compound was synthesized from N-cyclopropyl-6-ethynylpyridazin-3-amine and 2-(3-iodo-4-methylphenyl)-6-((4-methylpiperazin-1-yl)methyl)-1 H-benzo[d]imidazole (as prepared in Example 1) in a manner similar to that described for in Example 1. The intermediate compound N-cyclopropyl-6-ethynylpyridazin-3-amine was made as for Example 1 (Step 1 to 3) with the spectra below: $^1$H NMR (300 MHz, $CDCl_3$) δ: 7.38-7.41 (1 H, d, J=9.0 Hz), 6.96-6.99 (1 H, d, J=9.0 Hz), 5.99 (1 H, s), 3.25-3.27 (1 H, m), 2.57 (1 H, s), 0.87-0.89 (2 H, s), 0.61-0.63 (2 H, s).

The title compound was obtained as as a khaki solid. Mp:145-146° C.; $^1$H NMR (300 MHz, $CDCl_3$) δ: 8.14 (1 H, s), 8.11-8.13 (1 H, d, J=6.0 Hz), 7.64 (2 H, m), 7.37-7.40 (1 H, d, J=9.0 Hz), 7.21-7.24 (1 H, d, J=9.0 Hz), 7.14-7.17 (1 H, d, J=7.0 Hz), 7.01-7.04 (1 H, d, J=9.0 Hz), 6.19 (1 H, s), 3.67 (2 H, s), 2.74 (8 H, brs), 2.58 (1 H, m), 2.50 (3 H, s), 2.34 (3 H, s), 0.84-0.87 (2 H, m), 0.64 (2 H, m); HRMS (ESI-TOF$^+$): m/z $[M+H]^+$ calcd for $C_{29}H_{32}N_7$: 478.2714. found: 478.2708.

Example 3

3-(2-(2-Methyl-5-(6-((4-methylpiperazin-1-yl)methyl)-1H-benzo[d]imidazol-2-yl)phenyl)ethynyl)imidazo[1,2-b]pyridazine

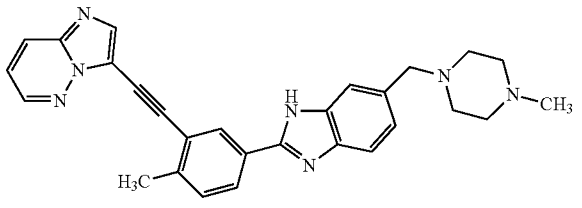

The title compound was synthesized from 3-ethynylimidazo[1,2-b]pyridazine and 2-(3-iodo-4-methylphenyl)-6-((4-methylpiperazin-1-yl)methyl)-1 H-benzo[d]imidazole (as prepared in Example 1) in a manner similar to that described for in Example 1. The intermediate compound 3-ethynylimidazo[1,2-b]pyridazin was made as for Example 1 (Step 1 to 3) with the spectra below: $^1$H NMR (300 MHz, DMSO-$d_6$) δ: 8.63-8.64 (1 H, m), 8.18-8.21 (1 H, m), 8.10 (1 H, s), 7.32-7.35 (1 H, m), 4.94 (1 H, s).

The title compound was obtained as a pale yellow solid. Mp:114-115° C.; $^1$H NMR (300 MHz, $CDCl_3$) δ: 8.46-8.48 (1 H, d, J=6.0 Hz), 8.25 (1 H, s), 8.15 (1 H, s), 8.09-8.12 (1 H, d, J=9.0 Hz), 7.96-7.99 (1 H, d, J=9.0 Hz), 7.59 (1 H, s), 7.35-7.37 (1 H, d, J=9.0 Hz), 7.26 (1 H, s), 7.22 (1 H, s), 7.10-7.15 (1 H, m), 3.64 (2 H, s), 2.60 (8 H, brs), 2.58 (3 H, s), 2.34 (3 H, s). HRMS (ESI-TOF$^+$): m/z $[M+H]^+$ calcd for $C_{28}H_{28}N_7$: 462.2401. found: 462.2413.

Example 4

N-Isopropyl-6-(2-(2-methyl-5-(6-((4-methylpiperazin-1-yl)methyl)-1H-benzo[d]imidazol-2-yl)phenyl)ethynyl)pyridazin-3-amine

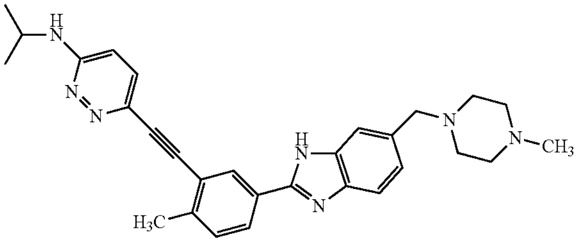 [SMILES: Cc1ccc(-c2nc3ccc(CN4CCN(C)CC4)cc3[nH]2)cc1C#Cc1ccc(NC(C)C)nn1]

The title compound was synthesized from N-isopropyl-6-ethynylpyridazin-3-amine and 2-(3-iodo-4-methylphenyl)-6-((4-methylpiperazin-1-yl)methyl)-1H-benzo[d]-imidazole (as prepared in Example 1) in a manner similar to that described for in Example 1. The intermediate compound N-isopropyl-6-ethynylpyridazin-3-amine was made as for Example 1 (Step 1 to 3) with the spectra below: $^1$H NMR (300 MHz, $CDCl_3$) δ: 7.26-7.29 (1 H, d, J=9.0 Hz), 6.54-6.57 (1 H, d, J=9.0 Hz), 5.00 (1 H, s), 3.97-4.04 (1 H, m), 3.25 (1 H, s), 1.29 (3 H, s), 1.27 (3 H, s).

The title compound was obtained as a pale yellow solid. Mp:129-130° C.; $^1$H NMR (300 MHz, $CDCl_3$) δ: 8.06-8.08 (1 H, d, J=6.0 Hz), 7.87 (1 H, s), 7.65 (2 H, m), 7.27 (1 H, s), 7.25 (1 H, s), 7.19-7.21 (1 H, d, J=9.0 Hz), 6.61-6.64 (1 H, d, J=9.0 Hz), 5.01-5.04 (1 H, d, J=9.0 Hz), 4.11-4.15 (1 H, m), 3.61 (2 H, s), 2.43 (8H, brs), 2.32 (3 H, s), 2.27 (3 H, s), 1.25-1.32 (6 H, m). HRMS (ESI-TOF$^+$): m/z $[M+H]^+$ calcd for $C_{29}H_{34}N_7$: 480.2870. found: 480.2847.

Example 5

N-Cyclopropyl-5-(2-(2-methyl-5-(6-((4-methylpiperazin-1-yl)methyl)-1H-benzo[d]imidazol-2-yl)phenyl)ethynyl)pyrimidin-2-amine

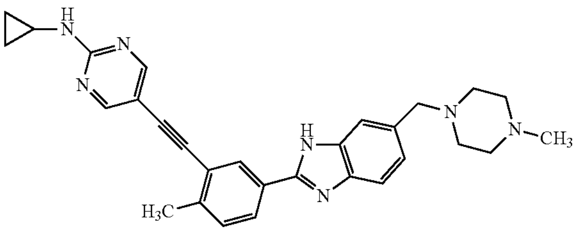 [SMILES: Cc1ccc(-c2nc3ccc(CN4CCN(C)CC4)cc3[nH]2)cc1C#Cc1cnc(NC2CC2)nc1]

Step 1. 5-Bromo-N-cyclopropylpyrimidin-2-amine

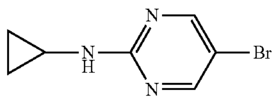 [SMILES: Brc1cnc(NC2CC2)nc1]

A solution of 5-bromo-2-chloropyrimidine (3.87 g, 20 mmol) and cyclopropylamine (5.7 g, 0.1 mol) in 20 mL THF was heated at 65° C. for 5 hrs in a sealed tube. The mixture was evaporated in vacuo, to the residue ethanol was added, after filtration, the cake was washed with ethanol to give 4.07 g product as a colorless solid (95.5%). $^1$H NMR (300 MHz, $CDCl_3$) δ: 8.32 (2 H, s), 5.58 (1 H, brs), 2.72 (1 H, brs), 0.82-0.84 (2 H, m), 0.54 (2 H, brs). LCMS: m/z $[M+H]^+$ 214.0011.

Step 2. N-Cyclopropyl-5-ethynylpyrimidin-2-amine

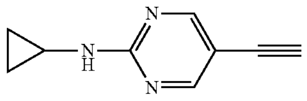

5-Bromo-N-cyclopropylpyrimidin-2-amine (1.06 g, 5 mmol), trimethylsilylacetylene (2.5 g, 25 mmol), $Pd(PPh_3)_4$ (289 mg, 0.25 mmol) and CuI (71 mg, 0.375 mmol) were placed in a two neck flask with a rubber plug. The mixture underwent 3 cycles of vacuum and filling with $Ar_2$, a solution of DIPEA (968 mg, 0.45 mmol) and DMF (10 mL) was injected to the flask. The mixture was stirred at 80° C. for 15 hrs, and then was poured into 50 mL water, extracted with EtOAc (30 mL×3), organic layer was washed with brine, dried with $Na_2SO_4$, filtered, and the filtrate was evaporated in vacuo. The residue was purified by chromatography on silica gel (PE/EtOAc 82:18 to 64:36) to give 1.1 g N-cyclopropyl-5-(2-(trimethylsilyl)ethynyl)pyrimidin-2-amine. This compound was dissolved in 20 mL $CH_2Cl_2$, a solution of TBAF (1.3 g, 5 mmol) in 10 mL $CH_2Cl_2$ was added into the above solution. The mixture was stirred at rt for 1 h, evaporated in vacuo. The residue was purified by chromatography on silica gel (PE/EtOAc 82:18 to 64:36) to give 0.55 g product as a pale yellow solid (72.8%). $^1$H NMR (300 MHz, $CDCl_3$) δ: 8.43 (2 H, s), 5.77 (1 H, brs), 3.18 (1 H, s), 2.76-2.81 (1 H, m), 0.82-0.87 (2 H, m), 0.54-0.59 (2 H, m). LCMS: m/z $[M+H]^+$ 160.0863.

Step 3

N-Cyclopropyl-5-(2-(2-methyl-5-(6-((4-methylpiperazin-1-yl)methyl)-1H-benzo[d]imidazol-2-yl)phenyl)ethynyl)pyrimidin-2-amine The title compound was synthesized from N-cyclopropyl-5-ethynylpyrimidin-2-amine (as prepared above) and 2-(3-iodo-4-methylphenyl)-6-((4-methylpiperazin-1-yl)methyl)-1H-benzo[d]imidazole (as prepared in Example 1) in a manner similar to that described for in Example 1. The title compound was obtained as a brown solid. Mp: 136-137° C.; $^1$H NMR (300 MHz, $CDCl_3$) δ: 8.40 (2 H, s), 8.21 (1 H, s), 7.96-7.99 (1 H, d, J=9.0 Hz), 7.52-7.55 (1 H, d, J=9.0 Hz), 7.49-7.52 (1 H, d, J=9.0 Hz), 7.23-7.26 (1 H, d, J=9.0 Hz), 7.15-7.18 (1 H, d, J=9.0 Hz), 5.81 (1 H, s), 5.28 (1 H, s), 3.57 (2 H, s), 2.78 (1 H, s), 2.55 (8H, brs), 2.46 (3 H, s), 2.32 (3 H, s), 0.83-0.87 (2 H, m), 0.56 (2 H, brs). HRMS (ESI-TOF$^+$): m/z $[M+H]^+$ calcd for $C_{29}H_{32}N_7$: 478.2714. found: 478.2718.

Example 6

3-(2-(2-Chloro-5-(6-((4-methylpiperazin-1-yl)methyl)-1H-benzo[d]imidazol-2-yl)phenyl)ethynyl)imidazo[1,2-b]pyridazine

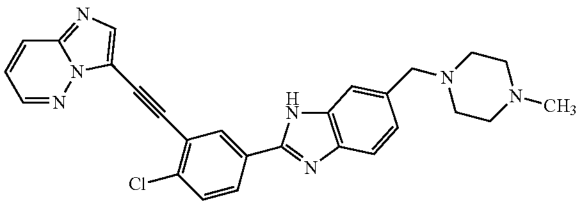 [SMILES: CN1CCN(Cc2ccc3nc(-c4ccc(Cl)c(C#Cc5cnc6cccnn56)c4)[nH]c3c2)CC1]

The title compound was synthesized from 3-ethynylimidazo[1,2-b]pyridazine (as prepared in Example 3) and 2-(4-chloro-3-iodophenyl)-6-((4-methylpiperazin-1-yl)methyl)-1H-benzoimidazole in a manner similar to that described for in Example 1. The intermediate compound 2-(4-chloro-3-iodophenyl)-6-((4-methylpiperazin-1-yl)methyl)-1H-benzo[d]imidazole was made as for Example 1 (Step 4 to 7) with the spectra below: $^1$H NMR (300 MHz, $CDCl_3$) δ: 8.52 (1 H, s), 7.95-7.98 (1 H, d, J=9.0 Hz), 7.45-7.48 (1 H, d, J=9.0 Hz), 7.43-7.46 (1 H, d, J=9.0 Hz), 7.23 (1 H, s), 7.21-7.24 (1 H, d, J=9.0 Hz), 3.59 (2 H, s), 2.51 (8H, brs), 2.29 (3 H, s).

The title compound was obtained as a khaki solid. Mp: 156-157° C.; $^1$H NMR (300 MHz, $CDCl_3$) δ: 8.43 (1 H, s), 8.36 (1 H, s), 8.11-8.14 (1 H, d, J=9.0 Hz), 8.11 (1 H, s), 7.92-7.95 (1 H, d, J=9.0 Hz), 7.54-7.57 (2 H, m), 7.45-7.45 (1 H, d, J=9.0 Hz), 7.18-7.21 (1 H, d, J=9.0 Hz), 7.10-7.11 (1 H, m), 3.60 (2 H, s), 2.61 (8 H, brs), 2.31 (3 H, s). HRMS (ESI-TOF$^+$): m/z $[M+H]^+$ calcd for $C_{27}H_{25}ClN_7$: 482.1854. found: 482.1841.

Example 7

6-(2-(2-Chloro-5-(6-((4-methylpiperazin-1-yl)methyl)-1H-benzo[d]imidazol-2-yl)phenyl)ethynyl)-N-cyclopropylpyridazin-3-amine

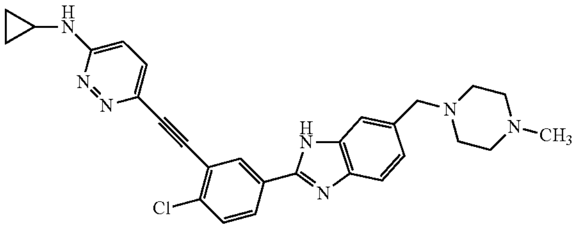 [SMILES: CN1CCN(Cc2ccc3nc(-c4ccc(Cl)c(C#Cc5ccc(NC6CC6)nn5)c4)[nH]c3c2)CC1]

The title compound was synthesized from N-cyclopropyl-6-ethynylpyridazin-3-amine and 2-(4-chloro-3-iodophenyl)-6-((4-methylpiperazin-1-yl)methyl)-1H-benzo[d]imidazole in a manner similar to that described for in Example 1. The title compound was obtained as a khaki solid. Mp: 130-131° C.; $^1$H NMR (300 MHz, $CDCl_3$) δ: 8.11-8.13 (1 H, d, J=6.0 Hz), 7.86 (1 H, s), 7.64 (2 H, m), 7.42-7.45 (1 H, d, J=9.0 Hz), 7.39-7.42 (1 H, d, J=9.0 Hz), 7.22 (1 H, s), 7.01-7.04 (1 H, d, J=9.0 Hz), 6.00 (1 H, s), 3.61 (2 H, s), 2.60 (1 H, m), 2.44 (8 H, brs), 2.27 (3 H, s), 0.87-0.89 (2 H, m), 0.65 (2 H, m). HRMS (ESI-TOF$^+$): m/z $[M+H]^+$ calcd for $C_{28}H_{29}ClN_7$: 498.2167. found: 498.2150.

Example 8

6-(2-(2-Chloro-5-(6-((4-methylpiperazin-1-yl)methyl)-1H-benzo[d]imidazol-2-yl)phenyl)ethynyl)-N-cyclobutylpyridazin-3-amine

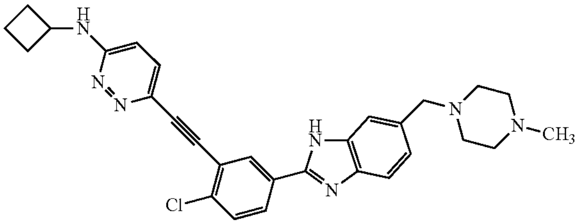 [SMILES: CN1CCN(Cc2ccc3nc(-c4ccc(Cl)c(C#Cc5ccc(NC6CCC6)nn5)c4)[nH]c3c2)CC1]

The title compound was synthesized from N-cyclobutyl-6-ethynylpyridazin-3-amine and 2-(4-chloro-3-iodophenyl)-6-((4-methylpiperazin-1-yl)methyl)-1H-benzo[d]imidazole in a manner similar to that described for in Example 1. The title compound was obtained as a pale yellow solid. Mp:161-163° C.; $^1$H NMR (300 MHz, $CDCl_3$) δ: 8.13-8.15 (1 H, d, J=6.0 Hz), 7.95 (1 H, s), 7.62-7.65 (1 H, d, J=9.0 Hz), 7.65 (1 H, s), 7.36-7.39 (1 H, d, J=9.0 Hz), 7.29-7.32 (1 H, d, J=9.0 Hz), 7.18-7.21 (1 H, d, J=9.0 Hz), 6.63-6.66 (1 H, d, J=9.0 Hz), 5.80 (1 H, s), 4.28-4.30 (1 H, m), 3.63 (2 H, s), 2.63 (8 H, brs), 2.40-2.44 (2 H, m) 2.40 (3 H, s), 1.96-2.02 (2 H, m), 1.79-1.81

(2 H, m). HRMS (ESI-TOF$^+$): m/z $[M+H]^+$ calcd for $C_{29}H_{31}ClN_7$: 512.2324. found: 512.2303.

Example 9

6-(2-(2-Chloro-5-(6-((4-methylpiperazin-1-yl)methyl)-1H-benzo[d]imidazol-2-yl)phenyl)ethynyl)-N-isopropylpyridazin-3-amine

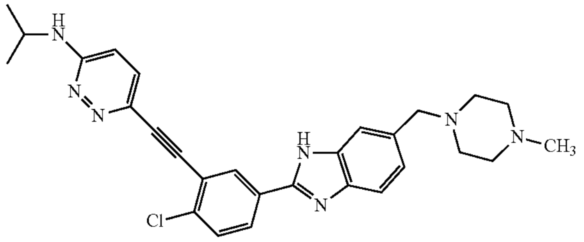 [SMILES: CC(C)Nc1ccc(C#Cc2cc(-c3nc4ccc(CN5CCN(C)CC5)cc4[nH]3)ccc2Cl)nn1]

The title compound was synthesized from N-isopropyl-6-ethynylpyridazin-3-amine and 2-(4-chloro-3-iodophenyl)-6-((4-methylpiperazin-1-yl)methyl)-1H-benzo[d]imidazole in a manner similar to that described for in Example 1. The title compound was obtained as a khaki solid. Mp: 127-128° C.; $^1H$ NMR (300 MHz, $CDCl_3$) δ: 8.11-8.13 (1 H, d, J=6.0 Hz), 7.82 (1 H, s), 7.64 (2 H, m), 7.53 (1 H, s), 7.35-7.38 (1 H, d, J=9.0 Hz), 7.29-7.32 (1 H, d, J=9.0 Hz), 6.66-6.69 (1 H, d, J=9.0 Hz), 5.22 (1 H, s), 4.12-4.14 (1 H, m), 3.62 (2 H, s), 2.51 (8 H, brs), 2.31 (3 H, s), 1.25-1.31 (6 H, m). HRMS (ESI-TOF$^+$): m/z $[M+H]^+$ calcd for $C_{28}H_{31}ClN_7$: 500.2324. found: 500.2313.

Example 10

5-(2-(2-Chloro-5-(6-((4-methylpiperazin-1-yl)methyl)-1H-benzo[d]imidazol-2-yl)phenyl)ethynyl)-N-cyclopropylpyrimidin-2-amine

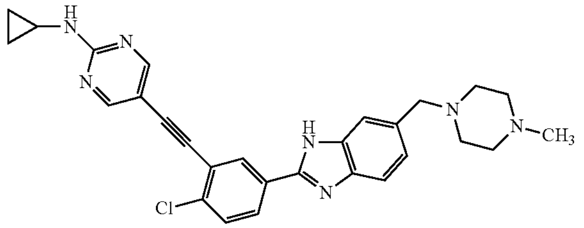 [SMILES: CN1CCN(Cc2ccc3nc(-c4ccc(Cl)c(C#Cc5cnc(NC6CC6)nc5)c4)[nH]c3c2)CC1]

The title compound was synthesized from N-cyclopropyl-5-ethynylpyrimidin-2-amine and 2-(4-chloro-3-iodophenyl)-6-((4-methylpiperazin-1-yl)methyl)-1 H-benzo[d]imidazole in a manner similar to that described for in Example 1. The title compound was obtained as a brown solid. Mp: 160-162° C.; $^1H$ NMR (300 MHz, $CDCl_3$) δ: 8.43-8.45 (2 H, d, J=6.0 Hz), 8.12-8.15 (1 H, d, J=6.0 Hz), 7.58-7.60 (1 H, d, J=6.0 Hz), 7.52 (1 H, s), 7.45-7.47 (1 H, d, J=6.0 Hz), 7.38-7.40 (1 H, d, J=6.0 Hz), 7.15-7.17 (1 H, d, J=6.0 Hz), 5.80 (1 H, s), 3.60 (2 H, s), 2.80 (8 H, brs), 2.59 (3 H, s), 1.35-1.39 (1 H, m), 0.82-0.88 (2 H, m), 0.58-0.60 (2 H, m). HRMS (ESI-TOF$^+$): m/z $[M+H]^+$ calcd for $C_{28}H_{29}ClN_7$: 498.2167. found: 498.2163.

Example 11

3-(2-(2-Methyl-5-(6-(4-methyl-1H-imidazol-1-yl)-1H-benzo[d]imidazol-2-yl)phenyl)ethynyl)imidazo[1,2-b]pyridazine

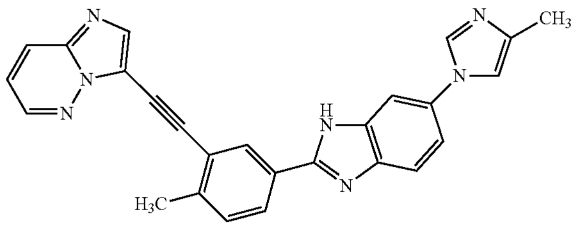 [SMILES: Cc1cn(-c2ccc3nc(-c4ccc(C)c(C#Cc5cnc6cccnn56)c4)[nH]c3c2)cn1]

Step 1. 4-(4-Methyl-1H-imidazol-1-yl)-2-nitroaniline

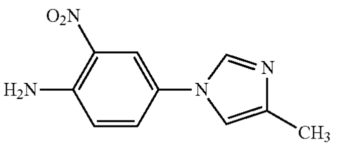

A suspension of 4-bromo-2-nitroaniline (4.34 g, 20 mmol), 4-methylimidazole (1.97 g, 24 mmol), $K_2CO_3$ (3.04 g, 22 mmol), CuI (0.57 g, 3 mmol) and 8-hydroxyquinoline (0.44 g, 3 mmol) in 20 mL DMSO was stirred at 120° C. in a sealed tube under $Ar_2$ for 29 hrs. The mixture was cooled down to rt and 28% aqueous ammonia (10 mL) was added and then $H_2O$ and EtOAc were added. The aqueous layer was extracted with EtOAc (80 mL×3) and the organic layer was washed with brine, dried with $Na_2SO_4$, after filtration, the filtrate was evaporated in vacuo and the residue was washed with PE/EtOAc to give 2.47 g product as a red solid (56.6%). $^1H$ NMR (300 MHz, DMSO-$d_6$) δ: 8.03 (1 H, d, J=2.1 Hz), 7.64-7.68 (1 H, dd, J=2.1 and 9.0 Hz), 7.53 (2 H, brs), 7.10-7.13 (1 H, d, J=9.0 Hz), 2.12 (3 H, s). LCMS: m/z $[M+H]^+$ 219.0895.

Step 2. 2-Amino-4-(4-methyl-1H-imidazol-1-yl)aniline

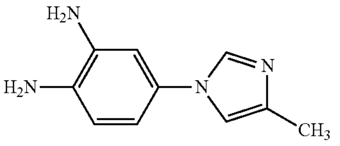

4-(4-Methyl-1H-imidazol-1-yl)-2-nitroaniline (0.22 g, 1 mmol) was suspended in 20 mL of anhydrous methanol. The mixture was reduced with 0.11 g of Raney Ni at 40 psi for 7 hrs. Then the Raney Ni was removed by filtration. The filtrate was evaporated to give the title compound 0.18 g as a yellow solid (95.7%).

Step 3. N-(2-Amino-4-(4-methyl-1H-imidazol-1-yl)phenyl)-3-iodo-4-methylbenzamide

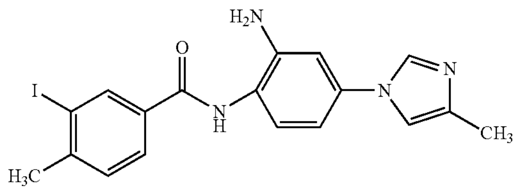 [SMILES: Cc1cn(-c2ccc(NC(=O)c3ccc(C)c(I)c3)c(N)c2)cn1]

A solution of 3-iodo-4-methylbenzoic acid (0.26 g, 1 mmol) in $SOCl_2$ (5 mL) was refluxed for 2 h, and then evaporated in vacuo to remove excess $SOCl_2$. The residue was dissolved in 5 mL anhydrous THF and added to a solution of triethylamine (0.12 g, 1.2 mmol), 2-amino-4-(4-methyl-1H-imidazol-1-yl)aniline (0.18 g, 1 mmol) and DMAP (24 mg) in 5 mL anhydrous THF in dropwise. The result mixture was stirred at rt for 20 hrs, and evaporated in vacuo. The residue was purified by chromatography on silica gel ($CH_2Cl_2$/$CH_3OH$ 97:3) to give 0.16 g product as a pale yellow solid (37.0%). LC/MS: m/z $[M+H]^+$ 433.0520.

Step 4. 2-(3-Iodo-4-methylphenyl)-6-(4-methyl-1H-imidazol-1-yl)-1H-benzo[d]imidazole

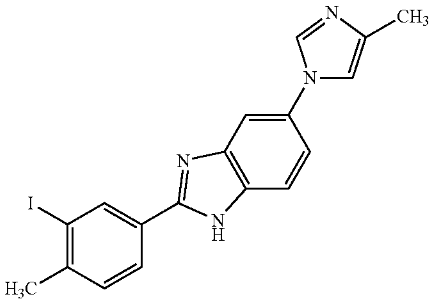 [SMILES: Cc1cn(-c2ccc3[nH]c(-c4ccc(C)c(I)c4)nc3c2)cn1]

A solution of N-(2-amino-4-(4-methyl-1H-imidazol-1-yl)phenyl)-3-iodo-4-methylbenzamide (0.16 g, 0.37 mmol) in 5 mL glacial acetic acid was refluxed for 8 hrs, and then the mixture was evaporated in vacuo, the residue was purified by chromatography on silica gel ($CH_2Cl_2$/$CH_3OH$ 97:3 to 94:6) to give 0.1 g product as pale yellow solid (65.3%). LC/MS: m/z $[M+H]^+$ 415.0415.

Step 5

3-(2-(2-Methyl-5-(5-(4-methyl-1H-imidazol-1-yl)-1H-benzo[d]imidazol-2-yl)phenyl)ethynyl)imidazo[1,2-b]pyridazine The title compound was synthesized from 3-ethynylimidazo[1,2-b]pyridazine and 2-(3-iodo-4-methylphenyl)-6-(4-methyl-1H-imidazol-1-yl)-1H-benzo[d]imidazole (as prepared above) in a manner similar to that described for in Example 1. The title compound was obtained a pale yellow solid. Mp: 182-184° C.; $^1$H NMR (400 MHz, $CD_3OD$) δ: 8.57

(2 H, brs), 8.26 (1 H, s), 7.98-8.05 (3 H, m), 7.74 (1 H, s), 7.68-7.70 (1 H, d, J=8.4 Hz), 7.46-7.48 (2 H, m), 7.42-7.44 (1 H, d, J=8.4 Hz), 7.29-7.33 (1 H, dd, J=4.4 and 9.2 Hz), 2.61 (3 H, s), 2.31 (3 H, s). HRMS (ESI-TOF$^+$): m/z $[M+H]^+$ calcd for $C_{26}H_{20}N_7$: 430.1775. found: 430.1778.

Example 12

3-(2-(6-(Cyclopropylamino)pyridazin-3-yl)ethynyl)-4-methyl-N-(4-((4-methylpiperazin-1-yl)methyl)-3-(trifluoromethyl)phenyl)benzamide

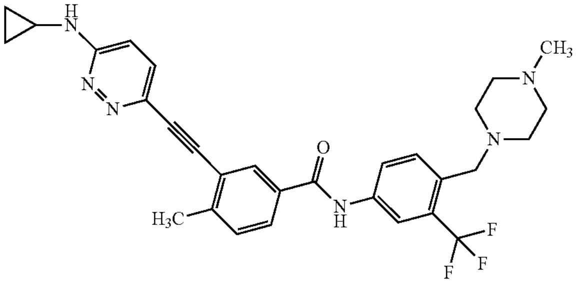 [SMILES: Cc1ccc(C(=O)Nc2ccc(CN3CCN(C)CC3)c(C(F)(F)F)c2)cc1C#Cc1ccc(NC2CC2)nn1]

Step 1. 1-(Bromomethyl)-2-(trifluoromethyl)-4-nitrobenzene

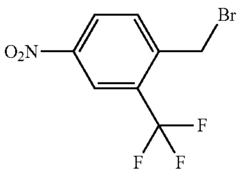 [SMILES: O=[N+]([O-])c1ccc(CBr)c(C(F)(F)F)c1]

Into a solution of 1-methyl-4-nitro-2-trifluormethylbenzene (4.1 g, 20 mmol) in carbon tetrachloride (30 mL) were added NBS (5.4 g, 30 mmol) and AIBN (493 mg, 3 mmol). The reaction was refluxed overnight and then partitioned with water. The organic layer was separated and the aqueous layer was extracted with $CH_2Cl_2$. The combined organic extracts were washed with water, dried over $Na_2SO_4$, filtered and concentrated to afford the material that was not purified but used directly in the next step.

Step 2. 4-Methyl-1-(4-nitro-2-(tritluoromethyl)benzyl)piperazine

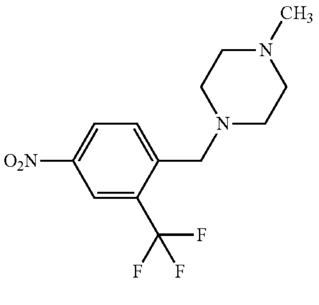 [SMILES: CN1CCN(Cc2ccc([N+](=O)[O-])cc2C(F)(F)F)CC1]

To a solution of crude 1-(bromomethyl)-2-(trifluoromethyl)-4-nitrobenzene (13.7 mmol, 60% pure) in $CH_2Cl_2$ (20 mL) was added $Et_3N$ (1.5 g, 15 mmol) and 4-methylpiperazine (1.5 g, 15 mmol). After stirring for 5 hrs at rt, 50 mL $H_2O$ was added, and the mixture was extracted with 50 mL $CH_2Cl_2$. The combined organic layer was dried over $Na_2SO_4$, filtered, concentrated, and the resulting residue was purified by silica gel chromatography (eluent: 10% MeOH in $CH_2Cl_2$) to give the product (67.4%, 2.8 g). $^1H$ NMR (300 MHz, $CDCl_3$) δ: 8.52 (1 H, s), 8.37-8.40 (1 H, d, J=9.0 Hz), 8.00-8.03 (1 H, d, J=9.0 Hz), 3.85 (2 H, s), 3.09-3.15 (2 H, m), 2.90-2.93 (2 H, m), 2.80-2.83 (2 H, m), 2.67 (3 H, s), 2.53-2.59 (2 H, m).

Step 3. 4-((4-Methylpiperazin-1-yl)methyl)-3-(trifluoromethyl)aniline

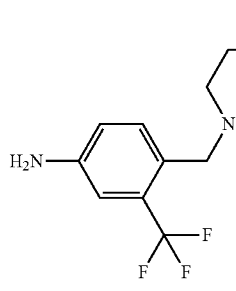

Into a solution 4-methyl-1-(4-nitro-2-(trifluoromethyl)benzyl)piperazine (1.5 g, 5 mmol) in MeOH (250 mL) was added Raney Nickel (0.15 g, 10 wt %). The suspension was stirred under hydrogen atmosphere (50 psi) for 24 hrs and monitored by TLC. The reaction mixture was filtered through celite and the filtrate was concentrated under reduced pressure to yield the desired product (1.36 g, 100%).$^1H$ NMR (300 MHz, $CDCl_3$) δ: 7.43-7.46 (1 H, d, J=9.0 Hz), 6.91 (1 H, s), 6.77-6.80 (1 H, d J=9.0 Hz), 3.77 (2 H, s), 3.54 (2 H, s), 2.53 (8H, brs), 2.34 (3 H, s).

Step 4. 3-Iodo-4-methyl-N-(4-((4-methylpiperazin-1-yl)methyl)-3-(trifluoromethyl)phenyl)benzamide

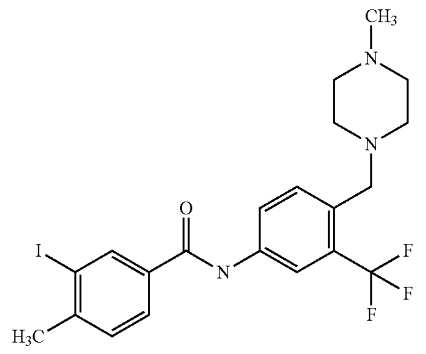 [SMILES: Cc1ccc(C(=O)Nc2ccc(CN3CCN(C)CC3)c(C(F)(F)F)c2)cc1I]

3-Iodo-4-methylbenzoyl chloride (1.06 g, 3.8 mmol), prepared from the reaction of 3-iodo-4-methylbenzoic acid and $SOCl_2$, was added to a solution of 4-((4-methylpiperazin-1-yl)methyl)-3-(trifluoromethyl)aniline (1.00 g, 3.6 mmol), $Et_3N$ (0.36 g 3.6 mmol), and a catalytic amount of DMAP in THF (20 mL). After stirring at rt for 2 hrs, the reaction was quenched with water. EtOAc was added and the layers separated. The combined organic layers were concentrated to dryness and purified by silica gel chromatography (eluent: 5% MeOH in $CH_2Cl_2$, MeOH was added 0.5% $Et_3N$) to provide the desired product as an off-white solid (67.2%, 1.25 g). $^1H$ NMR (300 MHz, $CDCl_3$) δ: 8.29 (1 H, s), 8.00 (1 H, s), 7.85 ((1 H, m), 7.73-7.76 ((2 H, m), 7.31-7.34 ((1 H, d, J=9.0 Hz), 3.64 (2 H, s), 2.53 (8 H, brs), 2.49 (3 H, s), 2.33 (3 H, s).

Step 5

3-(2-(6-(Cyclopropylamino)pyridazin-3-yl)ethynyl)-4-methyl-N-(4-((4-methylpiperazin-1-yl)methyl)-3-(trifluoromethyl)phenyl)benzamide The title compound was synthesized from N-cyclopropyl-6-ethynylpyridazin-3-amine and 3-iodo-4-methyl-N-(4-((4-methylpiperazin-1-yl)methyl)-3-(trifluoromethyl)phenyl) benzamide (as prepared above) in a manner similar to that described for in Example 1. The product was obtained as a pale yellow solid. Mp: 68-69° C.; $^1H$ NMR (300 MHz, $CDCl_3$) δ: 8.84 (1 H, s), 7.99-8.01 (2 H, d, J=6.0 Hz), 7.95-7.98 (1 H, d, J=9.0 Hz), 7.82-7.85 (1 H, d, J=9.0 Hz), 7.71-7.73 (1 H, d, J=6.0 Hz), 7.40-7.43 (1 H, d, J=9.0 Hz), 7.29-7.32 (1 H, d, J=9.0 Hz), 6.99-7.02 (1 H, d, J=9.0 Hz), 5.85 (1 H, s), 3.63 (2 H, s), 2.53 (8 H, brs), 2.34 (3 H, s), 2.03 (3 H, s), 1.43 (1 H, m), 0.86-0.88 (2 H, m), 0.61-0.63 (2 H, m). HRMS (ESI-TOF$^+$): m/z $[M+H]^+$ calcd for $C_{30}H_{32}F_3N_6O$: 549.2584. found: 549.2568.

Example 13

3-(2-(6-(Cyclobutylamino)pyridazin-3-yl)ethynyl)-4-methyl-N-(4-((4-methylpiperazin-1-yl)methyl)-3-(trifluoromethyl)phenyl)benzamide

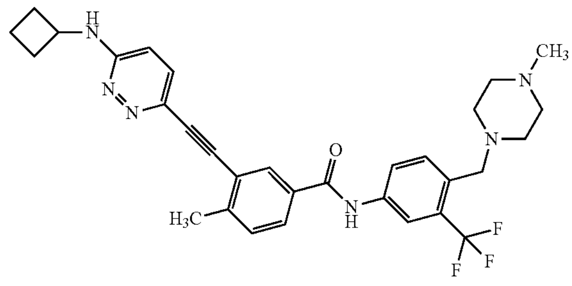 [SMILES: Cc1ccc(C(=O)Nc2ccc(CN3CCN(C)CC3)c(C(F)(F)F)c2)cc1C#Cc1ccc(NC2CCC2)nn1]

The title compound was synthesized from N-cyclobutyl-6-ethynylpyridazin-3-amine and 3-iodo-4-methyl-N-(4-((4-methylpiperazin-1-yl)methyl)-3-(trifluoromethyl)phenyl) benzamide in a manner similar to that described for in Example 1. The product was obtained as a pale yellow solid. Mp:120-121° C.; $^1H$ NMR (300 MHz, $CDCl_3$) δ: 9.10 (1 H, s), 8.05 (1 H, s), 7.97-7.80 (1 H, d, J=9.0 Hz), 7.94 (1 H, s), 7.81-7.83 (1 H, d, J=6.0 Hz), 7.64-7.66 (1 H, d, J=6.0 Hz), 7.28-7.31 (1 H, d, J=9.0 Hz), 7.26-7.28 (1 H, d, J=6.0 Hz), 6.57-5.59 (1 H, d, J=2.0 Hz), 5.53 (1 H, s), 4.22-4.27 (1 H, m), 3.64 (2 H, s), 2.65 (8 H, brs), 2.49 (3 H, s), 2.45 (3 H, s), 2.44 (2H, m), 1.93-1.99 (2 H, m), 1.83-1.89 (2H, m). HRMS (ESI-TOF$^+$): m/z $[M+H]^+$ calcd for $C_{31}H_{34}F_3N_6O$: 563.2741. found: 563.2768.

Example 14

3-(2-(6-(Isopropylamino)pyridazin-3-yl)ethynyl)-4-methyl-N-(4-((4-methylpiperazin-1-yl)methyl)-3-(trifluoromethyl)phenyl)benzamide

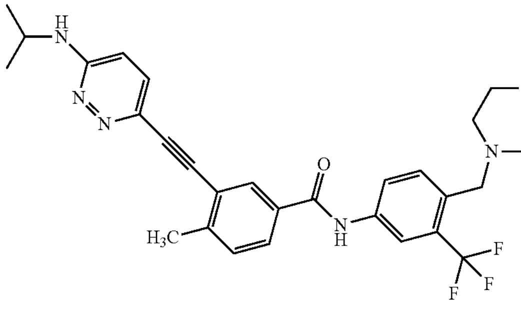

The title compound was synthesized from N-isopropyl-6-ethynylpyridazin-3-amine and 3-iodo-4-methyl-N-(4-((4-methylpiperazin-1-yl)methyl)-3-(trifluoromethyl)phenyl) benzamide in a manner similar to that described for in Example 1. The product was obtained as a pale yellow solid. Mp:67-68° C.; $^1$H NMR (300 MHz, $CDCl_3$) δ: 8.97 (1 H, s), 8.06 (1 H, s), 7.98-8.01 (1 H, d, J=9.0 Hz), 7.97 (1 H, s), 7.83-7.85 (1 H, d, J=6.0 Hz), 7.58-7.60 (1 H, d, J=6.0 Hz), 7.30-7.32 (2 H, m), 6.61-6.64 (1 H, d, J=9.0 Hz), 5.05 (1 H, s), 4.02-4.05 (1 H, m), 3.70 (2 H, s), 2.79-2.99 (8 H, brs), 2.66 (3 H, s), 2.52 (3 H, s), 1.29 (6 H, m). HRMS (ESI-TOF$^+$): m/z $[M+H]^+$ calcd for $C_{30}H_{34}F_3N_6O$: 551.2741. found: 551.2734.

Example 15

4-Chloro-3-(2-(6-(cyclopropylamino)pyridazin-3-yl)ethynyl)-N-(4-((4-methylpiperazin-1-yl)methyl)-3-(trifluoromethyl)phenyl)benzamide

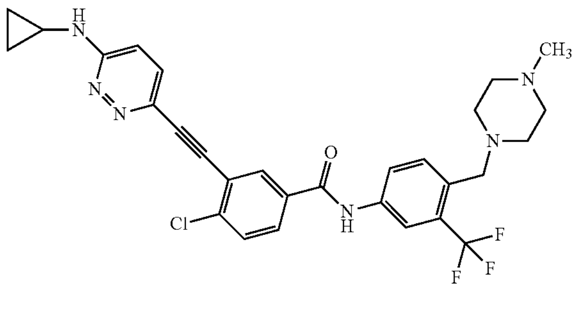 [SMILES: CN1CCN(Cc2ccc(NC(=O)c3ccc(Cl)c(C#Cc4ccc(NC5CC5)nn4)c3)cc2C(F)(F)F)CC1]

The title compound was synthesized from N-cyclopropyl-6-ethynylpyridazin-3-amine and 4-chloro-3-iodo-N-(4-((4-methylpiperazin-1-yl)methyl)-3-(trifluoromethyl)phenyl) benzamide in a manner similar to that described for in Example 1. The intermediate compound 4-chloro-3-iodo-N-(4-((4-methylpiperazin-1-yl)methyl)-3-(trifluoromethyl) phenyl)benzamide was made as for Example 12 (Step 1 to 4) with the spectra below: $^1$H NMR (300 MHz, DMSO-$d_6$) δ: 10.66 (1 H, s), 8.53 (1 H, s), 8.19 (1 H, s), 8.02-8.05 (1 H, d, J=6.0 Hz), 7.98-8.01 (1 H, d, J=6.0 Hz), 7.77 (1 H, s), 7.70-7.73 (1 H, d, J=6.0 Hz), 3.62 (2 H, s), 3.33 (2 H, m), 2.82 (2 H, m), 2.54 (4 H, m), 2.50 (3 H, s).

The title compound was obtained as a pale yellow solid. Mp:133-134° C.; $^1$H NMR (300 MHz, $CDCl_3$) δ: 9.57 (1 H, s), 8.05-8.08 (1 H, d, J=9.0 Hz), 7.85-7.88 (1 H, J=9.0 Hz), 7.67-7.70 (1 H, d, J=9.0 Hz), 7.42-7.45 (2 H, m), 7.00-70.3 (1 H, d, J=9.0 Hz), 6.00 (1 H, s), 3.61 (2 H, s), 2.53 (8 H, brs), 2.35 (3 H, s), 1.25 (1 H, s), 0.87 (2 H, m), 0.63 (2 H, m). HRMS (ESI-TOF$^+$): m/z $[M+H]^+$ calcd for $C_{29}H_{29}ClF_3N_6O$: 569.2038. found: 569.2000.

Example 16

4-Chloro-3-(2-(6-(cyclobutylamino)pyridazin-3-yl)ethynyl)-N-(4-((4-methylpiperazin-1-yl)methyl)-3-(trifluoromethyl)phenyl)benzamide

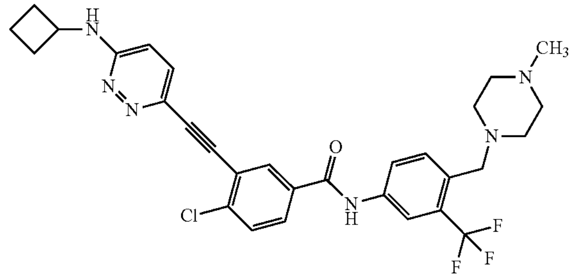 [SMILES: CN1CCN(Cc2ccc(NC(=O)c3ccc(Cl)c(C#Cc4ccc(NC5CCC5)nn4)c3)cc2C(F)(F)F)CC1]

The title compound was synthesized from N-cyclobutyl-6-ethynylpyridazin-3-amine and 4-chloro-3-iodo-N-(4-((4-methylpiperazin-1-yl)methyl)-3-(trifluoromethyl)phenyl) benzamide in a manner similar to that described for in Example 1. The product was obtained as a pale yellow solid. Mp:132-133° C.; $^1$H NMR (300 MHz, $CDCl_3$) δ: 9.53 (1 H, s), 8.10 (1 H, s), 8.00 (2 H, m), 7.85-7.87 (1 H, d, J=6.0 Hz), 7.66-7.69 (1 H, d, J=9.0 Hz), 7.43-7.45 (1 H, d, J=6.0 Hz), 7.33-7.36 (1 H, d, J=9.0 Hz), 6.58-6.61 (1 H, d, J=9.0 Hz), 5.56 (1 H, s), 4.23-4.25 (1 H, m), 3.64 (2 H, s), 2.61 (8 H, brs),2.44 (3 H, s), 2.43 (2 H, m), 1.91-1.97 (2 H, m), 1.81-1.86 (1 H, brs). HRMS (ESI-TOF$^+$): m/z $[M+H]^+$ calcd for $C_{30}H_{31}ClF_3N_6O$: 583.2194. found: 583.2174.

Example 17

4-Chloro-3-(2-(6-(isopropylamino)pyridazin-3-yl)ethynyl)-N-(4-((4-methylpiperazin-1-yl)methyl)-3-(trifluoromethyl)phenyl)benzamide)

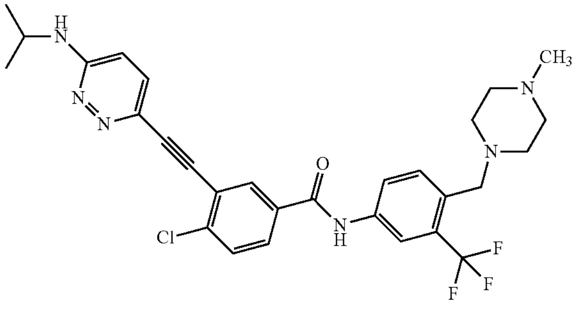 [SMILES: CC(C)Nc1ccc(C#Cc2cc(C(=O)Nc3ccc(CN4CCN(C)CC4)c(C(F)(F)F)c3)ccc2Cl)nn1]

The title compound was synthesized from N-isopropyl-6-ethynylpyridazin-3-amine and 4-chloro-3-iodo-N-(4-((4-methylpiperazin-1-yl)methyl)-3-(trifluoromethyl)phenyl)

benzamide in a manner similar to that described for in Example 1. The product was obtained as a pale yellow solid. Mp:133-134° C.; $^1$H NMR (300 MHz, $CDCl_3$) δ: 9.62 (1 H, s), 8.11 (1 H, s), 8.05 (1 H, s), 8.01-8.03 (1 H, d, J=9.0 Hz), 7.86-7.88 (1 H, d, J=6.0 Hz), 7.60-7.63 (1 H, d, J=6.0 Hz), 7.44-7.47 (1 H, d, J=9.0 Hz), 7.33-7.36 (1 H, d, J=9.0 Hz), 6.63-6.66 (1 H, d, J=9.0 Hz), 3.99-4.07 (1 H, m), 3.67 (2 H, s), 2.84 (8 H, brs), 2.56 (3 H, s), 1.25-1.30 (6 H, m). HRMS (ESI-TOF$^+$): m/z $[M+H]^+$ calcd for $C_{29}H_{30}ClF_3N_6O$: 571.2194. found: 571.2209.

Example 18

3-(2-(6-(Cyclopropylamino)pyridazin-3-yl)ethynyl)-4-methyl-N-(4-(4-methyl-1H-imidazol-1-yl)-3-(trifluoromethyl)phenyl)benzamide

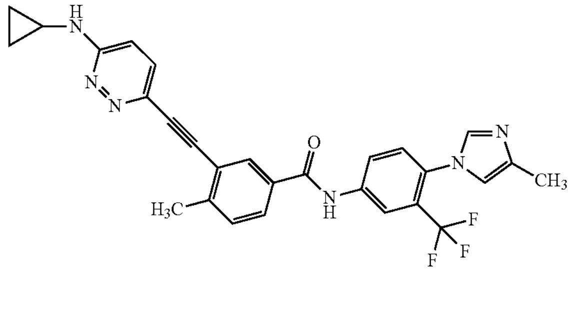 [SMILES: Cc1cn(-c2ccc(NC(=O)c3ccc(C)c(C#Cc4ccc(NC5CC5)nn4)c3)cc2C(F)(F)F)cn1]

Step 1. 4-Methyl-1-(2-(trilluoromethyl)-4-nitrophenyl)-1H-imidazole

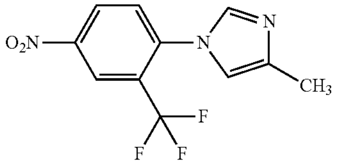 [SMILES: Cc1cn(-c2ccc([N+](=O)[O-])cc2C(F)(F)F)cn1]

A mixture of 4-methylimidazole (0.63 g, 7.67 mmol), 1-fluoro-2-(trifluoromethyl)-4-nitrobenzene (1.06 g, 5.1 mmol), and $K_2CO_3$ (1.06 g, 7.67 mmol) in acetonitrile (20 mL) was refluxed for 6 hs. The mixture was filtered through Celite and filtrate was evaporated in vacuo and the residue was purified by chromatography on silica gel (PE/EtOAc 1:1) to give 1.13 g product as light green oil (81.8%). $^1$H NMR (300 MHz, $CDCl_3$) δ: 8.71 (1 H, s), 8.52-8.55 (1 H, d, J=8.4 Hz), 7.59-7.62 (2 H, m), 6.90 (1 H, s), 2.32 (3 H, s). LCMS: m/z $[M+H]^+$ 272.0660.

Step 2. 4-(4-Methyl-1H-imidazol-1-yl)-3-(trifluoromethyl)aniline

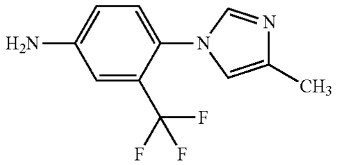

4-Methyl-1-(2-(trifluoromethyl)-4-nitrophenyl)-1 H-imidazole (1.1 g, 4.1 mmol) was suspended in 50 mL of anhydrous ethanol. The mixture was hydrogenated with 0.11 g of 10% Pd—C at 40 psi for 3 hrs. Then Pd—C was removed by filtration. The filtrate was evaporated to give the title compound 1.0 g as a yellow solid (102.0%). $^1$H NMR (300 MHz, $CDCl_3$) δ: 7.42 (1 H, s), 7.08-7.11 (1 H, d, J=8.4 Hz), 6.99 (1 H, d, J=2.4 Hz), 6.80-6.84 (1 H, dd, J=2.1 and 8.4 Hz), 6.74 (1 H, s), 4.14 (2 H, brs), 2.27 (3 H, s). LCMS: m/z $[M+H]^+$ 242.0957.

Step 3. 3-Iodo-4-methyl-N-(4-(4-methyl-1H-imidazol-1-yl)-3-(trifluoromethyl)phenyl)benzamide

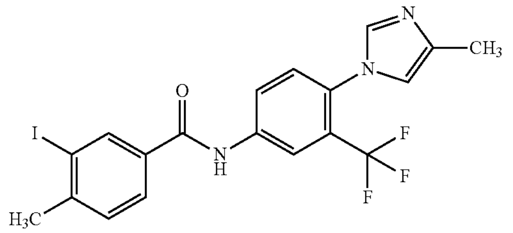 [SMILES: Cc1cn(-c2ccc(NC(=O)c3ccc(C)c(I)c3)cc2C(F)(F)F)cn1]

A solution of 3-iodo-4-methylbenzoic acid (0.26 g, 1 mmol) in $SOCl_2$ (5 mL) was refluxed for 3 hrs, then evaporated in vacuo to remove residual $SOCl_2$. The residue was dissolved in 5 mL anhydrous THF and added to a solution of triethylamine (0.12 g, 1 mmol), 4-(4-methyl-1H-imidazol-1-yl)-3-(trifluoromethyl)aniline (0.24 g, 1 mmol) and DMAP (12 mg) in 5 mL anhydrous THF in dropwise. The result mixture was stirred at rt for 40 hrs, and evaporated in vacuo. To the residue water was added and extracted with EtOAc (20 mL×3), the organic layer was washed with brine, dried with $Na_2SO_4$, after filtration, the filtrate was purified by chromatography on silica gel ($CH_2Cl_2/CH_3OH$ 97:3) to give 0.4 g crude product. The crude product was triturated with PE/EtOAc to give the title compound 0.35 g as pale yellow solid (72.2%). $^1$H NMR (300 MHz, $CDCl_3$) δ: 8.91 (1 H, s), 8.37 (1 H, s), 8.08-8.12 (2 H, m), 7.86-7.83 (1 H, d, J=8.4 Hz), 7.54 (1 H, s), 7.34-7.36 (2 H, m), 6.84 (1 H, s), 2.50 (3 H, s), 2.29 (3 H, s). LCMS: m/z $[M+H]^+$ 486.0493.

Step 4

3-(2-(6-(Cyclopropylamino)pyridazin-3-yl)ethynyl)-4-methyl-N-(4-(4-methyl-1H-imidazol-1-yl)-3-(trifluoromethyl)phenyl)benzamide The title compound was synthesized from N-cyclopropyl-6-ethynylpyridazin-3-amine and 3-iodo-4-methyl-N-(4-(4-methyl-1H-imidazol-1-yl)-3-(trifluoromethyl)phenyl) benzamide (as prepared above) in a manner similar to that described for in Example 1. The product was obtained as a pale yellow solid. Mp:125-126° C.; $^1$H NMR (300 MHz, $CDCl_3$) δ: 9.94 (1 H, s), 8.34 (1 H, s), 8.20-8.23 (1 H, d, J=8.7 Hz), 8.02 (1 H, s), 7.86-7.89 (1 H, d, J=8.1 Hz), 7.53 (1 H, s), 7.39-7.42 (1 H, d, J=9.0 Hz), 7.30-7.32 (2 H, m), 7.02-7.05 (1 H, d, J=9.2 Hz), 6.80 (1 H, s), 6.02 (1 H, s), 2.58 (1 H, m), 2.48 (3 H, s), 2.29 (3 H, s), 0.87 (2 H, m), 0.64 (2 H, brs). HRMS (ESI-TOF$^+$): m/z $[M+2H]^{+2}$ calcd for $C_{28}H_{25}F_3N_6O$: 259.1015. found: 259.1023.

Example 19

3-(2-(6-(Isopropylamino)pyridazin-3-yl)ethynyl)-4-methyl-N-(4-(4-methyl-1H-imidazol-1-yl)-3-(trifluoromethyl)phenyl)benzamide

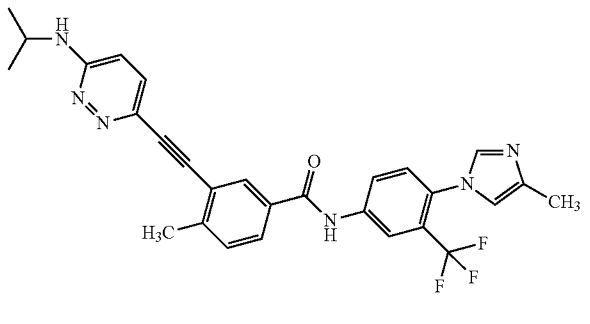 [SMILES: Cc1cn(-c2ccc(NC(=O)c3ccc(C)c(C#Cc4ccc(NC(C)C)nn4)c3)cc2C(F)(F)F)cn1]

The title compound was synthesized from N-isopropyl-6-ethynylpyridazin-3-amine and 3-iodo-4-methyl-N-(4-(4-methyl-1H-imidazol-1-yl)-3-(trifluoromethyl)phenyl) benzamide in a manner similar to that described for in Example 1. The product was obtained as a pale yellow solid. Mp:141-143° C.; $^1$H NMR (300 MHz, $CDCl_3$) δ: 9.82 (1 H, s), 8.34 (1 H, s), 8.20-8.23 (1 H, d, J=7.8 Hz), 7.96 (1 H, s), 7.84-7.86 (1 H, d, J=8.1 Hz), 7.54 (1 H, s), 7.29-7.31 (3 H, m), 6.81 (1 H, s), 6.63-6.66 (1 H, d, J=8.4 Hz), 5.11 (1 H, brs), 4.08 (1 H, m), 2.46 (3 H, s), 2.29 (3 H, s), 1.28-1.31 (6 H, d, J=6.3 Hz). HRMS (ESI-TOF$^+$): m/z $[M+H]^+$ calcd for $C_{28}H_{26}F_3N_6O$: 519.2115. found: 519.2116.

Example 20

4-Chloro-3-(2-(6-(cyclopropylamino)pyridazin-3-yl)ethynyl)-N-(4-(4-methyl-1H-imidazol-1-yl)-3-(trifluoromethyl)phenyl)benzamide

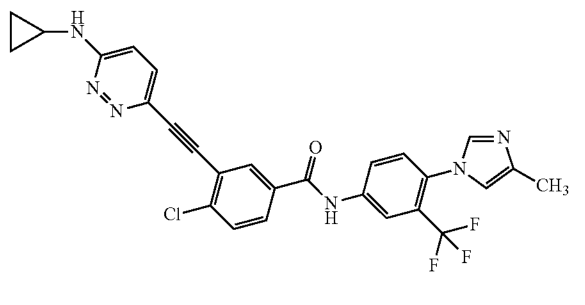 [SMILES: Cc1cn(-c2ccc(NC(=O)c3ccc(Cl)c(C#Cc4ccc(NC5CC5)nn4)c3)cc2C(F)(F)F)cn1]

The title compound was synthesized from N-cyclopropyl-6-ethynylpyridazin-3-amine and 4-chloro-3-iodo-N-(4-(4-methyl-1H-imidazol-1-yl)-3-(trifluoromethyl)phenyl)benzamide in a manner similar to that described for in Example 1. The intermediate compound 4-chloro-3-iodo-N-(4-(4-methyl-1H-imidazol-1-yl)-3-(trifluoromethyl)phenyl)benzamide was made as for Example 18 (Step 1 to 3) with the spectra below: $^1$H NMR (300 MHz, DMSO-$d_6$) δ: 10.78 (1 H, s), 8.55 (1 H, d, J=2.1 Hz), 8.26 (1 H, s), 8.22 (1 H, s), 8.11 (1 H, s), 7.99-8.03 (1 H, dd, J=2.1 and 8.1 Hz), 7.76-7.80 (2 H, m), 7.49 (1 H, s), 2.19 (3 H, s). LCMS: m/z $[M+H]^+$ 505.9663.

The title compound was obtained as a pale yellow solid. Mp: 150-152° C.; $^1$H NMR (300 MHz, $CDCl_3$) δ: 10.45 (1 H, s), 8.38 (1 H, s), 8.24-8.27 (1 H, d, J=8.1 Hz), 8.10 (1 H, s), 7.85-7.87 (1 H, d, J=6.9 Hz), 7.42-7.52 (3 H, m), 7.29-7.32 (1 H, d, J=9.0 Hz), 7.07 (1 H, s), 6.80 (1 H, s), 6.09 (1 H, s), 2.59 (1 H, brs), 2.28 (3 H, s), 0.88-0.89 (2 H, m), 0.65 (2 H, brs). HRMS (ESI-TOF$^+$): m/z $[M+2H]^{+2}$ calcd for $C_{27}H_{22}ClF_3N_6O$: 269.0742. found: 269.0735.

Example 21

4-Chloro-3-(2-(6-(cyclobutylamino)pyridazin-3-yl)ethynyl)-N-(4-(4-methyl-1H-imidazol-1-yl)-3-(trifluoromethyl)phenyl)benzamide

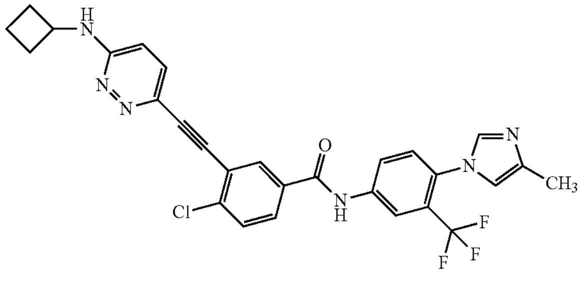 [SMILES: Cc1cn(-c2ccc(NC(=O)c3ccc(Cl)c(C#Cc4ccc(NC5CCC5)nn4)c3)cc2C(F)(F)F)cn1]

The title compound was synthesized from N-cyclobutyl-6-ethynylpyridazin-3-amine and 4-chloro-3-iodo-N-(4-(4-methyl-1H-imidazol-1-yl)-3-(trifluoromethyl)phenyl)benzamide in a manner similar to that described for in Example 1. The product was obtained as a pale yellow solid. Mp:153-155° C.; $^1$H NMR (300 MHz, $CDCl_3$) δ: 10.34 (1 H, s), 8.36 (1 H, s), 8.24-8.27 (1 H, d, J=8.1 Hz), 8.03 (1 H, s), 7.82-7.85 (1 H, d, J=8.1 Hz), 7.48 (1 H, s), 7.41-7.44 (1 H, d, J=8.7 Hz), 7.34-7.37 (2 H, t, J=9.3 and 8.7 Hz), 6.80 (1 H, s), 6.61-6.64 (1 H, d, J=9.6 Hz), 5.57-5.59 (1 H, d, J=6.0 Hz), 4.22-4.29 (1 H, m), 2.45-2.48 (2 H, m), 2.28 (3 H, s), 1.76-2.01 (4 H, m). HRMS (ESI-TOF$^+$): m/z $[M+2H]^{+2}$ calcd for $C_{28}H_{24}ClF_3N_6O$: 276.0821. found: 276.0817.

Example 22

4-Chloro-3-(2-(6-(isopropylamino)pyridazin-3-yl)ethynyl)-N-(4-(4-methyl-1H-imidazol-1-yl)-3-(trifluoromethyl)phenyl)benzamide)

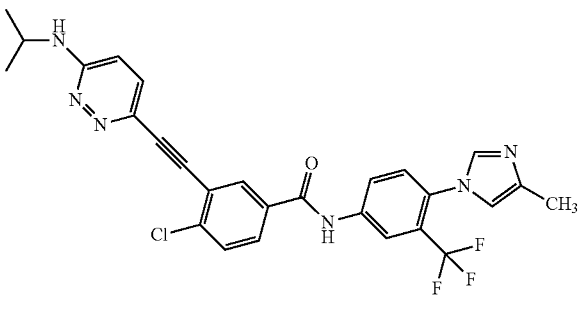 [SMILES: Cc1cn(-c2ccc(NC(=O)c3ccc(Cl)c(C#Cc4ccc(NC(C)C)nn4)c3)cc2C(F)(F)F)cn1]

The title compound was synthesized from N-isopropyl-6-ethynylpyridazin-3-amine and 4-chloro-3-iodo-N-(4-(4-methyl-1H-imidazol-1-yl)-3-(trifluoromethyl)phenyl)benzamide in a manner similar to that described for in Example 1. The product was obtained as a pale yellow solid. Mp:133-135° C.; $^1$H NMR (300 MHz, $CDCl_3$) δ: 10.46 (1 H, s), 8.40 (1 H, s), 8.28-8.31 (1 H, d, J=8.1 Hz), 8.04 (1 H, s), 7.82-7.84 (1 H, d, J=8.1 Hz), 7.53 (1 H, s), 7.41-7.43 (1 H, d, J=8.4 Hz), 7.34-7.36 (2 H, m), 6.81 (1 H, s), 6.66-6.69 (1 H, d, J=9.3 Hz), 5.13-5.15 (1 H, d, J=6.3 Hz), 4.08 (1 H, m), 2.29 (3 H, s), 1.30-1.32 (6 H, d, J=6.0 Hz). HRMS (ESI-TOF$^+$): m/z $[M+H]^+$ calcd for $C_{27}H_{23}ClF_3N_6O$: 539.1568. found: 539.1592.

Example 23

3-(2-(6-(Cyclopropylamino)pyridazin-3-yl)ethynyl)-4-methyl-N-(3-(4-methyl-1H-imidazol-1-yl)-5-(trifluoromethyl)phenyl)benzamide

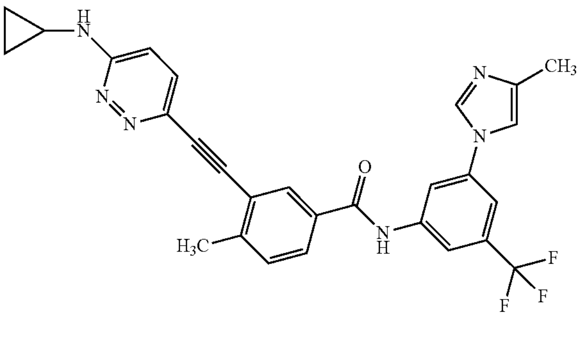 [SMILES: Cc1cn(-c2cc(NC(=O)c3ccc(C)c(C#Cc4ccc(NC5CC5)nn4)c3)cc(C(F)(F)F)c2)cn1]

The title compound was synthesized from N-cyclopropyl-6-ethynylpyridazin-3-amine and 4-chloro-3-iodo-N-(4-(4-methyl-1H-imidazol-1-yl)-3-(trifluoromethyl)phenyl)benzamide in a manner similar to that described for in Example 1. The product was obtained as a colorless solid. Mp: 226-228° C.; $^1$H NMR (300 MHz, DMSO-$d_6$) δ: 10.72 (1 H, s), 8.30 (1 H, s), 8.18-8.24 (2 H, m), 7.94-7.98 (1 H, dd, J=1.5 and 8.1 Hz), 7.72-7.74 (2 H, m), 7.55-7.59 (2 H, m), 7.50 (1 H, s), 6.93-6.96 (1 H, d, J=9.6 Hz), 2.66 (1 H, m), 2.57 (3 H, s), 2.23 (3 H, s), 0.75-0.81 (2 H, m), 0.47-0.52 (2 H, m). HRMS (ESI-TOF$^+$): m/z $[M+H]^+$ calcd for $C_{28}H_{24}F_3N_6O$: 517.1958. found: 517.1950.

Example 24

3-(2-(6-(Cyclobutylamino)pyridazin-3-yl)ethynyl)-4-methyl-N-(3-(4-methyl-1H-imidazol-1-yl)-5-(trifluoromethyl)phenyl)benzamide

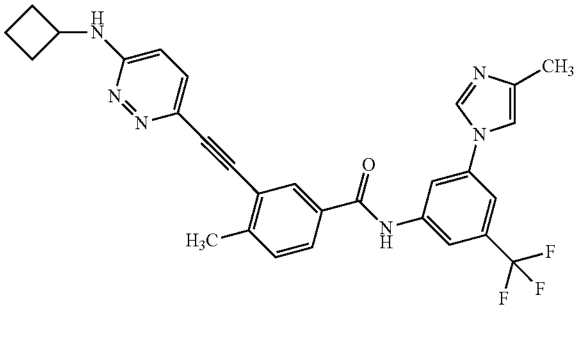 [SMILES: Cc1cn(-c2cc(NC(=O)c3ccc(C)c(C#Cc4ccc(NC5CCC5)nn4)c3)cc(C(F)(F)F)c2)cn1]

Step 1. 3-(4-Methyl-1H-imidazol-1-yl)-5-(trifluoromethyl)aniline

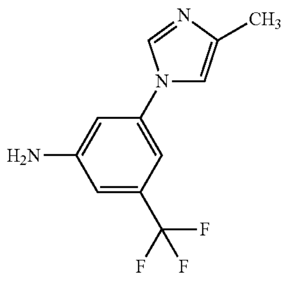 [SMILES: Cc1cn(-c2cc(N)cc(C(F)(F)F)c2)cn1]

A suspension of 3-bromo-5-(trifluoromethyl)aniline (4.8 g, 20 mmol), 4-methylimidazole (1.97 g, 24 mmol), $K_2CO_3$ (3.04 g, 22 mmol), CuI (0.57 g, 3 mmol) and 8-hydroxyquinoline (0.44 g, 3 mmol) in 20 mL DMSO was stirred at 120° C. in a sealed tube under $Ar_2$ for 16 hrs. The mixture was cooled down to 50° C. and 28% aq ammonia (10 mL) was added. The mixture was maintained at this temperature for 1 h. After cooling to rt, $H_2O$ and EtOAc were added. The aqueous layer was extracted with EtOAc (60 mL×3) and the organic layer was washed with brine, dried with $Na_2SO_4$, after filtration, the filtrate was concentrated under reduced pressure and purified by chromatography on silica gel ($CH_2Cl_2/CH_3OH$ 97:3) to give 2.85 g product as pale yellow solid (59.1%). $^1$H NMR (300 MHz, $CDCl_3$) δ: 7.76 (1 H, s), 7.01 (1 H, s), 6.94 (1 H, s), 6.84 (1 H, s), 6.78 (1 H, s), 4.11 (2 H, brs), 2.29 (3 H, s). LCMS: m/z $[M+H]^+$ 242.0966.

Step 2. 3-Iodo-4-methyl-N-(3-(4-methyl-1H-imidazol-1-yl)-5-(trifluoromethyl) phenyl)benzamide

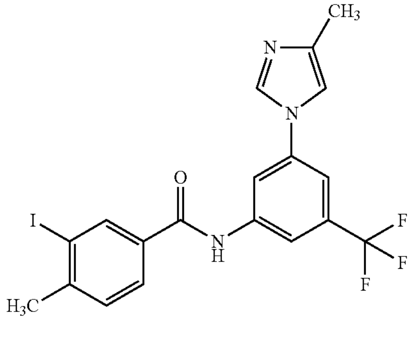 [SMILES: Cc1cn(-c2cc(NC(=O)c3ccc(C)c(I)c3)cc(C(F)(F)F)c2)cn1]

A solution of 3-iodo-4-methylbenzoic acid (1.31 g, 5 mmol) in $SOCl_2$ (10 mL) was refluxed for 2 hrs, then evaporated in vacuo to remove residual $SOCl_2$. The residue was dissolved in 5 mL anhydrous THF and added to a solution of DIPEA (0.77 g, 6 mmol), 3-(4-methyl-1H-imidazol-1-yl)-5-(trifluoromethyl)aniline (1.21 g, 5 mmol) and DMAP (24 mg) in 10 mL anhydrous THF in dropwise. The result mixture was stirred at rt for 20 hrs, and evaporated in vacuo. To the residue water was added and extracted with EtOAc (50 mL×3) then $CH_2Cl_2$. The combined organic layers were evaporated in vacuo to give crude product. The crude product was triturated with $CH_2Cl_2$/EtOAc to give the title compound 2.04 g as a colorless solid (84.3%). $^1$H NMR (300 MHz, DMSO-$d_6$) δ: 10.67 (1 H, s), 8.46 (1 H, d, J=1.5 Hz), 8.27 (1 H, s), 8.21 (1 H, s), 8.14 (1 H, s), 7.93-7.96 (1 H, dd, J=1.5 and 7.5 Hz), 7.74 (1 H, s), 7.50-7.55 (2 H, m), 2.46 (3 H, s), 2.19 (3 H, s). LCMS: m/z $[M+H]^+$ 486.0211.

Step 3

3-(2-(6-(Cyclobutylamino)pyridazin-3-yl)ethynyl)-4-methyl-N-(3-(4-methyl-1H-imidazol-1-yl)-5-(trifluoromethyl)phenyl)benzamide The title compound was synthesized from N-cyclobutyl-6-ethynylpyridazin-3-amine and 3-iodo-4-methyl-N-(3-(4-methyl-1H-imidazol-1-yl)-5-(trifluoromethyl)phenyl)benzamide (as prepared above) in a manner similar to that described for in Example 1. The product was obtained as a pale yellow solid. Mp: 223-225° C.; $^1$H NMR (300 MHz, DMSO-$d_6$) δ: 10.72 (1 H, s), 8.31 (1 H, s), 8.17-8.22 (2 H, m), 7.94-7.96 (1 H, dd, J=1.5 and 8.1 Hz), 7.75 (1 H, s), 7.47-7.61 (4 H, m), 6.77-6.80 (1 H, d, J=9.0 Hz), 4.42 (1 H, m), 2.56 (3 H, s), 2.33-2.35 (2 H, m), 2.19 (3 H, brs), 1.88-1.99 (2 H, m), 1.72-1.78 (2 H, m). HRMS (ESI-TOF$^+$): m/z $[M+H]^+$ calcd for $C_{29}H_{26}F_3N_6O$: 531.2115. found: 531.2113.

Example 25

3-(2-(6-(Isopropylamino)pyridazin-3-yl)ethynyl)-4-methyl-N-(3-(4-methyl-1H-imidazol-1-yl)-5-(trifluoromethyl)phenyl)benzamide

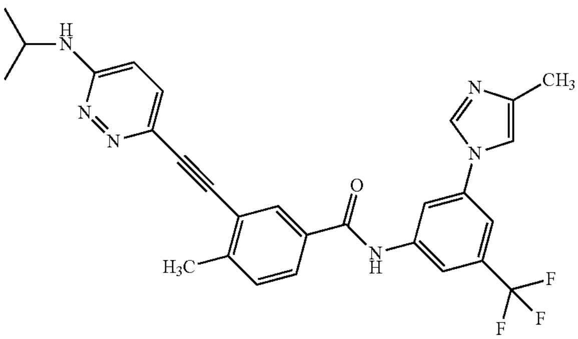 [SMILES: Cc1cn(-c2cc(NC(=O)c3ccc(C)c(C#Cc4ccc(NC(C)C)nn4)c3)cc(C(F)(F)F)c2)cn1]

The title compound was synthesized from N-isopropyl-6-ethynylpyridazin-3-amine and 3-iodo-4-methyl-N-(3-(4-methyl-1H-imidazol-1-yl)-5-(trifluoromethyl)phenyl)benzamide in a manner similar to that described for in Example 1. The product was obtained as a pale yellow solid. Mp:192-194° C.; $^1$H NMR (300 MHz, DMSO-$d_6$) δ: 10.73 (1 H, s), 8.33 (1 H, s), 8.17-8.22 (2 H, m), 7.94-7.96 (1 H, d, J=7.2 Hz), 7.76 (1 H, s), 7.54-7.57 (1 H, d, J=7.8 Hz), 7.45-7.48 (1 H, d, J=8.4 Hz), 7.15-7.18 (1 H, d, J=7.5 Hz), 6.79-6.82 (1 H, d, J=9.0 Hz), 4.14-4.20 (1 H, m), 2.56 (3 H, s), 2.19 (3 H, brs), 1.20-1.22 (6 H, d, J=6.3 Hz). HRMS (ESI-TOF$^+$): m/z $[M+H]^+$ calcd for $C_{28}H_{26}F_3N_6O$: 519.2115. found: 519.2121.

Example 26

4-Chloro-3-(2-(6-(cyclopropylamino)pyridazin-3-yl)ethynyl)-N-(3-(4-methyl-1H-imidazol-1-yl)-5-(trifluoromethyl)phenyl)benzamide

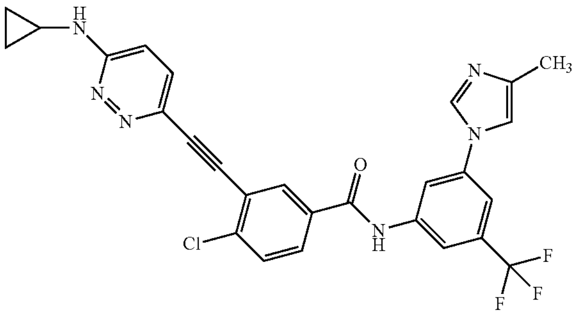 [SMILES: Cc1cn(-c2cc(NC(=O)c3ccc(Cl)c(C#Cc4ccc(NC5CC5)nn4)c3)cc(C(F)(F)F)c2)cn1]

The title compound was synthesized from N-cyclopropyl-6-ethynylpyridazin-3-amine and 4-chloro-3-iodo-N-(3-(4-methyl-1H-imidazol-1-yl)-5-(trifluoromethyl)phenyl) benzamide in a manner similar to that described for in Example 1. The intermediate compound 4-chloro-3-iodo-N-(3-(4-methyl-1H-imidazol-1-yl)-5-(trifluoromethyl)phenyl)benzamide was made as for Example 24 (Step 1 to 2) with the spectra below: $^1$H NMR (300 MHz, DMSO-$d_6$) δ: 10.78 (1 H, s), 8.55 (1 H, d, J=2.1 Hz), 8.26 (1 H, s), 8.22 (1 H, s), 8.11 (1 H, s), 7.99-8.03 (1 H, dd, J=2.1 and 8.1 Hz), 7.76-7.80 (2 H, m), 7.49 (1 H, s), 2.19 (3 H, s). LCMS: m/z $[M+H]^+$ 505.9663.

The title compound was obtained as a colorless solid. Mp:213-215° C.; $^1$H NMR (300 MHz, DMSO-$d_6$) δ: 10.83 (1 H, s), 8.37 (1 H, d, J=2.1 Hz), 8.28 (1 H, s), 8.15 (1 H, s), 8.01-8.05 (1 H, dd, J=2.1 and 8.4 Hz), 7.76-7.86 (3 H, m), 7.52-7.63 (2 H, m), 6.94-6.97 (1 H, d, J=9.3 Hz), 2.67 (1 H, m), 2.19 (3 H, s), 0.75-0.81 (2 H, m), 0.48-0.53 (2 H, m). HRMS (ESI-TOF$^+$): m/z $[M+H]^+$ calcd for $C_{27}H_{21}ClF_3N_6O$: 537.1412. found: 537.1413.

Example 27

4-Chloro-3-(2-(6-(cyclobutylamino)pyridazin-3-yl)ethynyl)-N-(3-(4-methyl-1H-imidazol-1-yl)-5-(trifluoromethyl)phenyl)benzamide

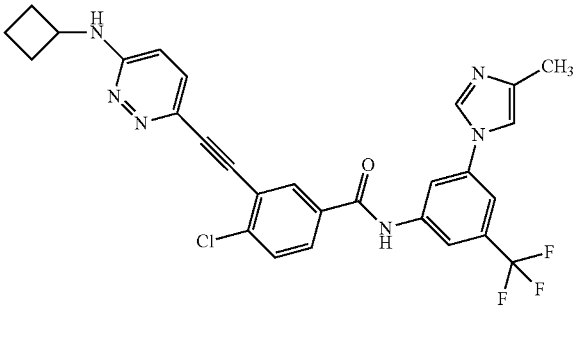 [SMILES: Cc1cn(-c2cc(NC(=O)c3ccc(Cl)c(C#Cc4ccc(NC5CCC5)nn4)c3)cc(C(F)(F)F)c2)cn1]

The title compound was synthesized from N-cyclobutyl-6-ethynylpyridazin-3-amine and 4-chloro-3-iodo-N-(3-(4-methyl-1H-imidazol-1-yl)-5-(trifluoromethyl)phenyl)benzamide in a manner similar to that described for in Example 1. The product was obtained as a pale yellow solid. Mp: 225-227° C.; $^1$H NMR (300 MHz, DMSO-$d_6$) δ: 10.82 (1 H, s), 8.35 (1 H, d, J=2.1 Hz), 8.27 (1 H, s), 8.13 (1 H, s), 7.99-8.03 (1 H, dd, J=2.1 and 8.1 Hz), 7.81-7.84 (1 H, d, J=8.7 Hz), 7.76 (1 H, s), 7.66-7.68 (2 H, m), 7.46-7.49 (1 H, d, J=9.0 Hz), 6.76-6.80 (1 H, d, J=9.3 Hz), 4.40 (1 H, m), 2.32-2.34 (2 H, m), 2.17 (3 H, brs), 1.87-1.97 (2 H, m), 1.71-1.76 (2 H, m). HRMS (ESI-TOF$^+$): m/z $[M+2H]^{+2}$ calcd for $C_{28}H_{24}ClF_3N_6O$: 276.0821. found: 276.0819.

Example 28

3-(2-(2-(Cyclopropylamino)pyrimidin-5-yl)ethynyl)-4-methyl-N-(4-(4-methyl-1H-imidazol-1-yl)-3-(trifluoromethyl)phenyl)benzamide

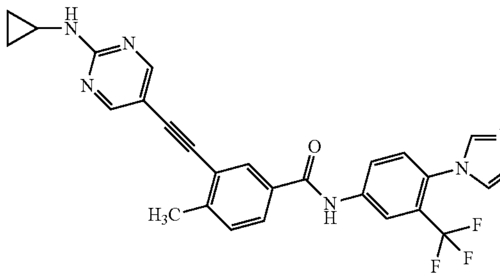

The title compound was synthesized from N-cyclopropyl-5-ethynylpyrimidin-3-amine and 3-iodo-4-methyl-N-(4-(4-methyl-1H-imidazol-1-yl)-3-(trifluoromethyl)phenyl) benzamide in a manner similar to that described for in Example 1. The product was obtained as a pale yellow solid. Mp:131-133° C.; $^1$H NMR (300 MHz, $CDCl_3$) δ: 8.49 (2 H, brs), 8.34 (1 H, s), 8.10 (2 H, m), 7.99 (1 H, s), 7.78-7.81 (1 H, d, J=8.4 Hz), 7.61 (1 H, brs), 7.37-7.40 (2 H, m), 6.83 (1 H, brs), 5.58 (1 H, s), 2.82 (1 H, m), 2.57 (3 H, s), 2.31 (3 H, s), 0.87-0.89 (2 H, m), 0.60 (2 H, brs).

HRMS (ESI-TOF$^+$): m/z $[M+H]^+$ calcd for $C_{28}H_{24}F_3N_6O$: 517.1958. found: 517.1960.

Example 29

4-Chloro-3-(2-(2-(cyclopropylamino)pyrimidin-5-yl) ethynyl)-N-(4-(4-methyl-1H-imidazol-1-yl)-3-(trifluoromethyl)phenyl)benzamide

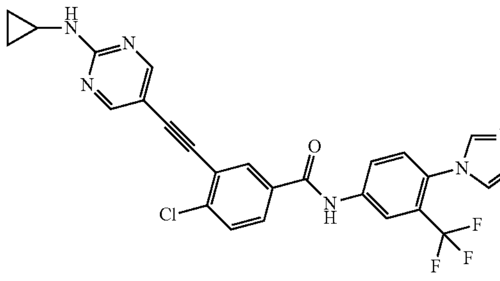

The title compound was synthesized from N-cyclopropyl-5-ethynylpyrimidin-3-amine and 4-chloro-3-iodo-N-(4-(4-methyl-1H-imidazol-1-yl)-3-(trifluoromethyl)phenyl)benzamide in a manner similar to that described for in Example 1. The product was obtained as a colorless solid. Mp:141-143° C.; $^1$H NMR (300 MHz, $CDCl_3$) δ: 8.72 (1 H, s), 8.50 (1 H, s), 8.06-8.09 (3 H, m), 7.82-7.85 (1 H, d, J=8.4 Hz), 7.55-7.58 (2 H, m), 7.35-7.38 (1 H, d, J=8.1 Hz), 6.83 (1 H, s), 5.64 (1 H, s), 2.82 (1 H, brs), 2.29 (3 H, s), 0.88-0.89 (2 H, m), 0.59 (2 H, brs). HRMS (ESI-TOF$^+$): m/z $[M+H]^+$ calcd for $C_{27}H_{21}ClF_3N_6O$: 537.1412. found: 537.1417.

Example 30

3-(2-(Imidazo[1,2-b]pyridazin-3-yl)ethynyl)-4-methyl-N-(4-(4-methyl-1H-imidazol-1-yl)-3-(trifluoromethyl)-phenyl)benzamide

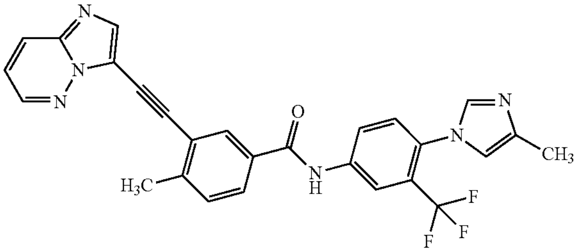 [SMILES: Cc1cn(-c2ccc(NC(=O)c3ccc(C)c(C#Cc4cnc5cccnn45)c3)cc2C(F)(F)F)cn1]

The title compound was synthesized from 3-ethynylimidazo[1,2-b]pyridazine and 3-iodo-4-methyl-N-(4-(4-methyl-1H-imidazol-1-yl)-3-(trifluoromethyl)phenyl)benzamide in a manner similar to that described for in Example 1. The title compound was obtained as a light yellow solid. Mp: 124-126° C.; $^1$H NMR (300 MHz, $CDCl_3$) δ: 9.00 (1 H, s), 8.48 (1 H, d, J=4.8 Hz), 8.17 (1 H, s), 8.09 (3 H, m), 7.93-7.95 (1 H, d, J=8.7 Hz), 7.86-7.89 (1 H, d, J=8.1 Hz), 7.55 (1 H, s), 7.39-7.42 (1 H, d, J=8.1 Hz), 7.34-7.36 (1 H, d, J=8.4 Hz), 7.11-7.16 (1 H, dd, J=4.2 and 8.4 Hz), 6.82 (1 H, s), 2.64 (3 H, s), 2.29 (3 H, s). HRMS (ESI-TOF$^+$): m/z $[M+H]^+$ calcd for $C_{27}H_{20}F_3N_6O$: 501.1645. found: 501.1626.

Example 31

4-Chloro-3-(2-(imidazo[1,2-b]pyridazin-3-yl)ethynyl)-N-(4-(4-methyl-1H-imidazol-1-yl)-3-(trifluoromethyl)phenyl)benzamide

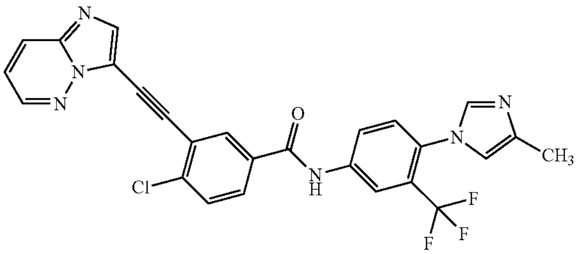 [SMILES: Cc1cn(-c2ccc(NC(=O)c3ccc(Cl)c(C#Cc4cnc5cccnn45)c3)cc2C(F)(F)F)cn1]

The title compound was synthesized from 3-ethynylimidazo[1,2-b]pyridazine and 4-chloro-3-iodo-N-(4-(4-methyl-1H-imidazol-1-yl)-3-(trifluoromethyl)phenyl)benzamide in a manner similar to that described for in Example 1. The title compound was obtained as a light yellow solid. Mp: 153-155° C.; $^1$H NMR (300 MHz, $CDCl_3$) δ: 9.39 (1 H, s), 8.49 (1 H, d, J=3.3 Hz), 8.08-8.18 (4 H, m), 7.91-7.94 (2 H, m), 7.57-7.60 (2 H, m), 7.34 (1 H, brs), 7.14-7.16 (1 H, m), 6.85 (1 H, brs), 2.28 (3 H, s). HRMS (ESI-TOF$^+$): m/z $[M+H]^+$ calcd for $C_{26}H_{17}ClF_3N_6O$: 521.1099. found: 521.1092.

Example 32

4-Chloro-3-(2-(imidazo[1,2-b]pyridazin-3-yl)ethynyl)-N-(3-(4-methyl-1H-imidazol-1-yl)-5-(trifluoromethyl)phenyl)benzamide

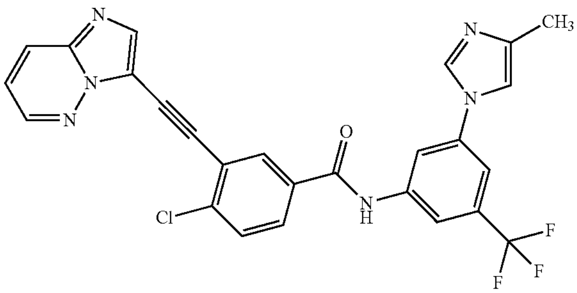 [SMILES: Cc1cn(-c2cc(NC(=O)c3ccc(Cl)c(C#Cc4cnc5cccnn45)c3)cc(C(F)(F)F)c2)cn1]

The title compound was synthesized from 3-ethynylimidazo[1,2-b]pyridazine and 4-chloro-3-iodo-N-(3-(4-methyl-1H-imidazol-1-yl)-5-(trifluoromethyl)phenyl)benzamide in a manner similar to that described for in Example 1. The title compound was obtained as a light yellow solid. Mp: 153-154° C.; $^1$H NMR (300 MHz, $CDCl_3$) δ: 9.35 (1 H, s), 8.48-8.49 (1 H, d, J=3.6 Hz), 8.25 (1 H, s), 8.15 (2 H, brs), 7.89-7.92 (4 H, m), 7.57-7.60 (1 H, d, J=8.4 Hz), 7.37 (1 H, s), 7.12-7.16 (1 H, dd, J=4.2 and 9.3 Hz), 2.27 (3 H, s). HRMS (ESI-TOF$^+$): m/z $[M+2H]^{+2}$ calcd for $C_{26}H_{18}ClF_3N_6O$: 261.0586. found: 261.0584.

Example 33

4-Chloro-3-(2-(2-(cyclopropylamino)pyrimidin-5-yl)ethynyl)-N-(3-(4-methyl-1H-imidazol-1-yl)-5-(trifluoromethyl)phenyl)benzamide

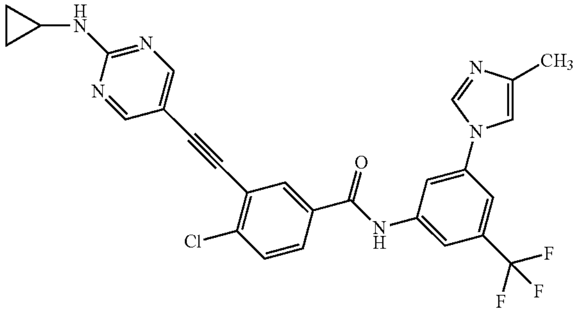

The title compound was synthesized from N-cyclopropyl-5-ethynylpyrimidin-3-amine and 4-chloro-3-iodo-N-(3-(4-methyl-1H-imidazol-1-yl)-5-(trifluoromethyl)phenyl)benzamide in a manner similar to that described for in Example 1. The product was obtained as a colorless solid. Mp: 163-165° C.; $^1$H NMR (300 MHz, DMSO-$d_6$) δ: 10.79 (1 H, s), 8.53 (3 H, brs), 8.19-8.25 (2 H, m), 8.12 (1 H, s), 7.95-8.00 (2 H, m), 7.75-7.79 (2 H, m), 2.75 (1 H, brs), 2.16 (3 H, s), 0.68-0.79 (2 H, m), 0.51 (2 H, brs). HRMS (ESI-TOF$^+$): m/z $[M+H]^+$ calcd for $C_{27}H_{21}ClF_3N_6O$: 537.1412. found: 537.1399.

Example 34

3-(2-(Imidazo[1,2-b]pyridazin-3-yl)ethynyl)piperidine-N-(4-((4-methylpiperazin-1-yl)methyl)-3-(trifluoromethyl)phenyl)-1-carboxamide

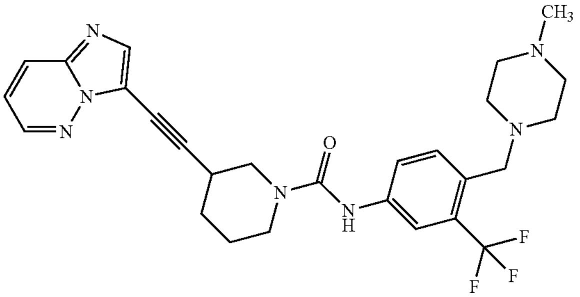 [SMILES: CN1CCN(Cc2ccc(NC(=O)N3CCCC(C#Cc4cnc5cccnn45)C3)cc2C(F)(F)F)CC1]

Step 1. 1-BOC-3-formylpiperidine

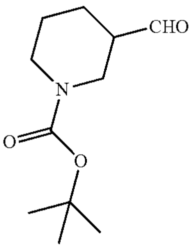

1-BOC-3-hydroxymethylpiperidine (2.15 g, 10 mmol) and triethylamine (3.03 g, 30 mmol) were dissolved in 10 mL DMSO, 15 mL DMSO solution of $SO_3Py$ (4.77 g, 30 mmol) was added to the above mixture in dropwise and the result mixture was stirred at rt for 2 hrs. The mixture was poured into 100 mL ice-water, extracted with EtOAc (100 mL×3), organic layer was washed with brine, dried with $Na_2SO_4$, filtered, and the filtrate was evaporated in vacuo. The crude product was purified by chromatography on silica gel (PE/EtOAc 5:1) to give 1.46 g product as colorless oil (68.5%). $^1$H NMR (300 MHz, $CDCl_3$) δ: 9.70 (1 H, s), 3.91-3.93 (1 H, m), 3.62-3.67 (1 H, m), 3.29-3.36 (1 H, m), 3.05-3.13 (1 H, m), 2.40-2.45 (1 H, m), 1.95-1.97 (1 H, m), 1.63-1.72 (1 H, m), 1.49-1.59 (1 H, m), 1.46 (9 H, s).

Step 2. 1-BOC-3-ethynylpiperidine

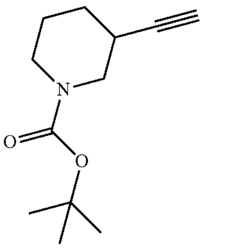

A solution of 1-BOC-3-formylpiperidine (1.46 g, 6.85 mmol) and (diazomethyl) phosphonic acid dimethyl ester (1.79 g, 11.94 mmol) in 50 mL methanol was stirred at ice-bath for 10 min, $K_2CO_3$ (1.96 g, 14.2 mmol) was added to the above mixture and stirred at ice-bath for 2 hrs, then stirred at rt overnight. The mixture was evaporated in vacuo, to the residue was added EtOAc and water, the organic layer was separated and water layer was extracted with EtOAc (100 mL×3). The combined organic layers were washed with water and brine successively, dried with $Na_2SO_4$, filtered, and the filtrate was evaporated in vacuo to give 1.44 g product as colorless oil (100.0%). $^1$H NMR (300 MHz, $CDCl_3$) δ: 3.90 (1 H, brs), 3.70-3.75 (1 H, m), 2.95-3.02 (2 H, m), 2.40-2.47 (1 H, m), 2.05 (1 H, d, J=2.1 Hz), 1.94-1.99 (1 H, m), 1.69-1.73 (1 H, m), 1.50-1.63 (2 H, m), 1.46 (9 H, s).

Step 3. 1-BOC-3-(2-(imidazo[1,2-b]pyridazin-3-yl)ethynyl)piperidine

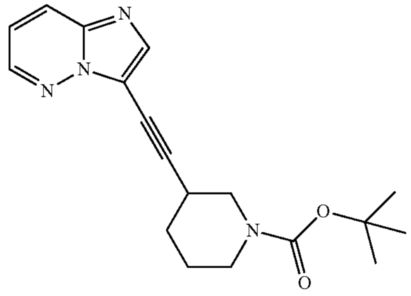 [SMILES: CC(C)(C)OC(=O)N1CCCC(C#Cc2cnc3cccnn23)C1]

A solution of 3-bromoimidazo[1,2-b]pyridazine (0.40 g, 2 mmol), 1-BOC-3-ethynylpiperidine (0.55 g, 2.6 mmol), $Pd(PPh_3)_2Cl_2$ (70 mg, 0.1 mmol), CuI (29 mg, 0.15 mmol), and DIPEA (0.39 g, 3 mmol) in DMF (20 mL) was stirred at 80° C. under $Ar_2$ for 6 hrs. The mixture was poured into 100 mL water, extracted with EtOAc (60 mL×3), organic layer was washed with brine, dried with $Na_2SO_4$, filtered, and the filtrate was evaporated in vacuo. The crude product was purified by chromatography on silica gel (PE/EtOAc 7:3 to 3:2) to give 0.39 g product as yellow oil (60.0%). $^1$H NMR (300 MHz, $CDCl_3$) δ: 8.50 (1 H, d, J=4.2 Hz), 7.98-8.08 (2 H, m), 7.13-7.17 (1 H, dd, J=4.5 and 8.7 Hz), 4.09 (1 H, brs), 3.76-3.82 (1 H, m), 3.19 (1 H, brs), 3.02-3.09 (1 H, m), 2.81-2.88 (1 H, m), 2.32 (1 H, brs), 2.11-2.15 (1 H, m), 1.67-1.81 (2 H, m), 1.46 (9 H, s). LCMS: m/z $[M+H]^+$ 327.2112.

Step 4. 3-(2-(Imidazo[1,2-b]pyridazin-3-yl)ethynyl)piperidine

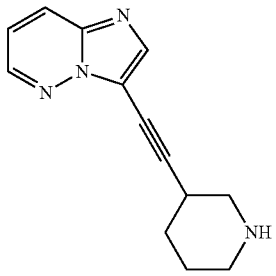 [SMILES: C(#CC1CCCNC1)c1cnc2cccnn12]

To a solution of 1-BOC-3-(2-(imidazo[1,2-b]pyridazin-3-yl)ethynyl)piperidine (0.39 g, 1.2 mmol) in $CH_2Cl_2$ (10 mL) was added TFA (1.23 g, 10.8 mmol), the mixture was stirred at rt overnight and evaporated in vacuo. To the residue was added 10 mL 10% $K_2CO_3$ solution, extracted with EtOAc (20 mL×3), dried with $Na_2SO_4$, after filtration, and the filtrate was evaporated under reduced pressure to give 0.33 g product as yellow oil (107.0%). $^1$H NMR (300 MHz, $CDCl_3$) δ: 8.43 (1 H, d, J=4.5 Hz), 7.93-7.97 (1 H, dd, J=1.8 and 9.0 Hz), 7.91 (1 H, s), 7.05-7.09 (1 H, dd, J=4.5 and 9.0 Hz), 2.82-2.98 (4 H, m), 2.08-2.11 (1 H, m), 1.75-1.84 (2 H, m), 1.53-1.58 (2 H, m).

Step 5

3-(2-(Imidazo[1,2-b]pyridazin-3-yl)ethynyl)piperidine-N-(4-((4-methylpiperazin-1-yl)methyl)-3-(trifluoromethyl)phenyl)-1-carboxamide To a solution of 4-((4-methylpiperazin-1-yl)methyl)-3-(trifluoromethyl)aniline (as prepared in Example 12 step 1 to 3) (0.1 g, 0.37 mmol) in 15 mL anhydrous dioxane was added pyridine (0.036 mL, 0.45 mmol) and 4-nitrophenyl chloroformate (90 mg, 0.45 mmol), the mixture was stirred at 60° C. for 2 hrs and then cooled to rt, and 3-(2-(imidazo[1,2-b]pyridazin-3-yl)ethynyl)piperidine (0.1 g, 0.44 mmol) was added to the above mixture. Then the mixture was stirred at 60° C. for 9 h and evaporated in vacuo. The residue was purified by chromatography on silica gel ($CH_2Cl_2/CH_3OH$ 25:1) to give 140 mg crude product, continued to purify via preparation TLC ($CH_2Cl_2/CH_3OH$ 120:15) to give 60 mg product as a pale yellow solid. Mp: 65-70° C. $^1$H NMR (300 MHz, $CDCl_3$) δ: 8.38 (1 H, s), 7.97 (1 H, d, J=9.0 Hz), 7.88 (1 H, s), 7.58-7.61 (2 H, m), 7.42-7.44 (1 H, d, J=7.8 Hz), 7.06-7.10 (1 H, m), 7.03 (1 H, s), 3.95 (1 H, m), 3.65 (4 H, m), 3.49-3.53 (2 H, m), 3.02 (4 H, m), 2.79 (4 H, brs), 2.69 (3 H, s), 2.13 (1 H, brs), 1.93 (2 H, m), 1.63 (1 H, brs). HRMS (ESI-TOF+): m/z [M+H]+ calcd for $C_{27}H_{31}F_3N_7O$: 526.2537. found: 526.2536.

Example 35

3-(2-(Imidazo[1,2-b]pyridazin-3-yl)ethynyl)pyrrolidine-N-(4-((4-methylpiperazin-1-yl)methyl)-3-(trifluoromethyl)phenyl)-1-carboxamide

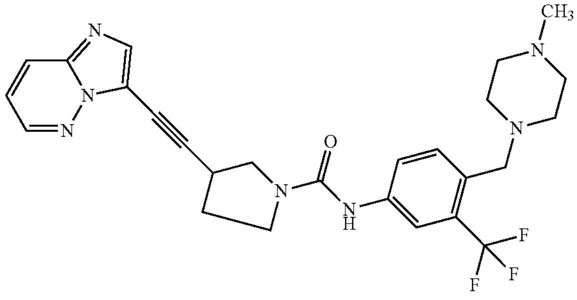 [SMILES: CN1CCN(Cc2ccc(NC(=O)N3CCC(C#Cc4cnc5cccnn45)C3)cc2C(F)(F)F)CC1]

Step 1. 1-BOC-3-formylpyrrolidine

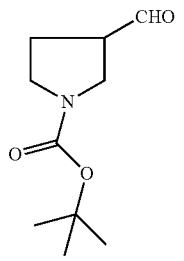

The title compound was synthesized using 1-BOC-3-hydroxymethylpyrrolidine as the material in a manner similar to that described for in Example 30 step 1. The product was obtained as colorless oil. $^1$H NMR (300 MHz, $CDCl_3$) δ: 9.68 (1 H, s), 3.70 (1 H, m), 3.48-3.51 (1 H, m), 3.37 (2 H, brs), 2.99-3.03 (1 H, m), 2.05-2.24 (2 H, m), 1.45 (9 H, s).

Step 2. 1-BOC-3-ethylnylpyrrolidine

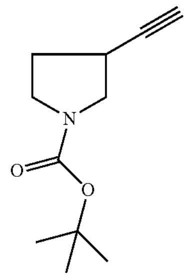

The title compound was synthesized using 1-BOC-3-formylpyrrolidine (as prepared above) as the material in a manner similar to that described for in Example 30 step 2. The product was obtained as colorless oil. $^1$H NMR (300 MHz, $CDCl_3$) δ: 3.47-3.60 (2 H, m), 3.30 (2 H, brs), 2.90-2.95 (1 H, m), 2.12-2.18 (1 H, m), 2.10 (1 H, d, J=1.8 Hz), 1.90-1.96 (1 H, m), 1.45 (9 H, s).

Step 3. 1-BOC-3-(2-(imidazo[1,2-b]pyridazin-3-yl) ethynyl)pyrrolidine

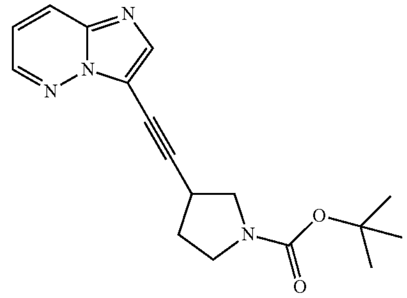 [SMILES: CC(C)(C)OC(=O)N1CCC(C#Cc2cnc3cccnn23)C1]

The title compound was synthesized using 1-BOC-3-ethynylpyrrolidine (as prepared above) as the material in a manner similar to that described for in Example 30 step 3. The product was obtained as yellow oil. $^1$H NMR (300 MHz, $CDCl_3$) δ: 8.43 (1 H, d, J=3.6 Hz), 7.92-7.99 (2 H, m), 7.07-7.11 (1 H, dd, J=4.2 and 9.0 Hz), 3.76 (1 H, m), 3.60 (1 H, m), 3.32-3.45 (2 H, m), 2.25-2.32 (1 H, m), 2.12 (1 H, m), 1.71 (1 H, m), 1.47 (9 H, s).

Step 4. 3-(2-(Imidazo[1,2-b]pyridazin-3-yl)ethynyl) pyrrolidine

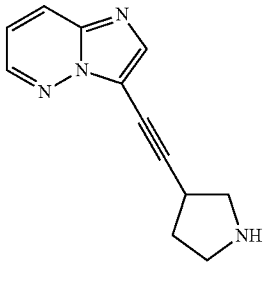 [SMILES: C(#CC1CCNC1)c1cnc2cccnn12]

The title compound was synthesized using 1-BOC-3-(2-(imidazo[1,2-b]pyridazin-3-yl) ethynyl)pyrrolidine (as prepared above) as the material in a manner similar to that described for in Example 30 step 4. The product was obtained as yellow oil. $^1$H NMR (300 MHz, $CDCl_3$) δ: 8.43 (1 H, d, J=4.2 Hz), 7.94-7.97 (1 H, d, J=9.0 Hz), 7.91 (1 H, s), 7.06-7.10 (1 H, dd, J=4.2 and 9.0 Hz), 3.10-3.35 (5 H, m), 2.24-2.31 (1 H, m), 2.05-2.09 (1 H, m).

Step 5

3-(2-(Imidazo[1,2-b]pyridazin-3-yBethynyl)pyrrolidine-N-(4-((4-methylpiperazin-1-yl)methyl)-3-(trifluoromethyl)phenyl)-1-carboxamide The title compound was synthesized from 3-(2-(imidazo [1,2-b]pyridazin-3-yl)ethynyl) pyrrolidine (as prepared above) and 4-((4-methylpiperazin-1-yl)-methyl)-3-(trifluoromethyl) aniline (as prepared in Example 12 step 1 to 3) in a manner similar to that described for in Example 30. The product was obtained as as a pale yellow solid. Mp: 83-85° C. $^{1}H$ NMR (300 MHz, $CDCl_3$) δ: 8.44 (1 H, s), 7.92-7.98 (2 H, m), 7.58-7.64 (3 H, m), 7.07-7.12 (1 H, dd, J=4.5 and 9.0 Hz), 6.37 (1 H, s), 3.88-3.93 (1 H, m), 3.76 (1 H, m), 3.49-3.70 (4 H, m), 2.62 (8 H, brs), 2.44 (4 H, brs), 2.29-2.31 (2 H, m). HRMS (ESI-TOF$^{+}$): m/z $[M+H]^{+}$ calcd for $C_{26}H_{29}F_3N_7O$: 512.2380. found: 512.2375.

Example 36

N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide

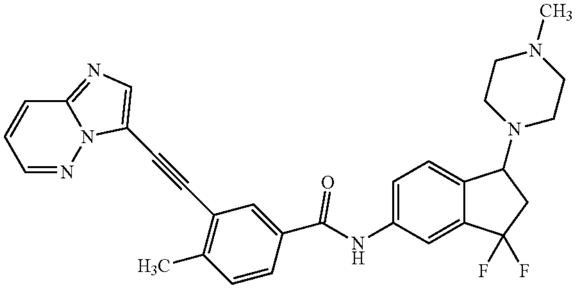 [SMILES: Cc1ccc(C(=O)Nc2ccc3c(c2)C(F)(F)CC3N2CCN(C)CC2)cc1C#Cc1cnc2cccnn12]

Step 1. 6-Nitro-1-indatone

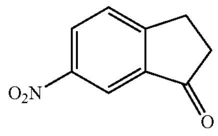 [SMILES: O=C1CCc2ccc([N+](=O)[O-])cc21]

1-Indanone (13.2 g, 0.1 mol) was added in one portion to concentrated sulfuric acid (80 mL) at 0° C. A solution of potassium nitrate (10.1 g, 0.1 mol) in concentrated sulfuric acid (30 mL) was added in small portions over a 40 min period. The mixture was stirred for 1 h at 0° C., then poured over 500 g of ice. The mixture was filtered, washed with water, and air-dried. The crude product was purified by chromatography on silica gel (PE/EtOAc 2:1) to give 11.58 g product as colorless solid (65.4%). $^{1}H$ NMR (300 MHz, $CDCl_3$) δ: 2.81-2.85 (2 H, t, J=6.3 Hz), 3.26-3.29 (2 H, t, J=6.3 Hz), 7.65-7.68 (1 H, d, J=8.4 Hz), 8.43-8.47 (1 H, dd, J=8.4 and 2.1 Hz), 8.57 (1 H, s).

Step 2. 6-Nitro-1H-inden-1-one

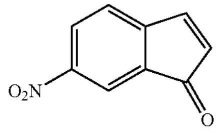 [SMILES: O=C1C=Cc2ccc([N+](=O)[O-])cc21]

To a solution of the 6-nitro-1-indatone (2.66 g, 15 mmol) in dry toluene (100 mL) at 0° C. under Ar was added successively $Et_3N$ (2.55 mL, 18 mmol) and TMSOTf (2.85 mL, 15 mmol). The mixture was warmed to room temperature and stirred for 1 h. The reaction mixture was again cooled to 0° C. and diluted with ether (100 mL) and $NaHCO_3$ solution (150 mL). The layers were separated and the aqueous phase was extracted with ether (3×50 mL). The combined organic extracts were washed with brine then dried ($Na_2SO_4$), filtered, and evaporated under reduced pressure to afford the silyl enol ether as a light yellow oil.

The silyl enol ether was dissolved in $CH_2Cl_2$ (30 mL) and added dropwise to an aluminum foil-wrapped flask containing a suspension of $Pd(OAc)_2$ (3.3 g, 15 mmol) in dry $CH_3CN$ (80 mL) under Ar. The mixture was stirred at room temperature for 2 h, then filtered through a short column of silica gel. The filtrate was evaporated under reduced pressure, and the residue was purified by chromatography on silica gel (9%-21% EtOAc/PE) to afford 0.69 g product as yellow solid (26.3%). $^{1}H$ NMR (300 MHz, $CDCl_3$) δ: 6.23-6.25 (1 H, d, J=6.3 Hz), 7.27-7.30 (1 H, d, J=8.1 Hz), 7.71-7.73 (1 H, d, J=6.0 Hz), 8.26 (1 H, s), 8.32-8.35 (1 H, dd, J=7.8 and 2.4 Hz).

Step 3. 2,3-Dihydro-3-(4-methylpiperazin-1-yl)-6-nitroindan-1-one

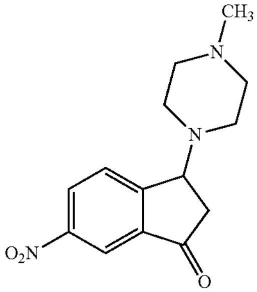 [SMILES: CN1CCN(C2CC(=O)c3cc([N+](=O)[O-])ccc32)CC1]

To a solution of 6-nitro-1H-inden-1-one (690 mg, 3.9 mmol) in THF (10 mL) was added N-methylpiperizine (0.87 mL, 7.8 mmol), and the resulting reaction mixture was stirred at room temperature for 12 h. THF was removed in vacuo, and the residue was purified by chromatography on silica gel (DCM/Methanol=10:1) to afford 0.86 g product as black oil (80.3%). $^{1}H$ NMR (300 MHz, $CDCl_3$) δ: 2.31 (3 H, s), 2.43-2.48 (6 H, m), 2.61 (2 H, brs), 2.71-2.80 (1 H, dd, J=7.2 and 12.3 Hz), 2.88-2.94 (1 H, m), 4.66 (1 H, brs), 7.89-7.92 (1 H, d, J=8.1 Hz), 8.48-8.50 (1 H, d, J=8.1 Hz), 8.56 (1 H, s).

Step 4. 1,1-Dithioacetal-2,3-dihydro-3-(4-methylpiperazin-1-yl)-6-nitroindan

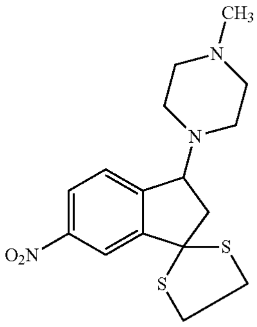 [SMILES: CN1CCN(C2CC3(SCCS3)c3cc([N+](=O)[O-])ccc32)CC1]

2,3-dihydro-3-(4-methylpiperazin-1-yl)-6-nitroindan-1-one (0.86 g, 3.1 mmol) and 1,2-ethanedithiol (0.62 mL, 7.4 mmol) were dissolved in 25 mL dichloromethane and cooled to −15° C. under Ar. Boron trifluoride-diethyl ether complex (2.2 mL, 8.4 mmol) was added at this temperature. The mixture was stirred for 3 h at −15° C. and at room temperature over night. The solution was poured carefully into saturated NaHCO3 solution. The aqueous layer was extracted three times with dichloromethane. The organic layer was washed with brine, dried (Na2SO4) and evaporated. The residue was purified by column chromatography on silica gel ($CH_2Cl_2$/Methanol=20:1 to 15:1) to afford 0.6 g product as a black solid (55.6%). LCMS: m/z $[M+H]^+$ 352.1149.

Step 5. 1-(1,1-Difluoro-2,3-dihydro-6-nitro-1H-indan-3-yl)-4-methylpiperazine

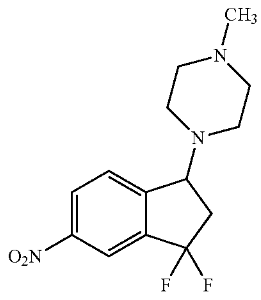 [SMILES: CN1CCN(C2CC(F)(F)c3cc([N+](=O)[O-])ccc32)CC1]

2.03 mL of a 70% solution of HF in pyridine was added to a suspension of 1,3-dibromo-dimethylhydantoin (2 g, 7 mmol) and 15 mL dichloromethane under Ar. The mixture was cooled to −74° C. and a solution of 1,1-dithioacetal-2,3-dihydro-3-(4-methyl-piperazin-1-yl)-6-nitroindan (0.6 g, 1.7 mmol) in 5 mL $CH_2Cl_2$ was added below −65° C. After 5 h the cooling bath was removed. The reaction mixture was stirred over night at rt and was poured into 50 mL 2N NaOH containing 3 ml 39% $NaHSO_3$ solution. The aqueous layer was extracted three times with dichloromethane. The combined organic layers were washed with brine, dried (Na2SO4) and evaporated. The residue was purified by column chromatography on silica gel (DCM/Methanol=30:1) to afford 90 mg product as a black solid (18.0%). LCMS: m/z $[M+H]^+$ 298.1333.

Step 6. 1-(1,1-Difluoro-2,3-dihydro-6-amino-1H-indan-3-yl)-4-methylpiperazine

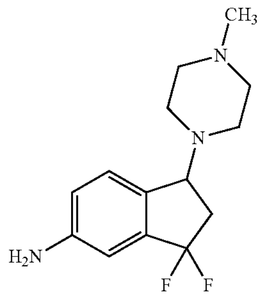

1-(1,1-difluoro-2,3-dihydro-6-nitro-1H-inden-3-yl)-4-methylpiperazine (90 mg, 0.3 mmol) was suspended in 10 ml of anhydrous ethanol. The mixture was hydrogenation with 50 mg of 10% Pd—C at ambient pressure for 5 h. Then the Pd—C was removed by filtration. The filtrate was evaporated to give the title compound 78 mg as a yellow oil (97.5%).

Step 7. N-(1,1-difluoro-2,3-dihydro-3-(4-methylpiperazin-1-yl)-1H-indan-6-yl)-3-iodo-4-methylbenzamide

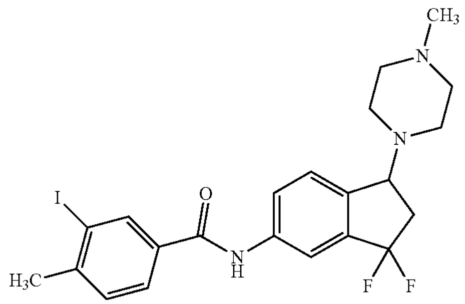 [SMILES: Cc1ccc(C(=O)Nc2ccc3c(c2)C(F)(F)CC3N2CCN(C)CC2)cc1I]

A solution of 3-iodo-4-methylbenzoic acid (79 mg, 0.3 mmol) in $SOCl_2$ (5 mL) was refluxed for 3 h, then evaporated in vacuum to remove residual $SOCl_2$. The residue was dissolved in 5 mL anhydrous THF and added to a solution of triethylamine (37 mg, 0.36 mmol), 1-(1,1-Difluoro-2,3-dihydro-6-amino-1H-indan-3-yl)-4-methylpiperazine (78 mg, 0.3 mmol) and DMAP (2 mg) in 5 mL anhydrous THF in dropwise. The result mixture was stirred at rt for 26 h, and evaporated in vacuum. The residue was purified by chromatography on silica gel ($CH_2Cl_2/CH_3OH$ 97:3) to give 140 mg product as a pale yellow solid (91.5%). LCMS: m/z $[M+H]^+$ 512.1049.

Step 8. N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide

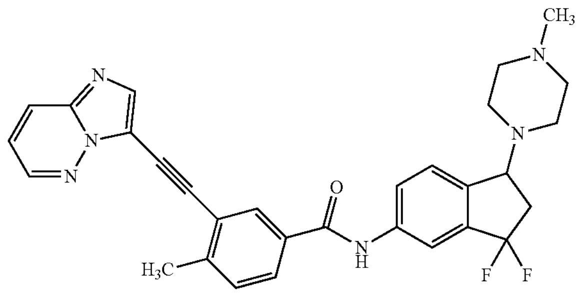

The title compound was synthesized from 3-Ethynylimidazo[1,2-b]pyridazine and N-(1,1-difluoro-2,3-dihydro-3-(4-methylpiperazin-1-yl)-1 H-indan-6-yl)-3-iodo-4-methylbenzamide in a manner similar to that described for in Example 1. The product was obtained as a pale yellow solid. Mp: 111-113° C. $^1H$ NMR (300 MHz, $CDCl_3$) δ: 0.83-0.87 (2 H, m), 2.31 (3 H, s), 2.49 (6 H, brs), 2.58-2.67 (5 H, m), 4.50-4.52 (1 H, m), 7.11-7.16 (1 H, dd, J=9.0 and 4.5 Hz), 7.38-7.41 (1 H, d, J=8.1 Hz), 7.46-7.49 (1 H, d, J=8.1 Hz), 7.80-7.89 (3 H, m), 7.96-8.00 (1 H, dd, J=9.6 and 1.5 Hz), 8.05 (1 H, d, J=1.8 Hz), 8.09 (1 H, s), 8.18 (1 H, s), 8.48-8.49

(1 H, d, J=4.2 Hz). HRMS (ESI-TOF$^+$): m/z $[M+2H]^{+2}$ calcd for $C_{30}H_{30}F_2N_6O$: 264.1219. found: 264.1212.

Example 37

3-(2-(2-(Cyclopropylamino)pyrimidin-5-yl)ethynyl)-N-(1,1-difluoro-2,3-dihydro-3-(4-methylpiperazin-1-yl)-1H-indan-6-yl)-4-methylbenzamide

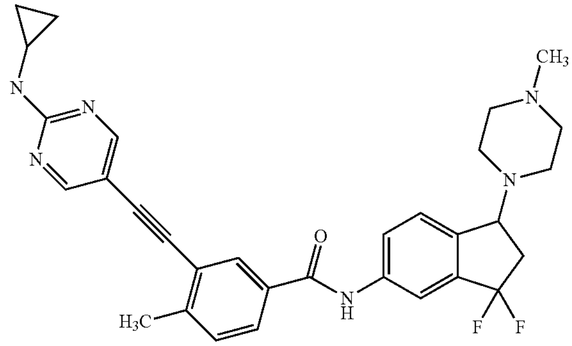 [SMILES: Cc1ccc(C(=O)Nc2ccc3c(c2)C(F)(F)CC3N2CCN(C)CC2)cc1C#Cc1cnc(NC2CC2)nc1]

The title compound was synthesized from N-cyclopropyl-5-ethynylpyrimidin-3-amine and N-(1,1-difluoro-2,3-dihydro-3-(4-methylpiperazin-1-yl)-1H-indan-6-yl)-3-iodo-4-methyl benzamide (as prepared in Example 36 step 1 to 7) in a manner similar to that described for in Example 1. The product was obtained as a pale yellow solid. Mp: 95-97° C. $^1$H NMR (300 MHz, $CDCl_3$) δ: 0.60-0.62 (2 H, m), 0.85-0.94 (4 H, m), 2.30 (3 H, s), 2.47 (5 H, brs), 2.56-2.67 (6 H, m), 2.82 (1 H, m), 4.49-4.51 (1 H, m), 7.35-7.38 (1 H, d, J=8.1 Hz), 7.46-7.49 (1 H, d, J=7.8 Hz), 7.74-7.79 (2 H, m), 7.83-7.86 (1 H, d, J=8.1 Hz), 7.91 (1 H, s), 7.95 (1 H, s), 8.50 (2 H, s). HRMS (ESI-TOF$^+$): m/z $[M+2H]^{+2}$ calcd for $C_{31}H_{34}F_2N_6O$: 272.1376. found: 272.1370.

Example 38

N-(1,1-difluoro-2,3-dihydro-3-(4-methylpiperazin-1-yl)-1H-indan-6-yl)-3-(2-(imidazo[1,2-b]pyridazin-3-yl)ethynyl)-4-chlorobenzamide

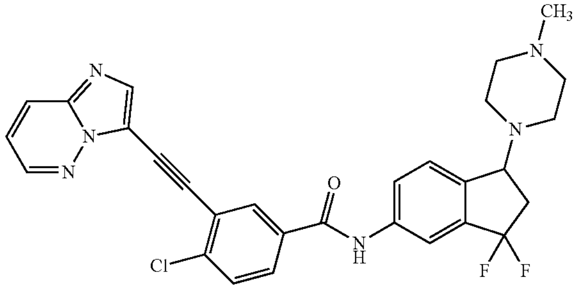

Step 1. N-(1,1-difluoro-2,3-dihydro-3-(4-methylpiperazin-1-yl)-1H-indan-6-yl)-3-iodo-4-chlorobenzamide

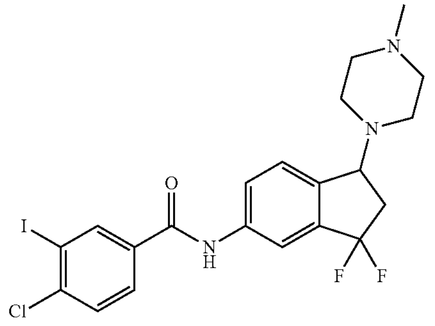 [SMILES: CN1CCN(C2CC(F)(F)c3cc(NC(=O)c4ccc(Cl)c(I)c4)ccc32)CC1]

The title compound was synthesized from 4-chloro-3-iodobenzoic acid and 1-(1,1-difluoro-2,3-dihydro-6-amino-1H-indan-3-yl)-4-methylpiperazine (as prepared in Example 36 step 6) in a manner similar to that described in Example 36 step 7. The product was obtained as a pale yellow solid. LCMS: m/z $[M+H]^+$ 532.0435.

Step 2. N-(1,1-difluoro-2,3-dihydro-3-(4-methylpiperazin-1-yl)-1H-indan-6-yl)-3-(2-(imidazo[1,2-b]pyridazin-3-yl)ethynyl)-4-chlorobenzamide

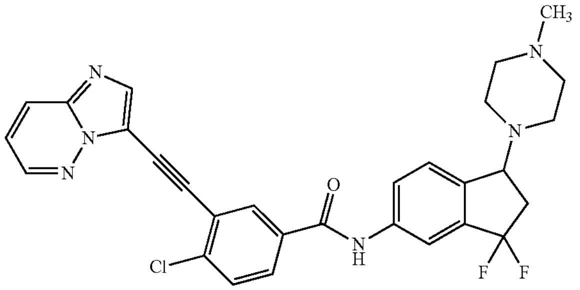

The title compound was synthesized from 3-Ethynylimidazo[1,2-b]pyridazine and 4-chloro-N-(3,3-difluoro-1-(4-methylpiperazin-1-yl)-2,3-dihydro-1 H-indan-5-yl)-3-iodobenzamide in a manner similar to that described in Example 1. The product was obtained as a pale yellow solid. Mp: 140-142° C. $^1$H NMR (300 MHz, $CDCl_3$) δ: 2.33 (3 H, s), 2.50-2.64 (10 H, m), 4.50 (1 H, m), 7.11-7.16 (1 H, dd, J=9.0 and 4.5 Hz), 7.46-7.48 (1 H, d, J=7.8 Hz), 7.55-7.58 (1 H, d, J=8.4 Hz), 7.84-7.94 (4 H, m), 8.11 (1 H, s), 8.15 (1 H, s), 8.49-8.50 (1 H, d, J=3.6 Hz), 8.57 (1 H, s). HRMS (ESI-TOF$^+$): m/z $[M+2H]^{+2}$ calcd for $C_{29}H_{27}ClF_2N_6O$: 274.0951. found: 274.0962.

Example 39

N-(1,1-difluoro-2,3-dihydro-3-(4-methylpiperazin-1-yl)-1H-indan-6-yl)-3-(2-(imidazo[1,2-b]pyridazin-3-yl)ethynyl)-4-fluorobenzamide

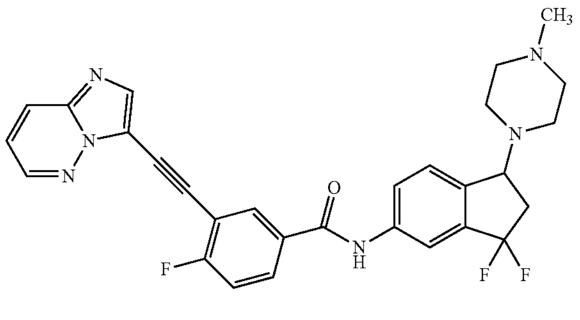 [SMILES: CN1CCN(C2CC(F)(F)c3cc(NC(=O)c4ccc(F)c(C#Cc5cnc6cccnn56)c4)ccc32)CC1]

Step 1. N-(1,1-difluoro-2,3-dihydro-3-(4-methylpiperazin-1-yl)-1H-indan-6-yl)-3-iodo-4-fluorobenzamide

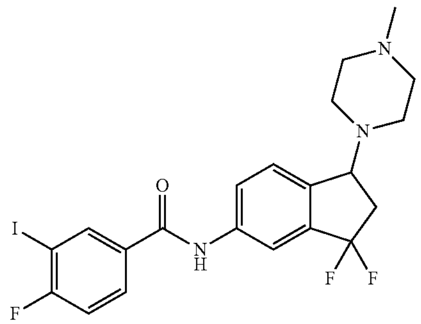 [SMILES: CN1CCN(C2CC(F)(F)c3cc(NC(=O)c4ccc(F)c(I)c4)ccc32)CC1]

The title compound was synthesized from 4-fluoro-3-iodobenzoic acid and 1-(1,1-difluoro-2,3-dihydro-6-amino-1H-indan-3-yl)-4-methylpiperazine (as prepared in Example 36 step 6) in a manner similar to that described in Example 36 step 7. The product was obtained as a pale yellow solid. LCMS: m/z $[M+H]^+$ 516.1312.

Step 2. N-(1,1-difluoro-2,3-dihydro-3-(4-methylpiperazin-1-yl)-1H-indan-6-yl)-3-(2-(imidazo[1,2-b]pyridazin-3-yl)ethynyl)-4-fluorobenzamide

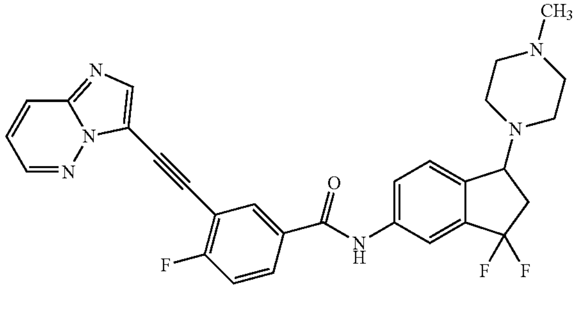 [SMILES: CN1CCN(C2CC(F)(F)c3cc(NC(=O)c4ccc(F)c(C#Cc5cnc6cccnn56)c4)ccc32)CC1]

The title compound was synthesized from 3-Ethynylimidazo[1,2-b]pyridazine and 4-fluoro-N-(1,1-difluoro-2,3-dihydro-3-(4-methylpiperazin-1-yl)-1 H-indan-6-yl)-3-iodobenzamide in a manner similar to that described in Example 1. The product was obtained as a pale yellow solid. Mp: 118-121° C. $^1$H NMR (400 MHz, $CDCl_3$) δ: 2.38 (3 H, s), 2.53-2.57 (2 H, m), 2.59-2.66 (8 H, m), 4.49-4.51 (1 H, d, J=6.4 Hz), 7.12-7.16 (1 H, m), 7.22-7.24 (1 H, d, J=8.8 Hz), 7.86-7.89 (2 H, m), 7.94-7.96 (2 H, m), 8.11-8.12 (1 H, d, J=4 Hz), 8.13 (1 H, s), 8.48-8.50 (1 H, dd, J=4.4 and 1.6 Hz), 8.56 (1 H, s). HRMS (ESI-TOF$^+$): m/z $[M+H]^{+1}$ calcd for $C_{29}H_{26}F_3N_6O$: 531.2115. found: 531.2120.

Example 40

Separation of the Optical Isomers of Compound 36 Obtained in Example 36 and Determination of the Absolute Configurations Thereof The racemate product (5.0 g) obtained in Example 36 was subjected to a separation with SFC (Supercritical Fluid Chromatography) method by the chiral column (CHIRALCEL AS-H, 0.46 cm I.D.×25 cm L) (see FIG. 1). The products were respectively collected at Peak 1 with retention time of 16.817 min (hereinafter also referred to as HAP-71-P1, 2.8257 g, $[\alpha]_D^{20}$ =+15.96° (c=1.0, $CHCl_3$)) and Peak 2 with retention time of 21.378 min (hereinafter also referred to as HAP-71-P2, 2.5913 g, $[\alpha]_D^{20}$=−16.19° (c=1.0, $CHCl_3$)).

The absolute configuration determination of the above separated products was performed according to the method described as follows.

Step 1. Preparation of (S)-1-(1,1-Difluoro-2,3-dihydro-6-nitro-1H-indan-3-yl)-4-methylpiperazine (hereinafter referred to as HA-6-13-1)

HA-6-13-1

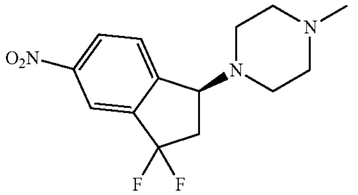

To a racemic mixture of 1-(1,1-Difluoro-2,3-dihydro-6-nitro-1H-indan-3-yl)-4-methylpiperazine (1 g, 4 mmol) in 10 mL methanol was added D-camphor-10-sulfonic acid (1.84 g, 8 mmol) at room temperature, then 5 mL iso-propanol was added. The mixture was refluxed and cooled to room temperature. The solution was stayed at −20° C. for 5 days, the result solid was collected by filtration. The solid was recrystallized in a solution of methanol:iso-propanol=1:2 for four times to give 220 mg colorless solid. The solid was dissovled in 10 mL $CH_2Cl_2$ and 5 mL 1M NaOH solution was added therein, the mixture was stirred for 0.5 h, and the aqueous layer was seperated, which was further extracted with $CH_2Cl_2$ (2×10 mL). The organic layers were combined and washed with brine, dried over $Na_2SO_4$, evaporated to give product 55 mg(hereinafter referred to as HA-6-13-1). $[\alpha]_D^{20}$=+18.51° (c=1.1, $CHCl_3$).

The compound 1-(1,1-Difluoro-2,3-dihydro-6-nitro-1H-indan-3-yl)-4-methylpiperazine theoretically theoretically has two optical isomers, hereinafter respectively referred to as ZDF2a and ZDF2b, as shown in below table.

ZDF2a

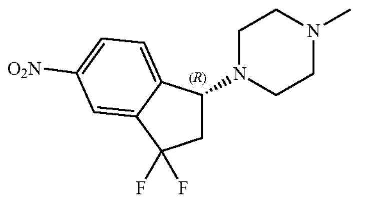

ZDF2b

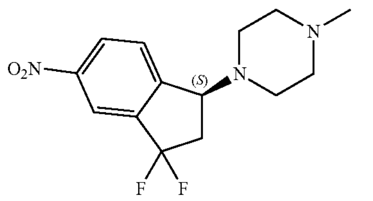

Figure 2:
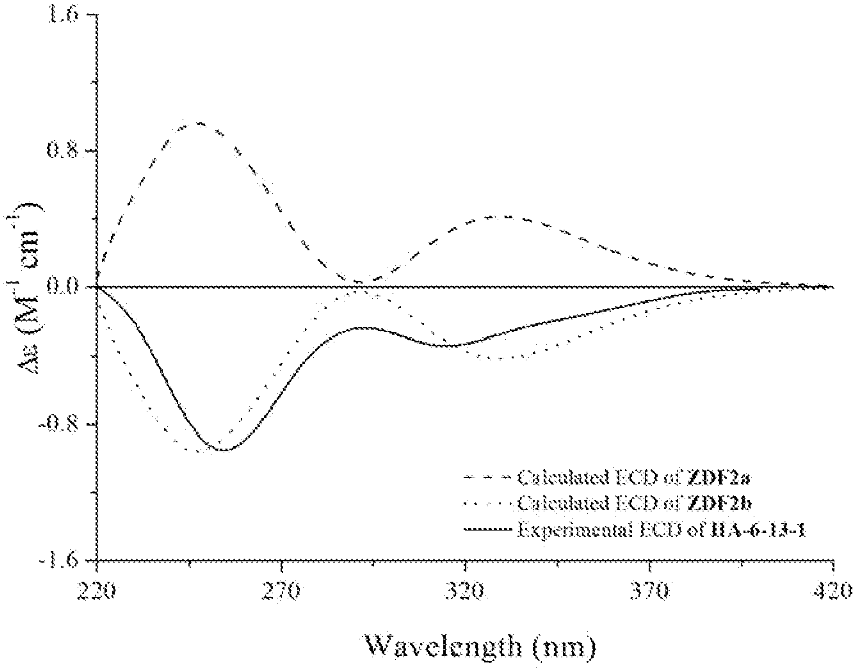
FIG. 2: shows the experimental ECD spectrum of Compound HA-6-13-1 and the calculated ECD spectra of the optical isomers ZDF2a and ZDF2b.

The absolute configuration of the above prepared Compound HA-6-13-1 was determined by comparison of the experimental ECD spectrum of Compound HA-6-13-1 and the corresponding calculated ECD spectra of the optical isomers ZDF2a and ZDF2b. The MMFF94 (Merck Molecular Force Field 94) conformational search followed by reoptimization using density functional theory with B3LYP/6-31G(d) (the Becke 3-Lee-Yang-Parr exchange-correlation functional) method afforded eleven lowest energy conformers. The overall ECD spectra of enantiomers ZDF2a and ZDF2b were then generated by Boltzmann weighting of the ECD spectra of eleven conformers. The ECD spectrum recorded for HA-6-13-1 matches the calculated ECD curve of ZDF2b, but is opposite to that of ZDF2a (see FIG. 2). Therefore, Compound HA-6-13-1 was deduced to have the S absolute configuration.

Step 2. Preparation of (S)-N-(1,1-difluoro-2,3-dihydro-3-(4-methylpiperazin-1-yl)-1H-indan-6-yl)-3-iodo-4-methylbenzamide

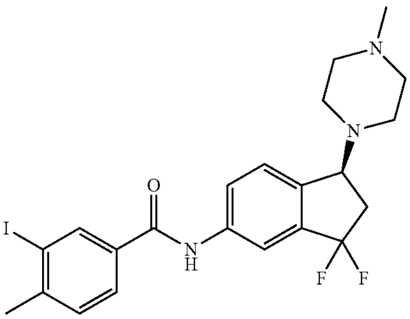 [SMILES: Cc1ccc(C(=O)Nc2ccc3c(c2)C(F)(F)C[C@@H]3N2CCN(C)CC2)cc1I]

The title compound was synthesized from 3-iodo-4-methylbenzoic acid and (S)-1-(1,1-difluoro-2,3-dihydro-6-amino-1H-indan-3-yl)-4-methylpiperazine (prepared from HA-6-13-1) in a manner similar to that described in Example 36 step 7. The product was obtained as a pale yellow solid. LCMS: m/z $[M+H]^+$ 512.1088.

Step 3. Preparation of (S)-N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide (corresponding to Compound 36-(S))

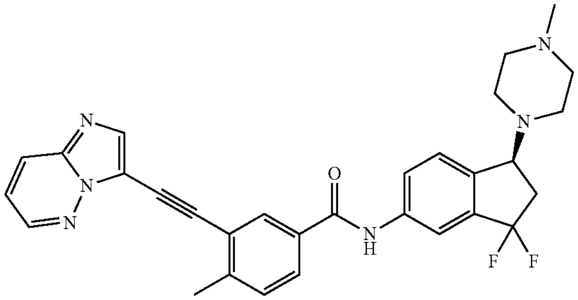 [SMILES: Cc1ccc(C(=O)Nc2ccc3c(c2)C(F)(F)C[C@@H]3N2CCN(C)CC2)cc1C#Cc1cnc2cccnn12]

The title compound was synthesized from 3-Ethynylimidazo[1,2-b]pyridazine and (S)-N-(1,1-difluoro-2,3-dihydro-3-(4-methylpiperazin-1-yl)-1 H-indan-6-yl)-3-iodo-4-methylbenzamide in a manner similar to that described in Example 1. The product was obtained as a pale yellow solid. HRMS (ESI-TOF$^+$): m/z $[M+2H]^{+2}$ calcd for $C_{30}H_{30}F_2N_6O$: 264.1219; found: 264.1216.

Figure 3:
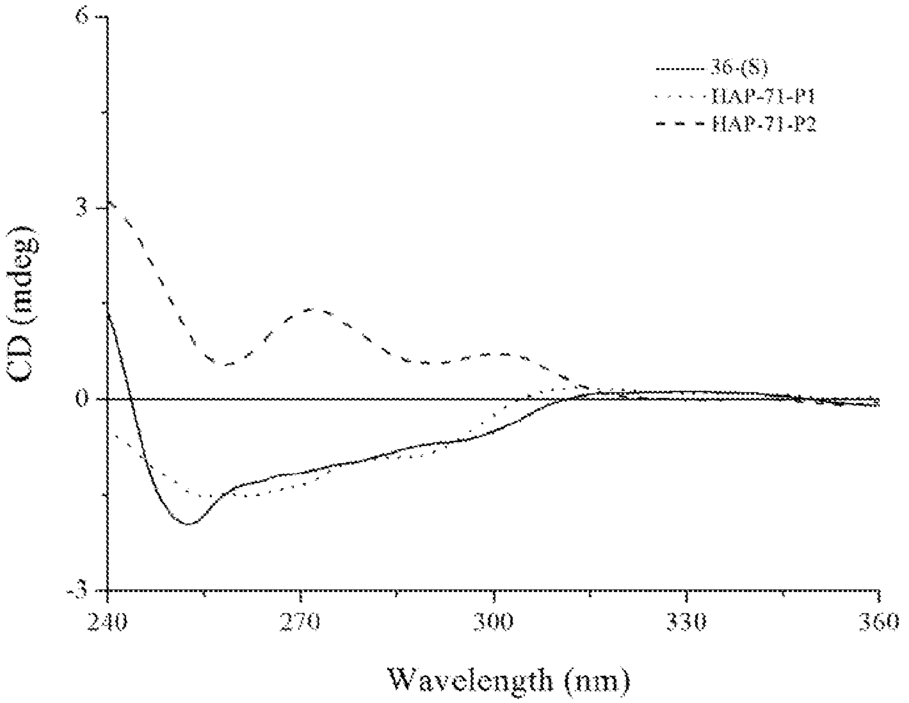
FIG. 3: shows the ECD spectra of prepared (S)-N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide (i.e. Compound 36-(S)), HAP-71-p1 and HAP-71-p2.

The ECD spectrum recorded for the above prepared compound matches the curve of the above separated product HAP-71-p1(collected at peak 1), but is opposite to that of product HAP-71-p2(collected at peak 2) (see FIG. 3). Therefore, HAP-71-p1 was deduced to have the S absolute configuration.

Figure 4:
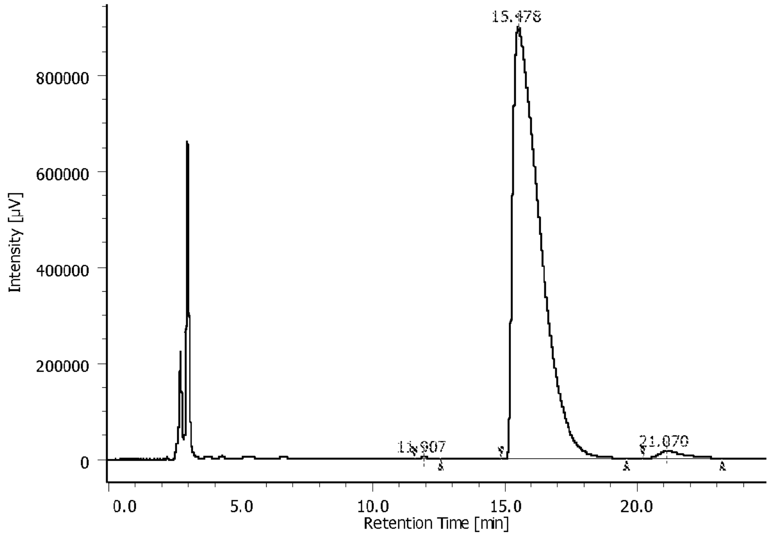
FIG. 4: shows the chiral column result of prepared(S)-N-(1,1-difluoro-2,3-dihydro-3-(4-methylpiperazin-1-yl)-1H-indan-6-yl)-3-(2-(imidazo[1,2-b]pyridazin-3-yl)ethynyl)-4-methylbenzamide (i.e. Compound 36-(S)).

For further confirmation that the product HAP-71-p1(collected at peak 1) has the same absolute configuration as the above prepared (S)-N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-methylbenzamide (Compound 36-(S)), the prepared Compound 36-(S) was subjected to passing through the chiral column (CHIRALCEL AS-H, 0.46 cm I.D.×25 cm L), and the result of the chiral column analysis was consistent with ECD spectrum (please see FIG. 4).

So the absolute configuration of HAP-71-P2 was R, as shown in below.

36-(R)

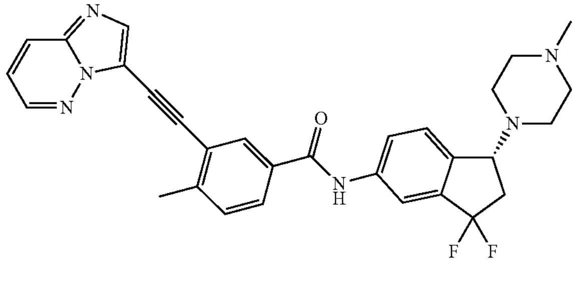

Example 41

Separation of the Optical Isomers of Compound 37 Obtained in Example 37

Figure 5:
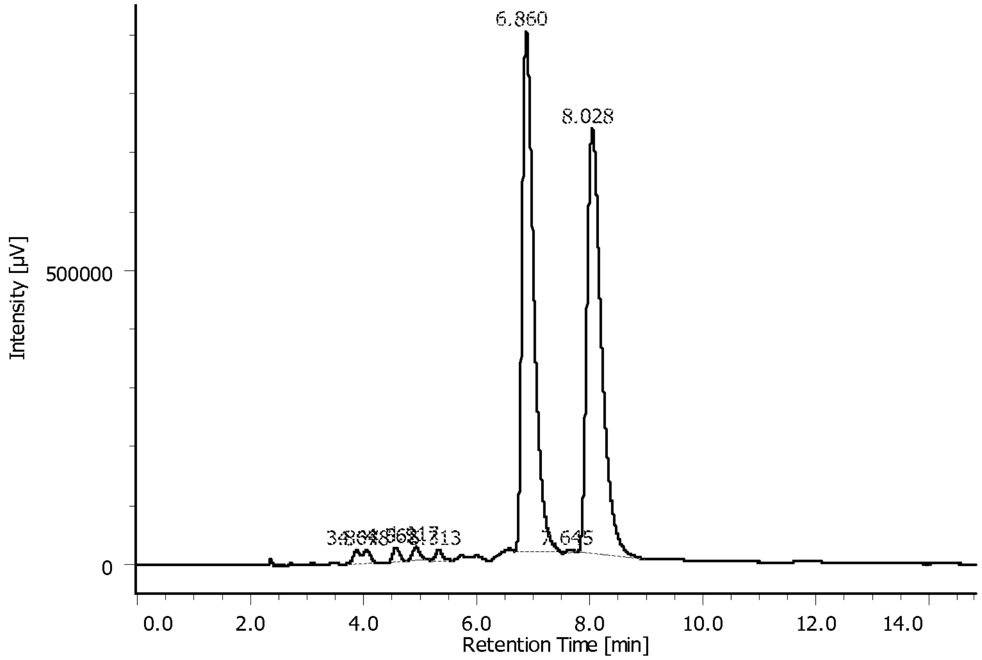
FIG. 5. shows the spectrogram for separation of the optimal isomers of Compound 37 by SFC method with a chiral column.

The racemate product (0.1631 g) obtained in Example 37 was subjected to a separation with SFC (Supercritical Fluid Chromatography) method by the chiral column (CHIRALCEL OJ-H, 0.46 cm I.D.×25 cm L). The products collected at Peak 1 (0.0566 g, $[\alpha]_D^{20}$=+14.79° (c=1.0, $CHCl_3$)) and Peak 2 (0.0694 g, $[\alpha]_D^{20}$=−12.69° (c=1.0, $CHCl_3$))(see FIG. 5) were proved to be isomers having the absolute configurations of S and R, respectively (the determination was based on ECD study in a manner similar to that described in Example 40).

Example 42

Separation of the Optical Isomers of Compound 38 Obtained in Example 38

Figure 6:
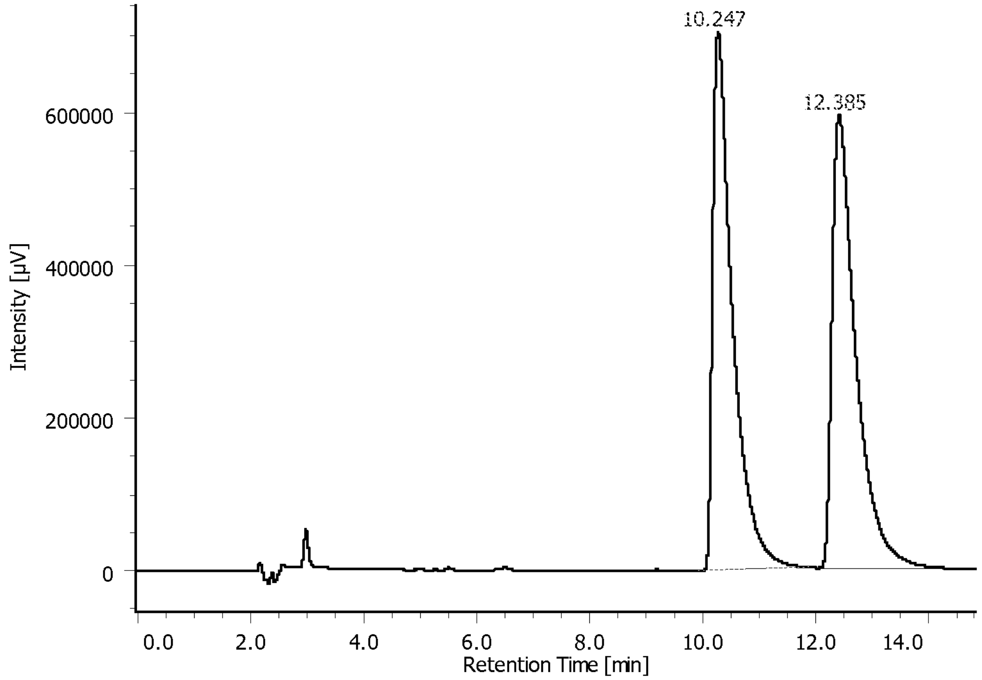
FIG. 6: shows the spectrogram for separation of the optimal isomers of Compound 38 by SFC method with a chiral column.

The racemate product (0.2882 g) obtained in Example 36 was subjected to a separation with SFC (Supercritical Fluid Chromatography) method by the chiral column (CHIRALCEL OJ-H, 0.46 cm I.D.×25 cm L). The products collected at Peak 1 (0.1228 g, $[\alpha]_D^{20}$=+14.53° (c=1.0, $CHCl_3$)) and Peak 2 (0.1472 g, $[\alpha]_D^{20}$ =−14.21° (c=1.0, $CHCl_3$)) (see FIG. 6) were proved to be isomers having the absolute configurations of S and R, respectively (the determination was based on ECD study in a manner similar to that described in example 40).

Example 43

Separation of the Optical Isomers of Compound 39 Obtained in Example 39

Figure 7:
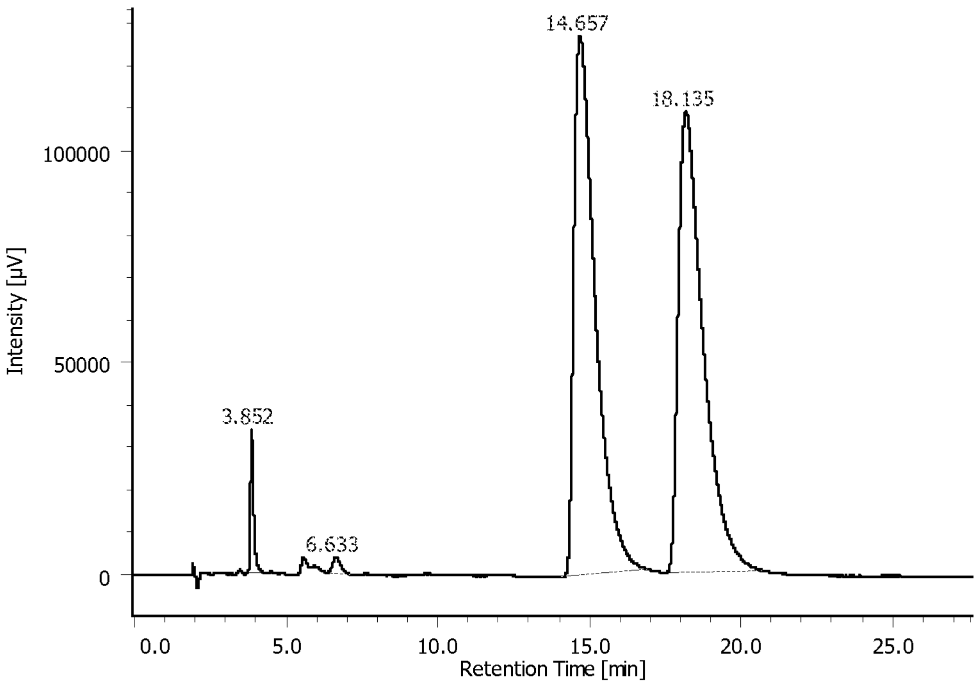
FIG. 7: shows the spectrogram for separation of the optimal isomers of Compound 39 by SFC method with a chiral column.

The racemate product (100 mg) obtained in Example 40 was subjected to a separation with SFC (Supercritical Fluid Chromatography)method by the chiral column (CHIRALCEL AS-H, 0.46 cm I.D.×25 cm L). The products collected at Peak 1 (40 mg, $[\alpha]_D^{20}$=+15.26° (c=1.0, $CHCl_3$)) and Peak 2 (43 mg, $[\alpha]_D^{20}$=−15.53° (c=1.0, $CHCl_3$)) (see FIG. 7) were proved to be isomers having the absolute configurations of S and R, respectively (the determination was based on ECD study in a manner similar to that described in example 40).

Biological Assay

The activity of the compounds of the present invention can be evaluated using the following assays.

Assessment of Cell Death Assay

Method of cell death assay:

Experiment 1:

K562 cells were seeded in 24-well plates with 1.5×$10^5$ cells/ml/well, then cells were treated AP-245534 and test compounds dosed as 100 nM 48 hours. Then cells were harvested at 4000 rpm×4 min, and resuspended with 150 ul PBS, live cells were counted with TC10 via trypan blue methods.

Results:

TABLE 1

Compound activities in killing K562 cells at 100 nM (% live cells vs control)

| Compound | % live cells |
|---|---|
| 3 | 11.3 |
| 5 | 10.8 |
| 6 | 10.1 |
| 10 | 11 |
| 12 | 10.1 |
| 13 | 8.9 |
| 14 | 8.37 |
| 15 | 17 |
| 16 | 8.46 |
| 17 | 18.3 |
| 23 | 8.6 |
| 24 | 16.4 |
| 26 | 18.3 |
| 28 | 12.7 |
| 29 | 5.87 |
| 30 | 12.6 |
| 31 | 14.4 |
| 32 | 9.57 |
| 33 | 7.97 |
| 34 | 12 |
| 35 | 11.3 |
| 36 | 9.48 |
| 37 | 4.32 |
| negative control | 100 |
| AP-24534* | 10.1 |

*The structure of AP-24534 is below (J. Med. Chem., 2010, 53, 4701-4719),

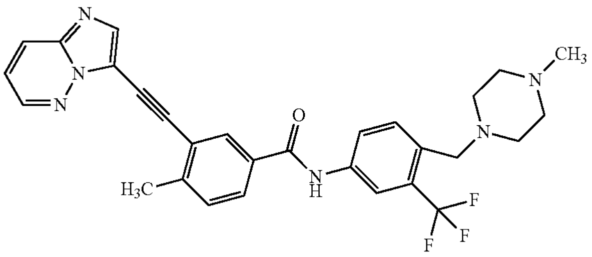 [SMILES: Cc1ccc(C(=O)Nc2ccc(CN3CCN(C)CC3)c(C(F)(F)F)c2)cc1C#Cc1cnc2cccnn12]

Experiment 2:

K562 cells (2×$10^5$ cells/ml) were seeded in 24-well cell culture plate and treated with DMSO or agents. After treatment in the presence of DMSO or agents for 48 h, cells were collected by centrifuging at 500 g for 5 minutes, and then cells were resuspended in appropriate volume of PBS. 10 uL of cell suspension was mixed with 10 uL of trypan blue solution and live cells were counted by TC10 (Bio-Rad, Richmond, Calif.).

Results:

TABLE 2

Some representative compounds $IC_{50}$ values

| Compound | $IC_{50}$ (nM) |
|---|---|
| 3 | 3 |
| 12 | 4 |
| 13 | 11 |
| 23 | 16 |
| 30 | 3.6 |
| 36 | 0.87 |
| 37 | 3.4 |

As seen in the Experiment 2 above, compounds of the instant invention that had an $IC_{50}$ value greater than 0 nM but less than 20 nM were given an "A" rating. Compounds of the instant invention that had an $IC_{50}$ value equal to, or greater than, 20 nM, but less than 1000 nM, were given a "B" rating.

Experiment 3:

Methods:

This study evaluated the effect of the pure optical isomers on human leukemia cell viability in vitro. Ponatinib was used as the positive control. Two BCR-ABL-positive human leukemia cell lines, K562 and KU812, were used in this study. Besides, Ba/F3 cell transfectants expressing native or T315I BCR-ABL, whose viability is dependent on ectopically expressed BCR-ABL, were also used in this work. Ba/F3 cells expressing BCR-$ABL^{T315I}$ were used for testing the efficiency of tested compounds on point mutation BCR-$ABL^{T315I}$, which cause drug resistance to Imatinib (Gleevec). U937 and JURKAT, two BCR-ABL-negative human leukemia cell lines, were employed to test the selectivity of tested compounds.

Cells were seeded in 24-well plates, and treated with drugs at corresponding concentrations. Cell viability was measured using a MTT (3-(4,5-dimethylthiazol-2-yl)-2,5-diphenyltetrazolium bromide)-based colorimetric assay with a 96-well plate reader. IC50 values were calculated using the mean of two independent experiments.

Results: Effect of BCR-ABL inhibitors on cell viability of BCR-ABL-positive and – negative human leukemia cell lines and a panel of Ba/F3 cell transfectants (IC50 as Mean±S.E.M, nM).

The results showed that no matter the racemic compounds or the pure isomers with absolute configuration R or S show effect on leukemia cells or BaF3 cells expressing native BCR-ABL. Particularly, compounds 36-(S) and 38-(S) perform similarly on leukemia cells or BaF3 cells expressing native BCR-ABL, compared to reference compound Ponatinib. The compounds 36-(S) and 38-(S) work better on BaF3 cells expressing BCR-$ABL^{T315I}$ than reference compound Ponatinib, implying that the two compounds could be more potent in treating the patients developing drug resistance to imatinib, the first generation tyrosine kinase inhibitor. Besides, 36-(S) and 38-(S) are less potent on BCR-ABL-negative human leukemia cell lines U937 and JURKAT. It means that 36-(S) and 38-(S) may have better selectivity to BCR-ABL and less side-effect in clinical use.

TABLE 3

Effect of BCR-ABL inhibitors on cell viability of BCR-ABL-positive and -negative human leukemia cell lines and Ba/F3 cell transfected cells (IC50 as Mean ± S.E.M, nM)

| | Ba/F3 cells | | CML leukemia cells | | Non-CML leukemia cells | |
|---|---|---|---|---|---|---|
| Compound | Native BCR-ABL | T315I BCR-ABL | K562 | KU812 | U937 | JURKAT |
| Ponatinib | 0.9 ± 0.1 | 9.6 ± 1.7 | 0.3 ± 0.1 | 0.1 ± 0.1 | 245.8 ± 12.5 | 295.0 ± 5.0 |
| 36 | 2.7 ± 0.2 | 11.0 ± 0.2 | 0.5 ± 0.1 | 0.2 ± 0.1 | 607.8 ± 42.2 | 672.4 ± 77.6 |
| 36-(S) | 2.1 ± 0.2 | 4.7 ± 1.3 | 0.4 ± 0.1 | 0.1 ± 0.1 | 867.6 ± 88.7 | 850.7 ± 25.7 |
| 36-(R) | 31.2 ± 3.8 | >100 | 3.6 ± 0.1 | 2.7 ± 0.1 | >1000 | >1000 |
| 37 | 9.3 ± 2.5 | 40.0 ± 9.6 | 1.0 ± 0.2 | 0.4 ± 0.1 | 190.8 ± 3.3 | 292.0 ± 8.0 |
| 37-(S) | 3.5 ± 0.9 | 12.4 ± 0.4 | 0.6 ± 0.1 | 0.2 ± 0.1 | 165.0 ± 15.0 | 280.0 ± 20.0 |
| 37-(R) | 62.5 ± 6.9 | >100 | 10.4 ± 1.5 | 5.2 ± 0.2 | 465.3 ± 9.7 | 399.9 ± 64.9 |
| 38 | 4.9 ± 2.1 | 10.1 ± 0.7 | 0.8 ± 0.1 | 0.4 ± 0.1 | >1000 | >1000 |
| 38-(S) | 2.2 ± 0.3 | 3.8 ± 0.2 | 0.6 ± 0.1 | 0.2 ± 0.1 | >1000 | >1000 |
| 38-(R) | 78.2 ± 2.3 | >100 | 24.9 ± 9.9 | 11.9 ± 0.3 | >1000 | >1000 |
| 39 | 3.6 ± 0.7 | 13.0 ± 0.9 | 0.8 ± 0.2 | 0.5 ± 0.3 | 809.8 ± 39.2 | >1000 |
| 39 (S) | 2.3 ± 0.5 | 6.5 ± 1.2 | 0.3 ± 0.2 | 0.2 ± 0.1 | >1000 | >1000 |
| 39 (R) | 47.6 ± 4.5 | >100 | 6.4 ± 1.3 | 3.6 ± 0.8 | >1000 | >1000 |

Experiment 4:

Methods

The murine pro-B cell line Ba/F3 harboring the T315I mutant isoform of BCR-ABL was subcutaneously injected into NOD SCID mice (NOD.CB17-$Prkdc^{scid}$/J). Mice were dosed orally with tested compounds for 14 days: Ponatinib used as the positive drug at doses of 10 or 20 mg/kg/day; Compound 36-(S) at doses of 10 or 20 mg/kg/day; Compound 38-(S) at dose of 5 mg/kg/day. The tumor volumes in two dimensions and the body weights of the mice were measured three times a week (volume=L×$W^2$×0.5).

Figure 8:
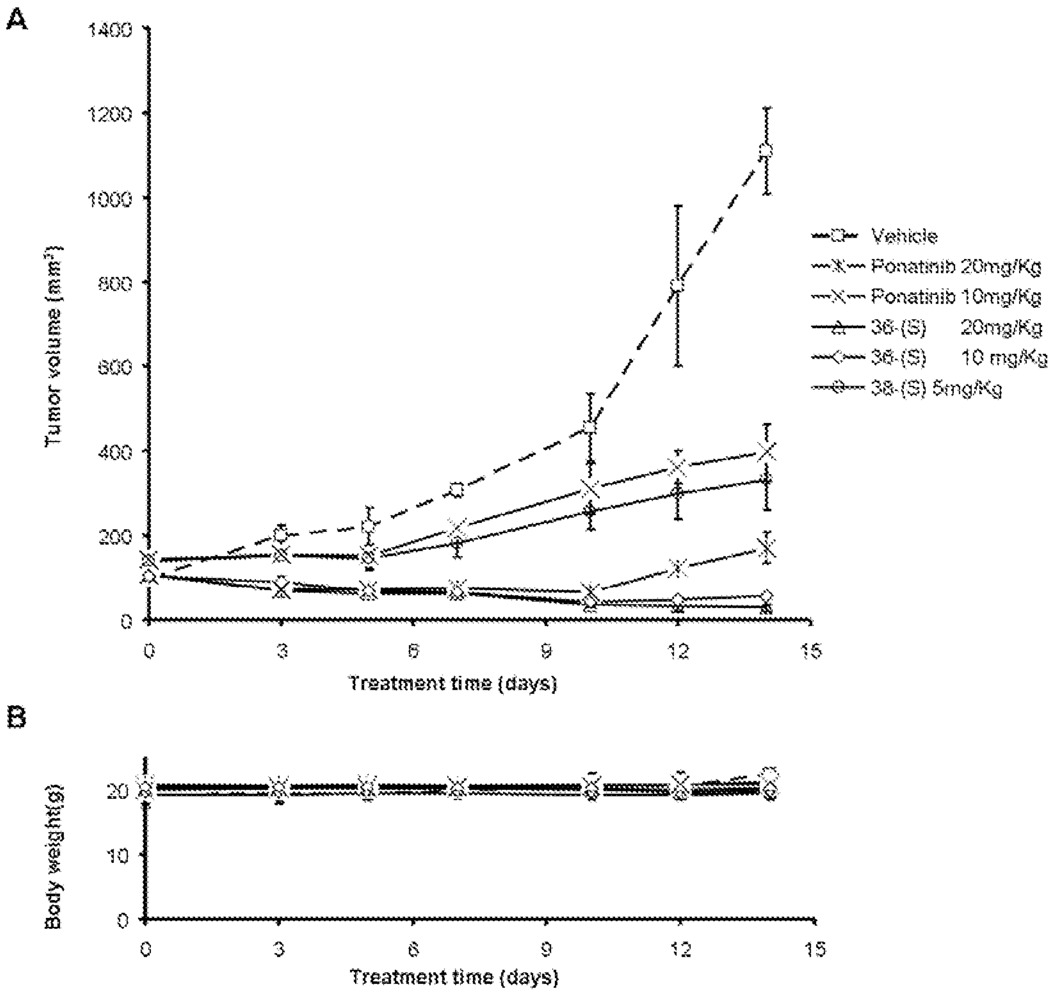
FIG. 8: shows the tumor volume (A) and body weight (B) during the treatment of BCR-ABL inhibitors.

Results:

The TGI (Tumor growth inhibition) for the drugs are: Ponatinib 20 mg/kg/day, 94%; Ponatinib 10 mg/kg/day, 75%; Compound 36-(S) 20 mg/kg/day, 108%; Compound 36-(S) 10 mg/kg/day, 105%; Compound 38-(S) 5 mg/kg/day, 81%. The TGI greater than 100% means that tumors treated with drugs over 14 days are smaller than their original sizes. The mouse body weight didn't change obviously over the treatment period at the described doses. The results are also shown in FIG. 8, A and B.

From the animal experiment results, we can conclude that 36-(S) at the dose of 10 mg/kg/day works better than Ponatinib at the dose of 20 mg/kg/day. 38-(S) at the dose of 5 mg/kg/day works better than Ponatinib at the dose of 10 mg/kg/day. Overall, 36-(S) and 38-(S) are more potent than Ponatinib in BaF3/BCR-$ABL^{T315I}$ mouse xenograft model.

The above results suggest the compounds of the present invention, preferred the racemic compounds or the optical isomers represented by Formula VIII, and more preferred the compounds represented by Formula VIII with absolute configuration S have good effects on inhibiting protein kinase, such as Bcr-Abl, c-Kit, c-Src, FGFR1, FLT3, LYN, PDGFR, particularly Bcr-Able (T315I); inhibiting or curing cancers, such as Chronic Myelogenous Leukemia (CML), Acute Lymphocytic Leukemia (ALL), Non-Small Cell Lung Cancer (NSCLC), Gastrointestinal stromal tumor (GIST), Acute Myelogenous Leukemia (AML), particularly Chronic Myelogenous Leukemia (CML); and inhibiting and/or treating inflammation such as Asthma, Rheumatoid Arthritis.

What is claimed is:

1. A compound of Formula VIII with absolute configuration R or S, or a pharmaceutically acceptable salt, hydrate, or solvate thereof:

VIII

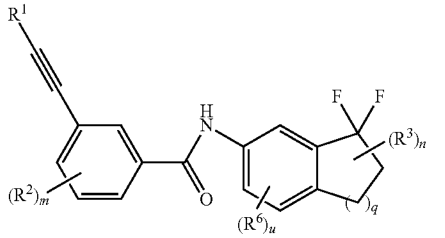

wherein, $R^1$ is selected from:

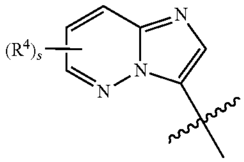
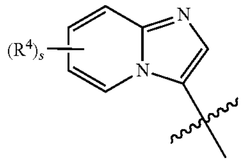
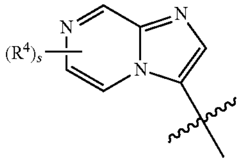
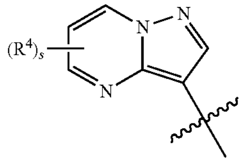
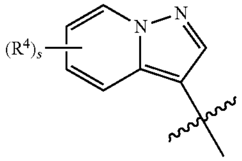
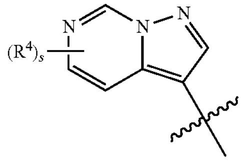
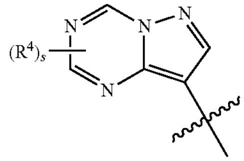
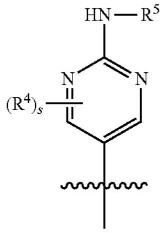
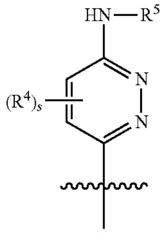
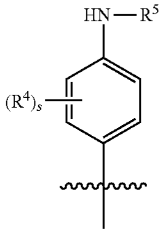
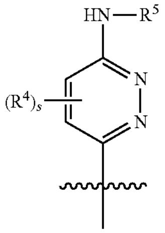
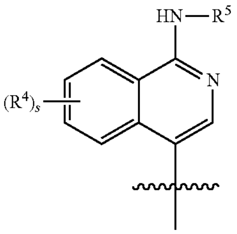
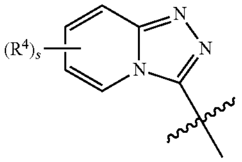

-continued

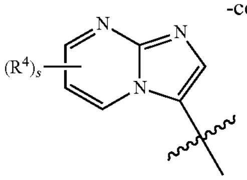
and
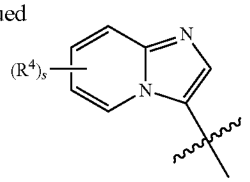

$R^2$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^3$ is

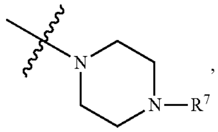
, or
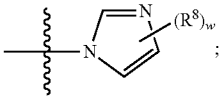
;

$R^4$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^5$ is independently H, $C_1$-$C_6$ alkyl, $C_3$-$C_6$ cycloalkyl, phenyl, or benzyl;

$R^6$ is independently H, halogen, CN, $NO_2$, $CF_3$, $OCF_3$, $NH_2$, $NR^eR^f$, $C_1$-$C_6$ alkyl, $C_3$-$C_6$ cycloalkyl, $OCH_3$, $COOCH_3$, or $NHCOCH_2CH_3$;

$R^7$ is independently H, $C_1$-$C_6$ alkyl, or $C_3$-$C_6$ cycloalkyl;

$R^8$ is independently H, halogen, CN, $NO_2$, $CF_3$, $NH_2$, $NR^eR^f$, $C_1$-$C_6$ alkyl, or $C_3$-$C_6$ cycloalkyl;

$R^e$ and $R^f$ is independently $C_1$-$C_6$ alkyl;

m is 0, 1, or 2;

n is 0, 1, or 2;

w is 0, 1, or 2;

s is 0, 1, or 2;

u is 0, 1, or 2; and q is 1 or 2.

2. The compound of claim 1, the compound is represented by Formula VIIIa, VIIIb or VIIIc:

VIIIa

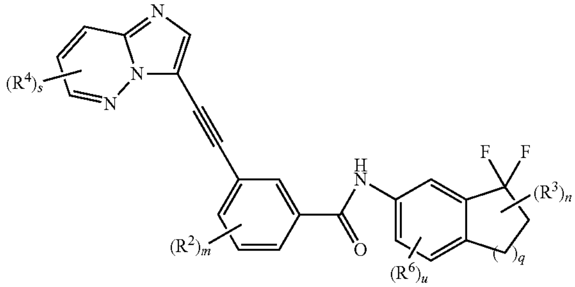

-continued

VIIIb

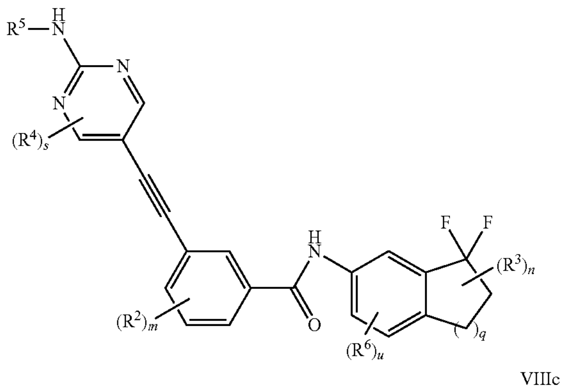

VIIIc

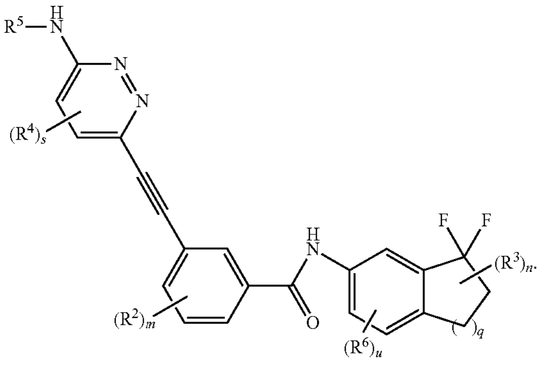

3. The compound of claim 2, wherein $R^2$ is H, $CH_3$, F or Cl; $R^3$ is

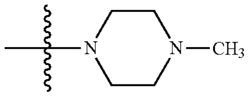

or

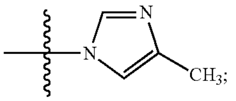

$R^5$ is cyclopropyl, cyclobutyl, or isopropyl; $R^6$ is H or $CF_3$; and s is 0, u is 0, m is 0 or 1, n is 1 and q is 1.

4. The compound of claim 1, wherein the compound is
(R)—N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-methylbenzamide;
(S)-N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-methylbenzamide;
(R)-3-(2-(2-(Cyclopropylamino)pyrimidin-5-yl)ethynyl)-N-(1,1-difluoro-2,3-dihydro-3-(4-methylpiperazin-1-yl)-1 H-indan-6-yl)-4-methylbenzamide;
(S)-3-(2-(2-(Cyclopropylamino)pyrimidin-5-yl)ethynyl)-N-(1,1-difluoro-2,3-dihydro-3-(4-methylpiperazin-1-yl)-1 H-indan-6-yl)-4-methylbenzamide;
(R)—N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-chlorobenzamide;
(S)-N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-chlorobenzamide.
(R)—N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-fluorobenzamide;
(S)-N-(1,1-difluoro-2,3-dihydro-3-(4-methylpiperazin-1-yl)-1 H-indan-6-yl)-3-(2-(imidazo[1,2-b]pyridazin-3-yl)ethynyl)-4-fluorobenzamide.

5. A pharmaceutical composition comprising at least one compound of claim 1 or a salt, hydrate, or solvate thereof, and one or more pharmaceutically acceptable carriers and/or additives.

6. A method for inhibiting protein kinase comprising administering a therapeutically effective amount of a compound of claim 1, or a salt, hydrate, or solvate thereof, or a pharmaceutical composition of claim 5, wherein said protein kinase is selected from the group consisting of Bcr-Abl, c-Kit, c-Src, FGFR1, FLT3, LYN and PDGFR.

7. A method of treating leukemia in a human patient in need of, comprising administering a therapeutically effective amount of a compound of claim 1, or a salt, hydrate, or solvate thereof, or a pharmaceutical composition of claim 5.

8. The method of claim 7, wherein said leukemia is selected from Chronic Myelogenous Leukemia (CML), Acute Lymphocytic Leukemia (ALL), and Acute Myelogenous Leukemia (AML).

* * * * *